(12) United States Patent
Higo et al.

(10) Patent No.: US 7,255,990 B2
(45) Date of Patent: Aug. 14, 2007

(54) METHOD FOR SCREENING GENES EXPRESSING AT DESIRED SITES

(75) Inventors: Kenichi Higo, Tsukuba (JP); Masao Iwamoto, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 399 days.

(21) Appl. No.: 10/221,596

(22) PCT Filed: Nov. 21, 2001

(86) PCT No.: PCT/JP01/10195

§ 371 (c)(1),
(2), (4) Date: Sep. 11, 2002

(87) PCT Pub. No.: WO03/044227

PCT Pub. Date: May 30, 2003

(65) Prior Publication Data

US 2004/0086855 A1 May 6, 2004

(51) Int. Cl.
*C12Q 1/68* (2006.01)
(52) U.S. Cl. ........................................................ 435/6
(58) Field of Classification Search .................. 435/6, 435/91.1, 91.2; 536/23.1, 23.5
See application file for complete search history.

(56) References Cited

U.S. PATENT DOCUMENTS 5,569,831 A * 10/1996 DellaPenna ................. 800/286
6,576,815 B1 * 6/2003 Higo et al. .................. 800/287

OTHER PUBLICATIONS

Iwamoto et al. Atourist element in the 5'-flanking region of the catalase gene CatA reveals evolutionary relationships among Oryza species with various genome types. 1999. Mol. Gen. Genetics 262:493-500.*
Iwamoto et al. Mol. Gen. Genet. vol. 262:493-500. 1999.*
McSteen et al. Development. vol. 125:2359-2369. Sep. 1998.*
Higo et al. Plant Molecular Biology vol. 30:505-521. 1996.*

* cited by examiner

*Primary Examiner*—Gary Benzion
*Assistant Examiner*—Heather Calamita
(74) *Attorney, Agent, or Firm*—Perkins Coie LLP; Jacqueline F. Mahoney

(57) ABSTRACT

The present invention relates to a method for inferring a plant organ, in which a certain gene is to be expressed, using a part of a base sequence, a method for searching for a gene which is to be expressed at a desired site, and a composition, kit, system and program for carrying out these methods. The present invention also relates to a method for inferring a plant organ, in which a plant gene is to be expressed, based on information about the presence or absence of a base sequence which is highly similar to a transposable element in the vicinity of a protein coding region of a plant gene.

9 Claims, 10 Drawing Sheets

FIG. 4

| | L | R | F | S | cycles |
|---|---|---|---|---|---|
| CDS3 | | | | | 29 |
| CDS6 | | | | | 25 |
| CDS7 | | | | | 26 |
| CDS8 | | | | | 26 |
| CDS9 | | | | | 28 |
| CDS10 | | | | | 32 |
| CDS12 | | | | | 24 |
| CDS16 | | | | | 30 |
| CDS17 | | | | | 29 |
| CDS23 | | | | | 29 |
| CDS26 | | | | | 29 |

FIG. 7

METHOD FOR SCREENING GENES EXPRESSING AT DESIRED SITES

This application claims the benefit of PCT International Application Ser. No. PCT/JP01/10195 filed Nov. 21, 2001, which is incorporated herein by reference in its entirety.

TECHNICAL FIELD

The present invention relates to a method for inferring a plant organ, in which a certain gene is to be expressed, using a part of a base sequence; a method for searching for a gene which is to be expressed at a desired site (e.g., a site containing a flower); a composition, kit, system and program for carrying out these methods; and products obtained by these methods (nucleic acid molecule, etc.). More preferably, the present invention relates to a method for inferring a plant organ, in which a plant gene is to be expressed, based on information about the presence or absence of a the base sequence which is highly similar to a transposable element (e.g., transposon) in the vicinity of a protein coding region; a composition, kit, system, and program for carrying out the method; and products obtained by these methods.

BACKGROUND ART

Recent progress in genome base sequence analysis technologies has provided a rapid improvement in analysis speed and a reduction in analysis cost, whereby analysis of the structure of genomes of various organisms is proceeding at dramatic speed. Current methods for inferring a function of a gene from its deciphered base sequence depend on the presence or absence of a similar sequence found by searching sequence data of DNA or protein registered in an international database, such as GenBank or DDBJ, using, for example, PSI-BLAST algorithm (Altschul et al., Nucleic Acids Res. 25:3389-3402 (1997)) or the like. In these methods, the similarity between sequences and functions is estimated from the similarity between known nucleic acids or proteins and sequences. In order to estimate the amino acid sequence of a protein coded by a base sequence, various programs aimed at gene modeling for predicting the positions of exons or introns from the genome base sequence have been developed. An attempt to realize full automation is proceeding, however accurate gene modeling essentially requires manual editing of a result of prediction, though accuracy problems remain unsolved.

Some databases and programs for predicting gene expression sites based on a genome base sequence have been developed (Ghosh, Nucleic Acids Res., 21:3117-3118 (1993); Ghosh, Nucleic Acids Res., 26:360-361 (1998); Heinemeyer et al., Nucleic Acids Res., 26:362-367 (1998)), though accuracy problems remain unsolved.

For plants, a database compiling about 400cis element motifs in an expression control region for a plant gene, to which transcription regulatory elements bind has constructed (Higo et al., Nucleic Acids Res. 26:358-359 (1998); Nucleic Acids Res. 27:297-300 (1999)). When analysis is carried out using a base sequence inferred as a promoter as a query, each cis element motif present in the base sequence is displayed. However, although there is a possibility that these function as cis elements, no evidence exists that these actually function as cis elements. Therefore, there is a demand for the development of a method for inferring a gene expression site (expression tissue/expression organ) using a genome base sequence.

Clarification of gene expression sites would help reveal functions of individual genes and could make it possible to isolate and utilize a promoter portion. In the field of plants, development of tissue-specific promoters would make possible gene expression specific to individual tissues using transformation technologies or inhibition of gene expression. For example, if an anther-specific promoter were developed, the following applications would be expected.

It has been known that a F1 hybrid (first filial generation) generated by crossing between varieties may have a more excellent property than that of its parents. This inter-variety crossing has conventionally attracted attention as a method for breeding crops. For crops, such as rice, which perform self-pollination, methods for producing a male sterility strain have been studied as a technology required for utilization of such a property. Conventionally, male sterility strains have been searched for among plant gene resources, or mutagenesis has been used for selection of a male sterility strain. However, these methods have difficulty in introducing a male sterility gene into a commercial variety and their use is limited.

A recent promising approach is a method of utilizing biotechnology to link a promoter, which expresses in an anther and/or pollen, with a gene having a function to inhibit formation of an anther and/or pollen (e.g., nuclease, protease, and glucanase) and introduce the linked genes into a plant so as to prevent formation of fertile pollen. An alternative promising approach is a method of using a promoter, which is to be expressed in an anther and/or pollen, so as to transcribe antisense RNA for a gene which is to be expressed upon formation of an anther and/or pollen, or a method of introducing ribozyme, which decomposes mRNA for the gene, into a plant.

There are several known promoters for genes which are expressed in an anther and/or pollen. However, unfortunately, the activities of the promoters are too low for practical use, or the expression time thereof is limited. It would be very useful to isolate a promoter which functions at each developmental stage of an anther or pollen, clarify features of each promoter, and produce a promoter cassette having a high activity so as to artificially control formation of an anther and/or pollen.

Therefore, for example, if a promoter, which has a high activity, may be practically used, and is directed to a desired site (e.g., an anther or pollen), can be obtained from a gene of rice, such a promoter can contribute much to breeding of crops, such as rice. Further, in order to modify a component of each tissue of flower, such as a protein involved in adhesion of a petal pigment or pollen to a pistil, it is necessary to obtain a gene which is to be expressed in a flower.

To this end, required is a method for efficiently searching a DNA database, in which a vast number of genome base sequences are stored, for a gene which is to be expressed in a flower, or a method for efficiently screening a genome DNA library for a gene which is to be expressed in a desired site (e.g., flower).

DISCLOSURE OF THE INVENTION

To achieve the above-described objects, the present invention provides the following.

The present invention provides the following.

1. A method for detecting a gene which is to be expressed at a desired site in a plant, comprising the step of:

(1) searching a gene population using a transposon sequence as a key sequence.

2. A method according to item 1, further comprising the step of:
   (2) selecting a gene having similarity to the transposon sequence in the vicinity of a putative protein coding region.

3. A method according to item 1, wherein the transposon sequence is a MITE sequence.

4. A method according to item 1, wherein the desired site is a site containing a flower.

5. A method according to item 1, wherein the site containing a flower is a flower.

6. A method according to item 1, wherein the desired site contains at least one site selected from a stamen and a pistil.

7. A method according to item 1, wherein the plant is monocotyledon.

8. A method according to item 1, wherein the plant is rice.

9. A method according to item 1, wherein the transposon sequence is a Tourist sequence.

10. A method according to item 1, wherein the transposon sequence contains at least about 10 contiguous nucleotides in a sequence indicated by SEQ ID NO: 1.

11. A method according to item 1, wherein the transposon sequence contains at least about 15 contiguous nucleotides in the sequence indicated by SEQ ID NO: 1.

12. A method according to item 1, wherein the transposon sequence contains at least about 20 contiguous nucleotides in the sequence indicated by SEQ ID NO: 1.

13. A method according to item 1, wherein the transposon sequence contains at least about 50 contiguous nucleotides in the sequence indicated by SEQ ID NO: 1.

14. A method according to item 1, wherein the transposon sequence contains a sequence having at least about 70% homology to the sequence indicated by SEQ ID NO: 1.

15. A method according to item 1, wherein the transposon sequence contains a sequence having at least about 80% homology to the sequence indicated by SEQ ID NO: 1.

16. A method according to item 1, wherein the transposon sequence contains a sequence having at least about 90% homology to the sequence indicated by SEQ ID NO: 1.

17. A method according to item 1, wherein the transposon sequence has at least one substitution, addition or deletion in the sequence indicated by SEQ ID NO: 1.

18. A method according to item 1, wherein the transposon sequence is substantially the same as the sequence indicated by SEQ ID NO: 1.

19. A method according to item 1, wherein the transposon sequence contains a sequence having at least about 70% homology to the sequence indicated by SEQ ID NO: 2.

20. A method according to item 1, wherein the transposon sequence contains a sequence having at least about 80% homology to the sequence indicated by SEQ ID NO: 2.

21. A method according to item 1, wherein the transposon sequence contains a sequence having at least about 90% homology to the sequence indicated by SEQ ID NO: 2.

22. A method according to item 1, wherein the transposon sequence has at least one substitution, addition or deletion in the sequence indicated by SEQ ID NO: 2.

23. A method according to item 1, wherein the transposon sequence is substantially the same as the sequence indicated by SEQ ID NO: 2.

24. A method according to item 1, wherein the gene population is a database and the key sequence is a query sequence.

25. A method according to item 24, wherein the database is a DNA database.

26. A method according to item 24, wherein the search is carried out by a search method selected from the group consisting of BLAST, FASTA, Smith and Waterman method, and Needleman and Wunsch method.

27. A method according to item 1, wherein the gene population is a library and the key sequence is a probe sequence.

28. A method according to item 27, wherein the database is a DNA library.

29. A method according to item 27, wherein the search is carried out by a search method selected from the group consisting of stringent hybridization, microarray assay, PCR, and in situ hybridization.

30. A method according to item 2, wherein the vicinity of the putative protein coding region is within about 2 kbp upstream of a translation initiation codon, within about 1.1 kbp downstream of a translation termination codon, and within an intron.

31. A method according to item 2, wherein the similarity is at least about 66% homology.

32. A method according to item 2, wherein the similarity is about 70%.

33. A method according to item 2, wherein the similarity is about 80%.

34. A composition for detecting a gene which is to be expressed at a site containing a flower, comprising a plasmid containing at least about 10 contiguous nucleotides in the sequence indicated by SEQ ID NO: 1.

35. A kit for detecting a gene which is to be expressed at a desired site in a plant, comprising:
   (1) a plasmid containing at least about 10 contiguous nucleotides in the sequence indicated by SEQ ID NO: 1; and
   (2) a DNA library.

36. A method for producing a gene which is to be expressed at a desired site in a plant, comprising the steps of:
   (1) searching a gene population using a transposon sequence;
   (2) selecting a gene having similarity to the transposon sequence in a putative protein coding region; and
   (3) producing a nucleic acid molecule coding the gene.

37. A method according to item 36, wherein the production is carried out in vitro or in vivo.

38. A nucleic acid molecule coding a gene which is to be expressed at a desired site in a plant, wherein a base sequence of the nucleic acid molecule is obtained by a method comprising the step of:
   (1) searching a gene population using a transposon sequence as a key sequence.

39. A recording medium storing a program for allowing a computer to execute automatic computation for detecting a gene which is to be expressed at a desired site in a plant, the automatic computation comprises the steps of:
   (1) providing a transposon sequence as a query sequence;
   (2) providing a database;
   (3) searching the database using the query sequence; and
   (4) outputting a result of the search.

40. A program for allowing a computer to execute automatic computation for detecting a gene which is to be expressed at a desired site in a plant, the automatic computation comprising the steps of:
   (1) providing a transposon sequence (e.g., a MITE sequence, such as a Tourist sequence) as a query sequence;
   (2) providing a database;
   (3) searching the database using the query sequence; and
   (4) outputting a result of the search.

41. A system for detecting a gene which is to be expressed at a desired site in a plant, the system comprising:
(A) a computer; and
(B) a program for allowing a computer to execute automatic computation for detecting the gene which is to be expressed at the desired site in the plant,
wherein the automatic computation comprises the steps of:
(1) providing a transposon sequence as a query sequence;
(2) providing a database;
(3) searching the database using the query sequence; and
(4) outputting a result of the search.

42. A system according to item 41, wherein the computer is linked to a network.

43. A method for inferring an organ of a plant in which a gene is to be expressed, comprising the step of:
(1) obtaining information about whether or not abase sequence similar to the sequence of a transposable element is present in the vicinity of the gene, and when the similar sequence is present in the vicinity of the gene, inferring that the gene is to be expressed in the plant organ relating to the transposable element sequence.

44. A method according to item 43, wherein the plant organ relating to the transposable element sequence is a site containing a flower.

45. A method according to item 44, wherein the site containing a flower contains a site selected from the group consisting of a stamen and a pistil.

46. A method according to item 43, wherein the sequence similar to the transposable element sequence is a MITE sequence.

47. A method according to item 43, wherein the sequence similar to the transposable element sequence is a Tourist sequence.

48. A method according to item 43, wherein the plant includes rice.

49. A nucleic acid molecule coding a gene obtained by a method according to item 43.

50. A recording medium storing a sequence coding a gene obtained by a method according to item 43.

51. A method for modifying an expression pattern of a gene of a plant, comprising the step of utilizing the sequence of a gene obtained by a method according to item 43.

52. A kit for inferring a plant organ in which a gene is to be expressed, comprising:
(1) a molecule having a transposable element sequence.

53. A kit for inferring a plant organ in which a gene is to be expressed, comprising:
(1) a recording medium storing a transposable element sequence.

54. A recording medium storing a program for allowing a computer to execute automatic computation for inferring a plant organ in which a gene is to be expressed, the automatic computation comprising the steps of:
(1) providing a transposable element sequence as a query sequence;
(2) providing the sequence of the gene;
(3) comparing the query sequence with the sequence of the gene; and
(4) outputting a result of the comparison.

55. A program for allowing a computer to execute automatic computation for inferring a plant organ in which a gene is to be expressed, the automatic computation comprising the steps of:
(1) providing a transposable element sequence as a query sequence;
(2) providing the sequence of the gene;
(3) comparing the query sequence with the sequence of the gene; and
(4) outputting a result of the comparison.

56. A system for inferring a plant organ in which a gene is to be expressed, comprising:
(A) a computer; and
(B) a program for allowing the computer to execute automatic computation for inferring the plant organ in which the gene is to be expressed, the automatic computation comprising the steps of:
(1) providing a transposable element sequence as a query sequence;
(2) providing the sequence of the gene;
(3) comparing the query sequence with the sequence of the gene; and
(4) outputting a result of the comparison.

57. A system according to item 56, wherein the computer is linked to a network.

BRIEF DESCRIPTION OF THE DRAWINGS

FIG. 4 is a diagram showing a result of RT-PCR analysis for gene expression in each organ of rice of a putative protein coding region (CDS) in the vicinity of Tourist-OsaCatA in BAC/PAC clones. The same symbols as those in FIG. 2 indicate the same elements.

FIG. 7 is a diagram showing comparison between a base sequence (115 bp) at a middle portion of Tourist-OsaCatA (OsaCatA), and a corresponding region in a Tourist-OsaCatA like sequence in the vicinity of a putative protein coding region (CDS) whose expression was detected. Dots (•) indicate homology to the base sequence of Tourist-OsaCatA. Portions having no corresponding bases are indicated by gaps (–).

Figure 1:
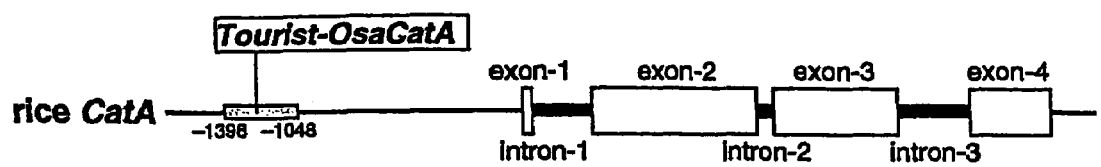
FIG. 1 is a schematic diagram showing Tourist-OsaCatA present in a promoter region in the rice catalase CatA gene.

DETAILED DESCRIPTION OF THE INVENTION (Simple Explanation of each Sequence)

SEQ ID NO: 1 indicates a representative key sequence according to the present invention.

SEQ ID NO: 2 indicates a preferable key sequence according to the present invention.

SEQ ID NOs: 3 to 14 indicate sequences which have been known as having a base sequence similar to Tourist.

SEQ ID NO: 3 indicates positions 4621 to 8640 of Accession No. X14172 (phy18) (amino acid coding regions (4626 . . . 6690, 6913 . . . 7729, 8011 . . . 8307, 8410 . . . 8617)).

SEQ ID NO: 4 indicates positions 26881 to 28560 of Accession No. U70541 (A1 gene) (amino acid coding regions (26910 . . . 27030, 27143 . . . 27507, 27894 . . . 28526)).

SEQ ID NO: 5 indicates positions 2761 to 5280 of Accession No. U72724 (XA21E gene) (amino acid coding regions (2819 . . . 5260)).

SEQ ID NO: 6 indicates positions 3301 to 10620 of Accession No. D10838 (sbe1) (amino acid coding regions (3360 . . . 3443, 3546 . . . 3608, 5821 . . . 6028, 6144 . . . 6213, 6648 . . . 6917, 7026 . . . 7932, 8245 . . . 8361, 8519 . . . 8581, 9019 . . . 9126, 9595 . . . 9696, 9862 . . . 9929, 10011 . . . 10091, 10210 . . . 10326, 10408 . . . 10612)).

SEQ ID NO: 7 indicates positions 421 to 1200 of Accession No. X57658 (OC-II gene) (amino acid coding regions (446 . . . 574, 983 . . . 1174)).

SEQ ID NO: 8 indicates positions 541 to 4080 of Accession No. M74177 (amy2A) (amino acid coding regions (581 . . . 661, 743 . . . 875, 2379 . . . 3199, 3744 . . . 4040)).

SEQ ID NO: 9 indicates positions 1981 to 6480 of Accession No. L28995 (HMGR gene) (amino acid coding regions (2018 . . . 2775, 4836 . . . 5017, 5631 . . . 5977, 6202 . . . 6444)).

SEQ ID NO: 10 indicates positions 1561 to 3840 of Accession No. D29966 (CatA) (amino acid coding regions (1591 . . . 1605, 1894 . . . 2694, 2781 . . . 3380, 3730 . . . 3789)).

SEQ ID NO: 11 indicates positions 1081 to 5340 of Accession No. X89226 (LRK2 gene) (amino acid coding regions (1126 . . . 3733, 4934 . . . 5298)).

SEQ ID NO: 12 indicates positions 1381 to 2040 of Accession No. X52422 (RAB16B gene) (amino acid coding regions (1396 . . . 1629, 1725 . . . 1985)).

SEQ ID NO: 13 indicates positions 1081 to 4740 of Accession No. Z15085 (GP28 gene) (amino acid coding regions (1094 . . . 1381, 2773 . . . 4735)).

SEQ ID NO: 14 indicates positions 901 to 2187 of Accession No. U72255 (GNS9 gene) (amino acid coding regions (956 . . . 1028, 1127 . . . 2187)).

SEQ ID NOs: 15 to 25 are base sequences containing protein coding regions (CDS) of genes which were confirmed in the present invention to be expressed in desired sites.

SEQ ID NO: 15 indicates positions 96961 to 98100 of Accession No. AB023482 (CDS3) (CDS regions (96980 . . . 97015, 97192 . . . 98055)).

SEQ ID NO: 16 indicates positions 55621 to 60600 of Accession No. AB026295 (CDS6) (CDS regions (55634 . . . 55706, 56057 . . . 56417, 57951 . . . 58143, 58542 . . . 59093, 59182 . . . 59328, 60209 . . . 60562)).

SEQ ID NO: 17 indicates positions 19141 to 22261 of Accession No. AJ243961 (CDS7) (CDS region (20178 . . . 21866)).

SEQ ID NO: 18 indicates positions 31201 to 33000 of Accession No. AJ243961 (CDS8) (CDS regions (complement (32825 . . . 32949), complement (30355 . . . 31213))).

SEQ ID NO: 19 indicates positions 13561 to 18600 of Accession No. AJ245900 (CDS9) (CDS regions (complement (18519 . . . 18594), complement (17735 . . . 17832), complement (17328 . . . 17361), complement (17012 . . . 17148), complement (16646 . . . 16712), complement (16324 . . . 16423), complement (15519 . . . 15682), complement (14988 . . . 15034), complement (14833 . . . 14880), complement (14081 . . . 14594), complement (13572 . . . 13582))).

SEQ ID NO: 20 indicates positions 47761 to 55560 of Accession No. AJ245900 (CDS10) (CDS regions (complement (55452 . . . 55548), complement (54532 . . . 55083), complement (54172 . . . 54276), complement (53484 . . . 53745), complement (51359 . . . 51407), complement (51193 . . . 51277), complement (50866 . . . 50958), complement (50465 . . . 50731), complement (48371 . . . 48894), complement (47810 . . . 48283))).

SEQ ID NO: 21 indicates positions 92341 to 97980 of Accession-No. AP000361 (CDS12) (CDS regions (complements (92382 . . . 92477, 92598 . . . 92649, 92771 . . . 92844, 92951 . . . 93001, 93081 . . . 93188, 93449 . . . 93550, 93734 . . . 93820, 94559 . . . 94601, 94689 . . . 94817, 94917 . . . 94994, 95080 . . . 95129, 95344 . . . 95520, 95872 . . . 95997, 96271 . . . 96384, 96876 . . . 96941, 97031 . . . 97096, 97723 . . . 97764, 97908 . . . 97928))).

SEQ ID NO: 22 indicates positions 7921 to 14160 of Accession No. AP000559 (CDS16) (CDS regions (7961 . . . 8199, 8666 . . . 8737, 8962 . . . 9033, 9134 . . . 9205, 9487 . . . 9558, 9770 . . . 9841, 9939 . . . 10010, 10098 . . . 10169, 10254 . . . 10322, 10440 . . . 10511, 10637 . . . 10708, 10792 . . . 10863, 10948 . . . 11019, 11102 . . . 11173, 11262 . . . 11333, 11448 . . . 11519, 11611 . . . 11682, 11795 . . . 11866, 11963 . . . 12034, 12124 . . . 12195, 12272 . . . 12353, 12398 . . . 12515, 12601 . . . 12732, 12838 . . . 13176, 13259 . . . 13629, 13761 . . . 14114)).

SEQ ID NO: 23 indicates positions 76801 to 78960 of Accession No. AP000559 (CDS17) (CDS region (complement (76828 . . . 78936))).

SEQ ID NO: 24 indicates positions 49981 to 53460 of Accession No. AP000570 (CDS23) (CDS region (50022 . . . 50087, 50181 . . . 50281, 50401 . . . 50558, 50707 . . . 50781, 51681 . . . 51820, 52437 . . . 52530, 53216 . . . 53424)).

SEQ ID NO: 25 indicates positions 95341 to 98220 of Accession No. AP000836 (CDS26) (CDS regions (complements (95361 . . . 95398, 95488 . . . 95556, 95925 . . . 96026, 97898 . . . 98003, 98148 . . . 98168))).

SEQ ID NOs: 26 to 37 indicates the sequences of corresponding regions in the Tourist-OsaCatA like sequence in the vicinity of a putative protein coding region (CDS) whose expression was detected at a desired site. SEQ ID NO: 26 (Osa#3) (homology to-OsaCatA: 82.6%); SEQ ID NO: 27 (Osa#6) (homology to-OsaCatA: 90.4%); SEQ ID NO: 28 (Osa#7) (homology to-OsaCatA: 73.5%); SEQ ID NO: 29 (Osa#8) (homology to-OsaCatA: 84.3%); SEQ ID NO: 30 (Osa#9) (homology to-OsaCatA: 65.8%); SEQ ID NO: 31

(Osa#10) (homology to-OsaCatA: 86.2%); SEQ ID NO: 32
(Osa#12) (homology to-OsaCatA: 77.4%); SEQ ID NO: 33
(Osa#16) (homology to-OsaCatA: 85.2%); SEQ ID NO: 34
(Osa#17) (homology to-OsaCatA: 81.9%); SEQ ID NO: 35
(Osa#18) (homology to-OsaCatA: 87.8%); SEQ ID NO: 36
(Osa#24) (homology to-OsaCatA: 89.6%); SEQ ID NO: 37
(Osa#29) (homology to-OsaCatA: 90.4%).

Hereinafter, the present invention will be described.

It should be understood throughout the present specification that articles for singular forms (e.g., "a", "an", "the", etc. in English; "ein", "der", "das", "die", etc. and their inflections in German; "un", "une", "le", "la", etc. in French; and articles, adjectives, etc. in other languages) include the concept of their plurality unless other wise mentioned. It should be also understood that terms as used herein have definitions ordinarily. used in the art unless otherwise mentioned.

(Best Mode for Carrying out the Invention)

As used herein, "transposon" or "transposon sequence" refers to a DNA sequence having a predetermined structure which can undergo transposition on a chromosomal DNA. Transposons are ubiquitous in bacteria, yeast, maize, *Drosophila*, and the like. Transposition sites are not constant. Transposons are transferred to any genes. When a transposon is inserted in the vicinity of a gene, the transposon may have an influence on expression of the gene. When a transposon is inserted within a gene, the gene may be inactivated.

As used herein, "MITE (miniature inverted-repeat transposable element)" or MITE sequence refers to a transposable element having a small size (typically, 0.5 kb or less) which are scattered on a chromosomal DNA and has a terminal inverted repeat.

To date, genetic elements (transposable elements), which are transposable on the same DNA in a chromosome or between DNAs in different chromosomes, have been found in various organisms (Finnegan, 1989; Flavell et al., 1994; Bennetzen, 2000). The transposable elements are classified into two classes according to their transposition mechanism. Class I elements undergo transposition through reverse transcription of RNA transcription intermediates. Class II elements undergo transposition directly from DNA to DNA (Finnegan, 1989). A transposable element of a novel class called MITE has been reported in a plant for the first time (Zhang et al., 2000 and references cited therein). MITE has a structure typical to DNA transposable elements, but does not code a transposase essential for transposition (Bennetzen, 2000). MITE tends to be present in the vicinity of a gene (Mao et al., 2000 and references cited therein), and is a transposable element which was most frequently found in the base sequence of a rice genome of 910 kb (Turcotte et al., 2001).

As used herein, "Tourist" sequence or "Tourists" element, which are interchangeably used, refers to a base sequence (element) which undergoes transposition on a chromosomal DNA, or which is considered to be produced by transposition. A Tourist sequence is a type of MITE sequence, and was originally identified in the Waxy (wx) gene of maize (*Zea mays*). The Tourist sequences are characterized by terminal inverted repeat, small size, the tendency of the base sequence of an insertion site, and stable DNA secondary structure (Bureau and Wessler, 1992). The Tourist sequences are classified into four subfamilies (Tourist-A, B, C and D) according to their internal base sequence (Bureau and Wessler, 1994). Tourist-A element is found in maize, Tourist-B in sorghum (*Sorghum bicolor*), Tourist-C in rice (*Oryza sativa*) and sorghum, and Tourist-D in maize and barley (*Hordeum vulgare*).

The Tourist-A is characterized by having a repeated sequence consisting of GGATT. Tourist-B is characterized by having box I, domain I, and a subterminal polyA/polyT region. Tourist-C is characterized by having box I, domain I and I', and a subterminal polyA/polyT region. Tourist-D is characterized in that no conserved region is contained in the internal base sequence.

If Tourist was inserted in the vicinity of a gene, which is to be expressed in a flower, before speciation into cereal, such as rice, maize, and sorghum, there is a possibility that a Tourist-like sequence is found in the vicinity of a gene, which is to be expressed at a specific site (e.g., a flower), in the case of maize, sorghum, and the like other than rice. It can be easily understood by those skilled in the art that the base sequence of a portion of Tourist used for detection varies depending on the purpose. The base sequence of another portion of Tourist may have been suitable for detection in terms of other specific purposes since the speciation of Tourist into types A, B, C and D.

Alternatively, it can be contemplated that Tourist sequence has been gradually mutated into Tourist-A, B, C, or D with the speciation into rice, maize, sorghum, and the like, and thereafter, Tourist-A, B, C, or D separately underwent transposition in the respective plant variety to be inserted in the vicinity of a gene. Therefore, Tourist-A, B or D may also be utilized for detection of genes which are to be expressed in a specific organ. Specifically, since a long time has passed since the speciation of cereal, Tourist-A, B, C or D can be distinguished from each other. By using a certain portion of these base sequences, genes which are to be expressed in a specific organ can be detected.

In the present invention, preferably, the Tourist-C sequence (also referred to as the Tourist-C element) is particularly used. The tourist-C sequence is characterized by having box I, domains I and I', and subterminal polyA/polyT regions. Domain I' has a sequence similar to that of the complementary strand of domain I (Bureau and Wessler, 1992). It is known that the Tourist elements are found in introns of genes or regions in the vicinity of genes (Bureau and Wessler, 1992, 1994; Bureau et al., 1996). It is therefore believed that the Tourist elements are inserted dominantly in the vicinity of protein coding regions in a genome.

More preferably, the Tourist-C sequence of the present invention may be here in the Tourist-OsaCatA sequence. The Tourist-OsaCatA is a Tourist element present in the 5'-upstream region of the CatA gene (Iwamoto et al., 1999), which has been found by comparing the base sequence of one of the rice catalase genes, the CatA gene (Higo and Higo, 1996) with various types of rice of the genus *Oryza*. Therefore, in one embodiment, Tourist-OsaCatA may be used for the purpose of finding "conserved base sequences" suitable for phylogenetic analysis among a number of types of rice of the genus *Oryza*.

The inventors of the present invention fused a 5'-upstream promoter region of the rice catalase CatA gene (Higo and Higo, Plant Mol. Biol. 30: 505-521 (1996)) with a reporter gene (GUS), and introduced the resultant gene into rice. Tissue of the transformed plant was stained. As a result, it was found that the reporter gene was strongly expressed in the anther and pollen. Thus, the inventors revealed that the promoter can be utilized so as to prepare a promoter cassette for expression of a useful gene in an anther or pollen for the aim to produce male sterility strains or the like (International Publication WO 00/58454 published on Oct. 5, 2000). In the CatA promoter region, there is a base sequence (about 300 bases) which is a transposable element and belongs to a group called Tourist sequence (present at positions 164 to 515 of the base sequence of the above-described patent application; designated as Tourist-OsaCatA) (Iwamoto et al. Mol. Gen. Genet. 262: 493-500 (1999)) (FIG. 1).

However, to the present inventors' knowledge, prior to the disclosure of the present invention there has been no report indicating that a transposon sequence (e.g., a MITE sequence, such as Tourist sequence) is successfully used as an indicator to detect a gene which is to be expressed in a desired organ.

In a seed plant, such as rice, even if a transposon, such as Tourist, undergoes transposition into a chromosome, the transposon is not passed to progeny unless the chromosome is of a germ cell. Therefore, it is difficult to imagine that a transposon can be used as an indicator to detect a gene which is to be expressed in a desired organ.

The present inventors discovered that a transposon, such as Tourist, which is present in a cell at a site containing a flower, can be passed to progeny and expressed in a specific organ.

Therefore, since it was not believed based on the findings as of the disclosure of the present invention regarding a transposon sequence (e.g., a MITE sequence, such as a Tourist sequence) that the transposon sequence is related to an expression specific site, the present invention has an advantageous effect, which is not otherwise predictable, over conventional findings.

According to the present invention, a transposon sequence (e.g., A MITE sequence, such as a Tourist sequence) can be utilized in organs other than a genital organ in a plant. This is because an inserted transposon may be passed to progeny through a non-genital organ in the case of plants which undergo vegetative reproduction (e.g., plants reproduced through underground stems: iris (rhizome), arrowhead (corm), saffron (corm), potato (tuber), dahlia (tuber), lily (bulb), onion (bulb), bracken (underground stem), lotus (underground stem); roots: sweet potato (tuberous root); bulbil: yam (bulbil), garlic (bulbil); branches: strawberry (runner)). Therefore, it will be clearly understood by those skilled in the art that even in the case of transposition in a root, a stem, and a leaf other than a flower, a gene whose expression is specific to an organ, such as a root, a stem, and a leaf, can be detected using a transposon sequence as a key.

As used herein, "key" sequence refers to a sequence which is used in a gene search in accordance with the present invention. The key sequence may be electronic data for use in a computer, i.e., a "query" sequence, or a biological probe for in vitro and/or in vivo screening, i.e., a "probe" sequence. As used herein, "query" sequence refers to a sequence for use in gene search by a computer, including the base sequence of DNA or RNA or the amino acid sequence of a protein for which a database is searched. "Probe sequence" refers to a sequence for use in a biological experiment, such as in vitro and/or in vivo screening.

As used herein, "gene population" includes, but is not limited to, a nonredundant population of gene data items, which are mutually related, in the form of electronic data, i.e., a "database", and a biological population, i.e., a "library". A "database" refers to a nonredundant group of gene data items which are mutually related, including electronic data. The database may be a DNA database or a protein database. Preferably, the database may be a DNA database or the like. As used herein, "library" refers to a group of genes for use in biological screening, which are mutually related. The library may be a DNA library or an RNA library, or a protein library. A DNA library is preferable.

As used herein, "search" refers to utilizing a certain nucleic acid base sequence in an electronic or biological manner or the like to find another nucleic acid base sequence. Examples of the electronic search includes, but are not limited to, BLAST (Altschul et al., J. Mol. Biol. 215: 403-410 (1990)), FASTA (Pearson & Lipman, Proc. Natl. Acad. Sci., USA 85: 2444-2448 (1988)), Smith and Waterman method (Smith and Waterman, J. Mol. Biol. 147: 195-197 (1981)), and Needleman and Wunsch method (Needleman and Wunsch, J. Mol. Biol. 48: 443-453 (1970)), and the like. Examples of the biological search include stringent hybridization, macroassay in which genome DNA is attached to nylon membrane or the like, microassay in which genome DNA is attached to a glass plate (microarray assay), PCR and in situ hybridization.

As used herein, "comparative selection" of sequences refers to comparing two sequences in an electronic or biological manner or the like with respect to a certain nucleic acid base sequence (e.g., in the case of electronic comparative selection, two sequences are aligned so as to determine a difference every unit sequence so that a desired sequence is selected. Methods similar to those used in the above-described search may be applied to the comparative selection of sequences. In an electronic search for a sequence, a query sequence is compared with a large number of base sequences in a database so as to find the closest sequence. On the other hand, in a biological experiment (hybridization or the like), a sequence having the highest complementarity strongly binds to a probe. The binding corresponds to comparative selection. The comparative selection is also herein simply referred to as "selection".

As used herein, "stringent conditions" for hybridization refer to conditions under which the complementary strand of a nucleotide strand having homology to a target sequence predominantly hybridizes with the target sequence, and the complementary strand of a nucleotide strand having no homology substantially does not hybridize. "Complementary strand" of a certain nucleic acid sequence refers to a nucleic acid sequence paired with the certain nucleic acid sequence by hydrogen bonds between nucleic acid bases (e.g., T for A and C for G). The stringent conditions are sequence-dependent, and vary depending on various circumstances. The longer the sequence, the higher temperature the sequence specifically hybridizes at. In general, as for the stringent conditions, the temperature is selected about 5° C. lower than the melting point (Tm) of a particular sequence at a predetermined ionic strength and pH. Tm is the temperature at which 50% of nucleotides complementary to a target sequence hybridize to the target sequence in an equilibrium state under a predetermined ionic strength, pH, and nucleic acid concentration. "Stringent conditions" are sequence-dependent and vary depending on various environmental parameters. The stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

Microarray assay is a technology well known to those skilled in the art, and is described in detail in DeRisi et al., Science 278: 680-686 (1997); Chu et al., Science 282: 699-705 (1998).

As used herein, "gene" refers to a functional unit of heredity, which typically occupies a specific site (locus) on a chromosome. In general, a gene can reproduce itself with accuracy in cell division, and control synthesis of protein, such as an enzyme. A gene as a functional unit is made of discontinuous segments of a DNA macromolecule. The DNA molecule contains a proper sequence of bases (A, T, G and C) coding a specific peptide (amino acid sequence). Genetic information is typically described by DNA and sometimes RNA. As described above, a gene is typically present within a chromosome, and all chromosomes are arranged in a pair, except for a human male sex chromosome (X and Y), for example. Genes are typically present in a pair in any cell other than a gamete. A gene typically contains a region coding a protein (exons) and, in addition, introns present between exons, an expression control region (promoter region) upstream of a first exon, and a region downstream of the protein coding region.

As used herein, "structural gene" refers to a portion of a gene other than a promoter and an intron of the gene, which determines directly the primary structure of a polypeptide in accordance with a genetic code.

As used herein, "homology" or "similarity" of a gene or a sequence, which are interchangeably used, refers to the magnitude of identity between two or more gene sequences. The magnitude of homology is herein determined by Blast using its default parameters. Therefore, the greater the homology between two genes, the greater the identity or similarity between their sequences. Whether or not two genes have homology is determined by comparing their sequences directly or by a hybridization method under stringent conditions. When two gene sequences are directly compared with each other, the genes have homology if representatively at least 50%, preferably at least 70%, more preferably at least 80%, 90%, 95%, 96%, 97%, 98%, or 99% of the DNA sequence of the genes are identical.

As used herein, "site containing a flower" refers to any site of a plant containing a flower. Therefore, the site containing a flower may contain a plant organ other than a flower (e.g., lemma, palea, glume, rudimentary glume, and rachilla).

As used herein, "flower" is a reproductive structure characteristic to a seed plant, and has a vivid color in its part or entirety. For example, the flower of rice consists of glumose flowers, a stamen, a pistil and a base.

As used herein, "stamen" refers to a male genital organ consisting of an anther and a filament, and "pistil" refers to a female genital organ consisting of a stigma, a style, and an ovary.

As used herein, "express at a site containing a flower" indicates that expression is performed only at a flower and, in addition, that expression is performed at a flower and other organs (tissue).

According to another aspect of the present invention, a method is provided for obtaining information about a certain gene regarding the presence or absence of a base sequence similar to a transposable element sequence so as to infer that the gene may be expressed in a specific plant organ or site associated with the transposable element sequence.

In the method of the present invention, by utilizing the base sequence of a transposable element (e.g., a certain transposable element is commonly present in the vicinity of several genes which are expressed in a root) which is specific to an organ (e.g., organs containing a blade, a leaf sheath and a root, and the like) other than a flower of a plant (e.g., monocotyledon (e.g., rice)), vast base sequence data about the genome of rice can be screened for a gene which is to be expressed in a root.

Conventionally, a base sequence motif in a promoter sequence of a gene, to which a transcription regulatory element binds, has been studied so as to find a clue for such a search. Such a short motif brings noise to a search. Therefore, the use of such a motif is practically impossible or very difficult. "Noise" in a search refers to a motif sequence which has the same base sequence as that of a known short motif, but does not actually function, since the motif sequence is not located at an appropriate position with respect to a transcription initiation point, or the like. In currently available motif databases and analysis tools, a search is performed simply with reference to the presence or absence of matching of short base sequences. The noise has not been reduced to a negligible level. Therefore, when a short sequence which is the same as a known motif is found on a certain DNA base sequence, the short sequence is suggested to be potentially a functioning motif, but at the same time is highly likely to be mere noise, leading to poor search efficiency. The present invention is provided so as to solve this problem. It is not until a transposable element having a size of about 100 to 300 bases is employed in the present invention that the noise can be reduced so that a gene, which is specifically expressed at a specific site, can be searched for.

The present invention also provides genes found by the above-described method of the present invention. Therefore, these genes are expressed at a site containing a flower.

The present invention also provides a method for modifying transcription of a plant using information about the genes found in the above-described method of the present invention. The modification maybe easily carried out using molecular biological and/or biochemical technologies commonly used in the art.

Figure 8:
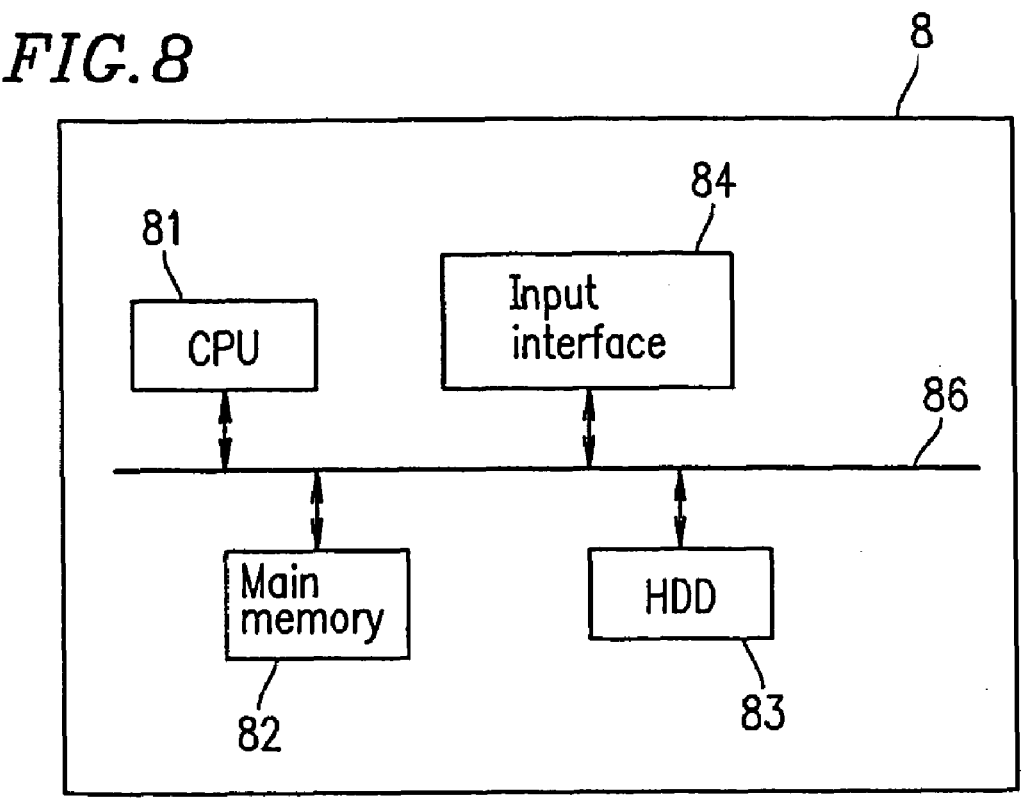
FIG. 8 is a diagram showing an exemplary computer system for carrying out the present invention.

FIG. 8 shows an exemplary configuration of a computer 8 according to the present invention for carrying out the method of the present invention. The computer 8 comprises a CPU 81, a main memory 82, a hard disk drive (HDD) 83, and an input interface 84. These components 81 to 84 are, for example, interconnected through a bus 86. Any type of memory may be used instead of the HDD 83.

The HDD 83 stores a program representing automatic computation (hereinafter referred to as automatic computation program) in advance. Alternatively, an automatic computation program may be recorded onto any type of computer readable recording medium, such as a floppy disk, a CD-ROM, a CD-R, and a DVD-ROM. The automatic computation program stored in such a recording medium is loaded into the HDD 83 via an input apparatus (e.g., a disk drive).

The CPU 81 executes the automatic computation program stored in the HDD 83. The execution of the automatic computation program by the CPU 81 allows the computer 8 to function as an automatic computation apparatus according to the present invention.

An input device (e.g., a keyboard and a mouse) and the like may be connected to the input interface 84. The input device may be used so as to input data required by the computer 8.

A portion of the automatic computation program or a portion of data is optionally transferred to the main memory 82. The CPU 81 can access the main memory 82 at high speed.

A query sequence and/or a database for use in the present invention may be input into the computer 8 using, for example, an input device, and stored in the HDD 83 as a master file. The query sequence and/or the database may also be input via a network (e.g., the Internet) to the computer 8. A result of a search may be optionally output via an output interface (not shown). A display, a storage apparatus, or the like maybe connected to the output interface, for example. The search result may be stored in the HDD 83. The search result may be optionally recorded onto the above-described computer readable recording medium.

According to one aspect of the present invention, a method for detecting a gene at a desired site in a plant, comprises the step of:

(1) searching a gene population using a transposon sequence as a key sequence.

The method further comprises the step of:

(2) selecting a gene having similarity to the transposon sequence in the vicinity of a putative protein coding region.

The transposon sequence may be a MITE sequence. Preferably, the transposon sequence maybe a Tourist sequence. Examples of the Tourist sequence include Tourist-A, B, C or D. Preferably, the transposon sequence is the Tourist-C sequence. More preferably, the Tourist sequence may be Tourist-OsaCatA (SEQ ID NO: 1). Even more preferably, the Tourist sequence may be a 115 bp sequence (SEQ ID NO: 2) of positions 109 to 223 of Tourist-OsaCatA.

The transposon sequence of the present invention (e.g., a MITE sequence, such as a Tourist sequence) may contain at least contiguous nucleotide sequence of about 10, about 15, about 20, about 25, about 30, about 35, about 40, about 45, about 50, about 75, about 100, about 115, about 125, about 150, about 200, about 250, or about 300 in a sequence indicated by SEQ ID NO: 1 or 2. In one embodiment, the above-described transposon sequence (e.g., a MITE sequence, such as a Tourist sequence) may contain a sequence having at least about 70%, about 80%, about 90%, about 95%, or about 99% homology to the sequence indicated by SEQ ID NO: 1 or 2. In another embodiment, the above-described Tourist sequence may have at least one substitution, addition or deletion in the sequence indicated by SEQ ID NO: 1 as long as the function of the present invention can be maintained. In another embodiment, the above-described Tourist sequence may have at least one substitution, addition or deletion in the sequence indicated by SEQ ID NO: 2 as long as the function of the present invention can be maintained. The above-described transposon sequence may have one or several substitutions, additions or deletions. More preferably, the above-described transposon sequence may be substantially or fully the same as the sequence indicated by SEQ ID NO: 1. In another preferred embodiment, the above-described transposon sequence may be substantially or fully the same as the sequence indicated by SEQ ID NO: 2.

In another embodiment of the present invention, the above-described desired site may be a site containing a flower. The site containing a flower may be a flower. Preferably, the site containing a flower may contain at least one site selected from a stamen and a pistil. In another embodiment, examples of the site containing a flower include lemma, palea, glume, rudimentary glume, rachilla, and lodicule. In still another embodiment, the plant may be monocotyledon. Preferably, the plant may be rice.

In another embodiment, the above-described database may be a DNA database. More particularly, examples of the database include BBDJ, EMBL, and GenBank. When a biological technique is used, the above-described database may be a DNA library.

In one embodiment of the present invention, examples of the search method for use in search include BLAST, FASTA, Smith and Waterman method, and Needleman and Wunsch method. In another embodiment of the present invention, examples of the search method for use in search include stringent hybridization, microarray assay, PCR, and in situ hybridization.

In one embodiment of the present invention, the above-described vicinity of a putative protein coding region may be within about 2 kbp upstream of the translation initiation codon, within about 1.1 kbp downstream of the translation termination codon, and within the intron.

In one embodiment of the present invention, the above-described similarity is at least about 66% homology. The similarity may be at least about 70%, at least about 75%, at least about 80%, at least about 85%, at least about 90%, at least about 95%, at least about 99% homology or the like.

In another aspect of the present invention, the present invention provides a composition for detecting a gene which is to be expressed at a site containing a flower, comprising a plasmid containing at least about 10 contiguous nucleotides in the sequence indicated by SEQ ID NO: 1. The nucleotides contained in the plasmid may be the transposon sequence of the present invention (e.g., a MITE sequence, such as a Tourist sequence), which may contain at least contiguous nucleotide sequence of about 15, about 20, about 25, about 30, about 35, about 40, about 45, about 50, about 75, about 100, about 115, about 125, about 150, about 200, about 250, or about 300 in the sequence indicated by SEQ ID NO: 1 or 2. In one embodiment, the above-described MITE sequence or transposon sequence may contain a sequence having at least about 70%, about 80%, about 90%, about 95%, or about 99% homology to the sequence indicated by SEQ ID NO: 1 or 2. In another embodiment, the above-described transposon sequence may have at least one substitution, addition or deletion in the sequence indicated by SEQ ID NO: 1 as long as the function of the present invention can be maintained. In another embodiment, the above-described transposon sequence may have at least one substitution, addition or deletion in the sequence indicated by SEQ ID NO: 2 as long as the function of the present invention can be maintained. The above-described transposon sequence may have one or several substitutions, additions or deletions. More preferably, the above-described transposon sequence may be substantially or fully the same as the sequence indicated by SEQ ID NO: 1. In another preferred embodiment, the above-described transposon sequence may be substantially or fully the same as the sequence indicated by SEQ ID NO: 2.

In another aspect of the present invention, the present invention provides a kit for detecting a gene which is to be expressed at a desired site in a plant. The kit comprises:

(1) a plasmid containing at least about 10 contiguous nucleotides in the sequence indicated by SEQ ID NO: 1; and (2) a DNA library.

In the method, the plasmid and the DNA library are defined as above.

In another aspect, the present invention provides a method for producing a gene which is to be expressed at a desired site in a plant. The method comprises the steps of:

(1) searching a gene population (e.g., a database) for a transposon sequence (e.g., a MITE sequence, such as a Tourist sequence) as a key sequence;

(2) selecting a gene having similarity to the above-described transposon sequence in a putative promoter region; and (3) producing a nucleic acid molecule coding the above-described gene.

In this method, steps (1) and (2) are the same as those described above. A method for producing a nucleic acid molecule coding a gene is well known in the art as described, for example, in Sambrook et al., Molecular Cloning: A Laboratory Manual (2nd Ed.), Vol. 1 to 3, Cold Spring Harbor Laboratory, (1989) or Current Protocols in Molecular Biology, F. Ausubel et al Ed., Greene Publishing and Wiley-Interscience, New York (1987). Preferably, the above-described production may be carried out in vitro or in vivo.

In another aspect., the present invention provides a recording medium storing a program for allowing a computer to execute automatic computation for detecting a gene which is to be expressed at a desired site in a plant. The automatic computation comprises the steps of:

(1) providing a transposon sequence (e.g., a MITE sequence, such as a Tourist sequence) as a query sequence;
(2) providing a database;
(3) searching the database using the query sequence; and
(4) outputting a result of the search.

The description about the search in steps (1) to (4) is the same as that which is described above. Techniques relating to the automatic computation are well known in the art and herein described above.

In another aspect, the present invention provides a program for allowing a computer to execute automatic computation for detecting a gene which is to be expressed at a desired site in a plant. The automatic computation comprises the steps of:

(1) providing a transposon sequence (e.g., a MITE sequence, such as a Tourist sequence) as a query sequence;
(2) providing a database;
(3) searching the database using the query sequence; and
(4) outputting a result of the search.

The description about the search in steps (1) to (4) is the same as that which is described above. Techniques relating to the automatic computation are well known in the art and herein described above.

As used herein, information processing refers to calculation or process of information according to the purpose of use, and software refers to a program relating to operations of a computer. A program refers to an ordinal sequence of instructions suitable for processing by a computer. The program is a product. A program list refers to presentation per se of a program by printing the program onto paper, displaying the program on a screen, or the like. A computer readable recording medium storing a program refers to a computer readable recording medium storing a program for use in installing, executing, distributing, and the like, the program.

Procedure refers to a series of processes or operations which are linked in a time-series manner in order to achieve a predetermined purpose.

Data structure refers to a logical structure of data represented by relationships among elements. Hardware resource refers to a physical apparatus or a physical element which is used for embodying a process, an operation or a function.

The hardware resource refers to, for example, as a physical apparatus, a computer and its components (i.e., a CPU, a memory, an input apparatus, and an output apparatus), or a physical apparatus connected thereto.

In another aspect, the present invention provides a system for detecting a gene which is to be expressed at a desired site in a plant. The system comprises:

(A) a computer; and
(B) a program for allowing a computer to execute automatic computation for detecting a gene which is to be expressed at a desired site in a plant.

The automatic computation comprising the steps of:

(1) providing a transposon sequence (e.g., a MITE sequence, such as a Tourist sequence) as a query sequence;
(2) providing a database;
(3) searching the database using the query sequence; and
(4) outputting a result of the search.

The description about the search in steps (1) to (4) is the same as that which is described above. Techniques relating to the automatic computation and the computer system are well known in the art and herein described above.

In one embodiment, the above-described computer is linked to a network. The network may be preferably the Internet.

In another aspect, the present invention provides a method for inferring an organ of a plant in which a gene is to be expressed. The method comprises the step of:

(1) obtaining information about whether or not abase sequence similar to the sequence of a transposable element is present in the vicinity of the gene, and when the similar sequence is present in the vicinity of the gene, inferring that the gene is to be expressed in a plant organ relating to the transposable element sequence.

As used herein, "transposable element sequence" refers to a base sequence which undergoes transposition on a chromosomal DNA or which seems to be generated by transposition. Preferably, examples of the transposable element sequence include Ac/Ds of maize and Tos17 of rice.

In one embodiment, the plant organ relating to the transposable element sequence is a site containing a flower. In another embodiment, the site containing a flower contains a site selected from the group consisting of a stamen and a pistil. In one embodiment, the sequence similar to the transposable element sequence is a transposon sequence (e.g., a MITE sequence, such as a Tourist sequence), which may contain at least contiguous nucleotide sequence of about 15, about 20, about 25, about 30, about 35, about 40, about 45, about 50, about 75, about 100, about 115, about 125, about 150, about 200, about 250, or about 300 in the sequence indicated by SEQ ID NO: 1 or 2. In one embodiment, the transposon sequence may contain a sequence having at least about 70%, about 80%, about 90%, about 95%, or about 99% homology to the sequence indicated by SEQ ID NO: 1 or 2. In another embodiment, the above-described transposon sequence may have at least one substitution, addition or deletion in the sequence indicated by SEQ ID NO: 1 as long as the function of the present invention can be maintained. In another embodiment, the above-described transposon sequence may have at least one substitution, addition or deletion in the sequence indicated by SEQ ID NO: 2 as long as the function of the present invention can be maintained. The above-described transposon sequence may have one or several substitutions, additions or deletions. More preferably, the above-described transposon sequence may be substantially or fully the same as the sequence indicated by SEQ ID NO: 1. In another preferred embodiment, the above-described transposon sequence may be substantially or fully the same as the sequence indicated by SEQ ID NO: 2.

In another embodiment, the plant includes rice.

In another embodiment, the present invention provides a nucleic acid molecule coding a gene obtained by the method of the present invention. A method for producing this nucleic acid molecule is well known to those skilled in the art, and described in another portion of the present specification or Sambrook et al. (supra).

In one embodiment, the present invention provides a nucleic acid molecule coding a gene which is to be expressed at a desired site in a plant. The base sequence of the nucleic acid molecule is obtained by a method comprising the step of:

(1) searching a gene population using a transposon sequence (e.g., a MITE sequence, such as a Tourist sequence) as a key sequence.

In another aspect, the present invention also provides a recording medium storing a sequence coding a gene obtained by the method of the present invention. Examples of the recording medium include a flexible disk, a hard disk, a CD-ROM, a CD-R, a CD-RW, a DVD-ROM, a tape, an MD or those which are described above.

In another embodiment, the present invention provides a method for modifying an expression pattern of a gene of a plant, comprising the step of utilizing the sequence of a gene obtained by the method of the present invention.

In another aspect, the present invention provides a kit for inferring a plant organ in which a gene is to be expressed. The kit comprises:

(1) a molecule having a transposable element sequence.

The transposable element sequence is briefly described above. The molecule may be a nucleic acid (DNA or RNA), or a derivative thereof. The derivative of the nucleic acid is well known in the art.

In still another embodiment, the present invention provides a kit for inferring a plant organ in which a gene is to be expressed. The kit comprises:

(1) a recording medium storing a transposable element sequence.

The transposable element sequence is briefly described. The recording medium is described in detail in another portion of the present specification.

"Derivative" nucleotide refers to a nucleotide containing a derivative of a nucleotide, or having a linkage with another nucleotide which is different from a typical linkage. Specific examples of such a nucleotide include a derivative nucleotide with a phosphorothioate bond converted from a phosphodiester bond in the original nucleotide, a derivative nucleotide with a N3'-P5' phosphoroamidate bond converted from a phosphodiester bond in the original nucleotide, a derivative nucleotide with peptide nucleic acids converted from a ribose and a phosphodiester bond in the original nucleotide, a derivative nucleotide with a uracil in the original nucleotide substituted with a C-5 propynyl uracil, a derivative oligonucleotide with a uracil in the original nucleotide substituted with a C-5 thiazole uracil, a derivative nucleotide with a cytosine in the original nucleotide substituted with a C-5 propynyl cytosine, a derivative oligonucleotide with a cytosine in the original nucleotide substituted with a phenoxazine-modified cytosine, a derivative nucleotide with a ribose in a DNA substituted with a 2'-O-propyl ribose, and a derivative nucleotide with a ribose in the original nucleotide substituted with a 2'-methoxyethoxy ribose.

In another embodiment, the present invention provides a recording medium storing a program for allowing a computer to execute automatic computation for inferring a plant organ in which a gene is to be expressed. The automatic computation comprises the steps of:

(1) providing a transposable element sequence as a query sequence;

(2) providing a sequence of the gene;

(3) comparing the query sequence with the sequence of the gene; and (4) outputting a result of the comparison.

The description about the search in steps (1) to (4) is the same as that which is described above. Techniques relating to the automatic computation are well known in the art and herein described above.

In another embodiment, the present invention provides a program for allowing a computer to execute automatic computation for inferring a plant organ in which a gene is to be expressed. The automatic computation comprises the steps of:

(1) providing a transposable element sequence as a query sequence;

(2) providing a sequence of the gene;

(3) comparing the query sequence with the sequence of the gene; and (4) outputting a result of the comparison.

Techniques relating to the automatic computation and the computer system are well known in the art and herein described above.

In another embodiment, the present invention provides a system for inferring a plant organ in which a gene is to be expressed. The system comprises:

(A) a computer; and (B) a program for allowing the computer to execute automatic computation for inferring a plant organ in which a gene is to be expressed. The automatic computation comprises the steps of:

(1) providing a transposable element sequence as a query sequence;

(2) providing a sequence of the gene;

(3) comparing the query sequence with the sequence of the gene; and (4) outputting a result of the comparison.

The description about the search in steps (1) to (4) is the same as that which described above. Techniques relating to the automatic computation and the computer system are well known in the art and herein described above. Preferably, the computer is linked to a network.

Examples of the gene identified by the method of the present invention, which is to be expressed in a site containing a flower, are described below.

Among genes which have been to date isolated from rice, there are 12 genes, including CatA (Kay et al., Nucl. Acids Res. 17, 2865-2866 (1989); Yamaguchi-Shinozaki et al., Plant Mol. Biol. 14: 29-39 (1989); Kondo et al., J. Biol. Chem. 265, 15832-15837 (1991); Huang et al., Gene, 111, 223-228 (1992); Kawasaki et al., Mol. Gen. Genet. 237, 10-16 (1993); Minami and Tanaka, Biochim. Biophys. Acta 1171: 321-322 (1993); Nelson et al., Plant Mol. Biol. 25, 401-412 (1994); Chen and Bennetzen, Plant Mol. Biol. 32, 999-1001 (1996); Higo and Higo, Plant Mol. Biol. 30, 505-521 (1996); Song et al., Plant Cell, 9, 1279-1287 (1997); GenBank accession number U72255; GenBank accession number X89226), in the vicinity of which base sequences similar to Tourist-OsaCatA were found (Bureau et al. Proc. Natl. Acad. Sci. USA, 93: 8524-8529 (1996); Iwamoto et al., Mol. Gen. Genet. 262: 493-500 (1999)). These sequences are respectively indicated by SEQ ID NOs: 3 to 14. The present invention is the first to find that these genes, except for CatA and HMGR, are expressed in a site containing a flower. Therefore, the present invention also provides nucleic acid molecules containing these sequences, which are expressed in a site containing a flower.

Figure 2:
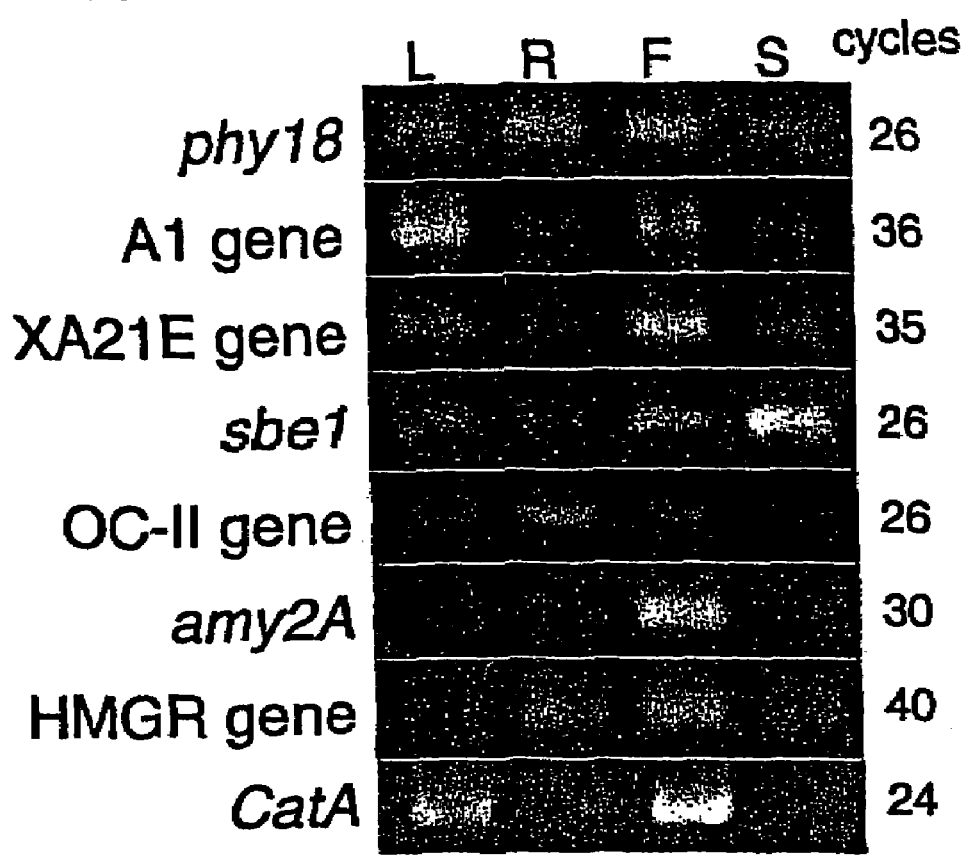
FIG. 2 is a diagram showing a result of analysis (RT-PCR) for expression of a known gene in the vicinity of Tourist-OsaCatA. In the figure, phy18 indicates phytochrome 18 gene (Kay et al., 1989); A1 gene indicates a putative NADPH-dependent reductase A1 gene (Chen and Bennetzen, 1996); XA21E gene indicates Xa21 family member E (Song et al., 1997); sbe1 indicates 1,4-α-glucan branching enzyme gene (Kawasaki et al., 1993); OCII gene indicates Oryzacystatin II gene (Kondo et al., 1991); amy2A indicates α amylase gene (Huang et al., 1992); HMGR gene indicates 3-hydroxy-3-methylglutaryl coenzyme A reductase gene (Nelson et al., 1994); and CatA indicates catalase CatA gene (Higo and Higo, 1996). Cycles indicate the number of PCR cycles. L indicates a leaf, R indicates a root, F indicates a flower, and S indicates an immature seed.

Expression of these genes in a flower, a root, a leaf, and an immature seed was analyzed with RT-PCR. As a result, expression of 8 genes was confirmed, all of which were expressed in the flower (FIG. 2). The inventors' research was the first to find expression in a flower of these genes other than CatA and HMGR. Therefore, it was demonstrated that the usefulness of the present invention was difficult to predict based on the conventional state of the art.

Figure 3:
FIG. 3 is a diagram showing a result of analysis (RT-PCR) for expression of a gene corresponding to EST in the vicinity of Tourist-OsaCatA. The same symbols as those in FIG. 2 indicate the same elements.

The inventors carried out a further search to find three similar sequences to Tourist-OsaCatA among the DNA base sequences which had been registered as EST (Iwamoto et al., Mol. Gen. Genet. 262: 493-500 (1999)). RT-PCR analysis confirmed that two of them were expressed in a flower (FIG. 3).

Further, a similarity search (BLAST) was carried out in a DNA database using the Tourist-OsaCatA base sequence as a query. As a result, 32 highly similar sequences were detected in the vicinity of 30 regions (CDS) which were inferred to code a gene in a BAC/PAC clone (Table 1). Of the 30 CDSs, 29 CDSs had the same size a PCR product using a genomic DNA as that which was expected. The 29 CDSs were investigated with RT-PCR for the presence or absence of expression of each gene in a blade, a root, a flower, and an immature gene (Table 2). As a result, for 11 CDSs, a product having the same size as that which was expected was observed. The expression of all CDSs were confirmed only in a flower, or in a flower and other organs (FIG. 4).

TABLE 1

Tourist-OsaCatA like base sequences detected in BAC/PAC clone

| Tourist | Size (bp) | Accession No. | Location[a] | Insertion site[b] |
|---|---|---|---|---|
| Osa#1 | 333 | AB023482 | 22909 ... 23241 | 5'F(873) |
| Osa#2 | 325 | AB023482 | 83129 ... 83453 | 5'F(2308) |
| Osa#3 | 345 | AB023482 | 95093 ... 95440 | 5'F(1540) |
| Osa#4 | 339 | AB023482 | 117761 ... 117423C | 5'F(840), 5'F(1516) |
| Osa#5 | 342 | AB023482 | 145798 ... 146139 | 3'F(445), 5'F(763) |
| Osa#6 | 319 | AB026295 | 59927 ... 59609C | intron-5 |
| Osa#7 | 342 | AJ243961 | 18655 ... 18314C | 5'F(1523) |
| Osa#8 | 343 | AJ243961 | 33544 ... 33202C | 5'F(229) |
| Osa#9 | 327 | AJ245900 | 19061 ... 19387 | 5'F(467) |
| Osa#10 | 304 | AJ245900 | 47364 ... 47061C | 3'F(446) |
| Osa#11 | 312 | AJ245900 | 83914 ... 84225 | 5'F(446) |
| Osa#12 | 334 | AP000367 | 91902 ... 91569C | 3'F(480), 3'F(987) |
| Osa#13 | 342 | AP000391 | 62380 ... 62721 | 3'F(1212) |
| Osa#14 | 337 | AP000399 | 139202 ... 138865C | intron-1 |
| Osa#15 | 345 | AP000559 | 939 ... 1283 | intron-2 |
| Osa#16 | 269 | AP000559 | 6477 ... 6745 | 5'F(1216) |
| Osa#17 | 347 | AP000559 | 75417 ... 75763 | 3'F(1065) |
| Osa#18 | 325 | AP000559 | 80756 ... 80432C | 5'F(1496) |
| Osa#19 | 303 | AP000570 | 8989 ... 9291 | 3'C, 3'C |
| Osa#20 | 312 | AP000570 | 9745 ... 10056 | intron-1 |
| Osa#21 | 339 | AP000570 | 28879 ... 28541C | 3'F(468) |
| Osa#22 | 343 | AP000570 | 29304 ... 28962C | 5'F(191) |
| Osa#23 | 337 | AP000570 | 37206 ... 36870C | 5'F(504) |
| Osa#24 | 342 | AP000570 | 54719 ... 54378C | 5'F(954) |
| Osa#25 | 324 | AP000570 | 111910 ... 111587C | intron-1 |
| Osa#26 | 343 | AP000615 | 67875 ... 67532C | 5'F(1273) |
| Osa#27 | 333 | AP000615 | 68678 ... 68346C | 5'F(2087) |
| Osa#28 | 318 | AP000836 | 29854 ... 29537C | 3'F(858) |
| Osa#29 | 342 | AP000836 | 99718 ... 99377C | 5'F(1209) |
| Osa#30 | 335 | AP000836 | 155125 ... 155459 | 5'F(1355) |
| Osa#31 | 345 | AP000836 | 184537 ... 184193C | intron-4 |
| Osa#32 | 362 | AP000837 | 125297 ... 124936C | 3'F(831) |

[a]Locations of Tourist-OsaCatA like sequences in a base sequence registered in DDBJ/EMBL/GenBank databases. C indicates a complementary strand.
[b]Tourist-OsaCatA like sequences were inserted in a 5'-upstream region (5'F), a 3' downstream region (3'F), an intron, and a 3' terminal region (3'C) of CDS. The number in each parenthesis indicates the length (bp) between a Tourist-OsaCatA like sequence and a CDS in the vicinity thereof.

Further, flower tissue of rice was subdivided and subjected to RNA extraction to analyze the presence or absence of expression of 11 CDSs (protein coding regions presumed to be a gene), two ESTs, and 8 genes with RT-PCR. The result is the following.

Expression in stamen and/or pistil: 12 cases
Expression in stamen, pistil, lemma/palea, and base: 5 cases
Expression in pistil, and lemma/palea: 1 case
Expression in stamen, pistil, and base: 1 case
No RT-PCR product confirmed (no clear growth): 2 cases Thus, it was demonstrated that the genes detected by the method of the present invention were "expressed in a site containing a flower". Preferably, the genes obtained by the method of the present invention can be said to "have a relatively high probability (about 90% or more) of being expressed in the stamen and/or pistil of a flower". The genes whose products were not confirmed are considered to have insufficient RNA. Therefore, the inventors concluded that substantially all of the genes are actually expressed at a site containing a flower. The present invention can achieve prediction of expression of a gene obtained by screening at a relatively high probability (specifically, for example, at least about 90% or more, about 95% or more, and the like), which was not realized by means of conventional technology. The present invention is the very first to achieve such an advantageous effect and usefulness.

As a result, it was demonstrated that the Tourist-OsaCatA base sequences could be used to obtain a method for efficiently selecting genes, which are expressed in a flower, from base sequences of the rice genome in a DNA database.

The method of the present invention, which provides information about an organ (tissue) in which a gene is to be expressed, is of great benefit to the status quo in which although genome analysis can easily determine the base sequence of a genome, the functions of most genes are not known.

Figure 5A:
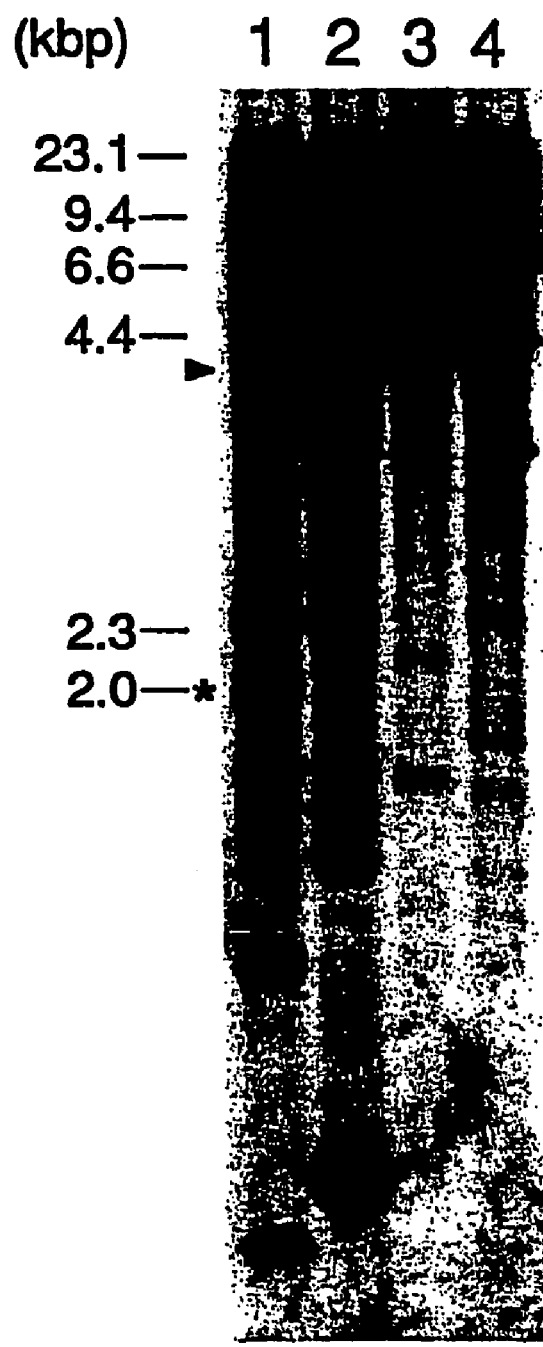
FIG. 5 is a diagram showing a result of Southern analysis for entire DNA of rice (variety: *Nipponbare*). In the Southern analysis, DNA was digested with HindIII and XhoI (lane 1), EcoRV and HindIII (lane 2), BamHI (lane 3), or EcoRI (lane 4), followed by electrophoresis. After hybridization with a probe, the filter was washed with low stringency (A), and then with high stringency (B). 2 kb and 4 kb fragments contained Tourist-OsaCatA, indicated with an asterisk and the point of an arrow, respectively. The size (kbp) of marker DNA (λDNA/HindIII) is indicated to the left.
Figure 5B:
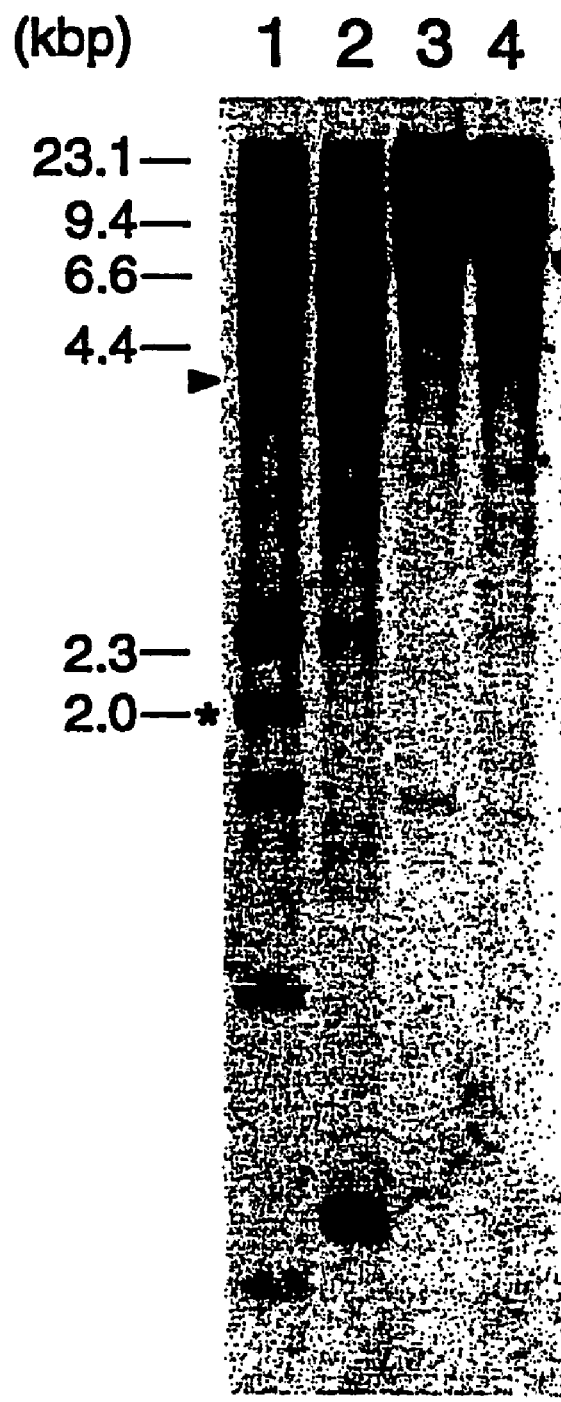

Further, a gene which Southern hybridization analysis of rice genomic DNA reveals has a portion of a putative promoter region, to which a probe (Tourist-OsaCatA) binds under stringent conditions, is highly likely to be expressed in a flower. Such a gene is used for screening a rice genomic DNA library (FIGS. 5A and 5B).

An experiment using a partially deleted promoter revealed that the Tourist-OsaCatA fragment per se is not essential for expression in a flower. It is considered that somewhere in the course of evolution, the DNA structure of a gene which was actively expressed in a flower was relaxed and transposase required for insertion of a transposon was also synthesized and as a result, the transposon Tourist -OsaCatA was inserted in the vicinity of a gene which is to be expressed in a flower.

Hereinafter, the present invention will be described by way of examples. The examples are only for purposes of illustration. Therefore, the claims of the present invention are limited only by the claims, but not the examples.

EXAMPLES

Techniques used in the examples below are well known in the art and described in, for example, Sambrook et al., Molecular.Cloning: A Laboratory Manual (2nd Ed.), Vol. 1 to 3, Cold Spring Harbor Laboratory, (1989). In the examples below, Tourist-OsaCatA is used as an example of a transposon sequence. The present invention is not limited to the specific sequence, and can be easily modified by those skilled in the art reviewing the present specification.

Example 1

Comparison of Base Sequences

A similarity search was conducted in the DNA databases DDBJ (Rel. 35), GenBank (Rel. 111), and EMBL (Rel. 58) accessed from the web site of the DNA bank of the National Institute of Agrobiological Resources (http://www.DNA.affrc.go.jp) using the BLAST algorithm (Altschul et al., Nucl. Acids Res. 25: 3389-3402 (1997)). Base sequences highly similar to Tourist-OsaCatA (score value of at least 40) were compared with the base sequence of Tourist-OsaCatA using genetic information processing software GENETYX-MAC (Software Kaihatsu K.K., Tokyo).

As a result, 228 BACs (bacterial artificial chromosome) clones and 11 PACs (P1-derived artificial chromosome) clones were detected. Among them, 32 Tourist-OsaCatA like sequences were confirmed to be present in the vicinity of CDS in a BAC/PAC clone in which information about a region (CDS) inferred to code a gene is stored (Table 1).

Example 2

RT-PCR

Total RNAs of rice (variety: *Nipponbare*) were prepared from blades, roots, glumose flowers, and immature seeds using RNeasy (Qiagen, Hilden, Germany). The preparation was carried out in accordance with a manual attached to RNeasy. The prepared total RNAs-were treated with DNase I (Life Technologies, Rockville, Md. USA), followed by RT-PCR. RT-PCR was carried out using Superscript One-Step RT-PCR system (Life Technologies). 50 ng of the total RNAs were used as a template. cDNA synthesis was carried out at 47° C. for 40 minutes, and then at 94° C. for 2 minutes. Thereafter, 24 to 40 cycles of reactions at 94° C. for 2 minutes, at 52° C. for 2 minutes, and at 72° C. for 2 minutes are repeated. The resultant amplified DNA fragments were observed by agarose electrophoresis and further base sequence analysis.

As a result, expression was detected in one or a plurality of organs for 8 genes (including CatA) of 12 genes having Tourist C element (classified by Bureau and Wessler, Proc Natl Acad Sci USA 91: 1411-1415 (1994)) having a similar structure to that of CatA and Tourist-OsaCatA (FIG. 2), 2 ESTs of 3 ESTs having a highly similar sequence to Tourist-OsaCatA in DNA registered as EST (FIG. 3), and 11 CDSs of 29 CDSs present in the vicinity of Tourist-OsaCatA like sequence (Table 2). All of the genes, ESTs, and CDSs having detected expression were also expressed in a flower.

TABLE 2

CDS used in RT-PCR analysis
(putative protein coding region)

| CDS | Accession No. | Location[a] | DNA-derived product (bp) | mRNA-derived product (bp) | Putative protein[b] |
|---|---|---|---|---|---|
| 1 | AB023482 | 24114 . . . 28262 | 552 | 552 | AP2 domain containing protein |
| 2 | AB023482 | 80821 . . . 79730C | 318 | 297 | RING-H2 finger protein |
| 3 | AB023482 | 96980 . . . 98055 | 387 | 211 | homocitrate synthase |
| 4 | AB023482 | 116583 . . . 115633C | 803 | 287 | ND |
| 5 | AB023482 | 147866 . . . 146584C | 466 | 185 | Pro-rich protein |
| 6 | AB026295 | 55634 . . . 60562 | 1299 | 419 | ND |
| 7 | AJ243961 | 20178 . . . 21866 | 1230 | 399 | ND |
| 8 | AJ243961 | 32999 . . . 30355C | 2024 | 413 | ND |
| 9 | AJ245900 | 18594 . . . 13572C | 802 | 161 | small Gln-rich tetratricopeptide repeat-containing protein |
| 10 | AJ245900 | 55548 . . . 47810C | 366 | 279 | Ser/Thr kinase |
| 11 | AJ245900 | 84671 . . . 85891 | 506 | 425 | peroxidase-like protein |
| 12 | AP000367 | 97928 . . . 92382C | 374 | 188 | citrate synthetase |
| 13 | AP000391 | 57914 . . . 61168 | 2389 | 379 | ND |
| 14 | AP000399 | 139582 . . . 138524C | 281 | 237 | ND |
| 15 | AP000559 | 40 . . . 4073 | 665 | 206 | ND |
| 16 | AP000559 | 7961 . . . 14114 | 837 | 248 | protein kinase |
| 17 | AP000559 | 78936 . . . 76828C | 192 | 192 | Arg decarboxylase |
| 18 | AP000570 | 8488 . . . 9016 | 492 | 389 | ND |
| 19 | AP000570 | 11735 . . . 9270C | 2443 | 280 | ND |
| 20 | AP000570 | 26400 . . . 28073 | 579 | 208 | ND |
| 21 | AP000570 | 29495 . . . 31839 | 1768 | 146 | ND |
| 22 | AP000570 | 37710 . . . 40502 | 392 | 156 | ND |
| 23 | AP000570 | 53424 . . . 50022C | 411 | 199 | syntaxin related protein |
| 24 | AP000570 | 112576 . . . 109828C | 283 | 283 | ND |
| 25 | AP000836 | 26019 . . . 28679 | 338 | 254 | ND |
| 26 | AP000836 | 98168 . . . 95361C | 527 | 159 | ribosomal protein L30 |
| 27 | AP000836 | 156814 . . . 158260 | 254 | 215 | ND |

TABLE 2-continued

CDS used in RT-PCR analysis
(putative protein coding region)

| CDS | Accession No. | Location[a] | DNA-derived product (bp) | mRNA-derived product (bp) | Putative protein[b] |
|---|---|---|---|---|---|
| 28 | AP000836 | 186228 ... 183159C | 1792 | 220 | ND |
| 29 | AP000837 | 121445 ... 124105 | 277 | 193 | ND |

[a]Locations of Tourist-OsaCatA like sequences in a base sequence registered in DDBJ/EMBL/GenBank databases.
C indicates a complementary strand.
[b]ND indicates that a sequence did not have a significant similarity to the genes registered in a database.

Example 3

Hybridization

Total DNAs of rice (variety: *Nipponbare*) were prepared from blades in accordance with the method of Murray and Thompson (Nucl. Acids Res. 8: 4321-4325 (1980)). The prepared total DNAs were digested with HindIII•XhoI, EcoRV•HindIII, BamHI, or EcoRI. The digested DNAs were separated by 1% agarose gel electrophoresis, and then transferred to a nylon membrane. Southern hybridization was carried out using DNA fragments containing Tourist-OsaCatA as a probe, where the hybridization was carried out in a hybridization solution containing 50% formamide, 5×SSC, 1× Denhardt's solution, 1 mM EDTA (pH 8.0), 0.1% SDS, and 0.1 mg/ml salmon sperm DNA, at 42° C. for 1 day. 32P labeling of a probe was carried out in accordance with Feinberg and Vogelstein method (Anal. Biochem. 132: 6-13 (1983)). Further, washing of a membrane was carried out in 2×SSC, 0.5% SDS at 60° C. for 60 minutes (low stringency) and then 0.1×SSC, 0.5% SDS for 65° C. for 60 minutes (high stringency).

Southern hybridization analysis detected several strong signal bands and a number of weak signal bands. It is believed that the strong signal bands correspond to DNA fragments containing a base sequence having a high similarity to Tourist-OsaCatA, and the weak signal bands correspond to DNA fragments containing a base sequence having a relatively low similarity to Tourist-OsaCatA (FIG. 5).

Example 4

Expression in each Portion of a Flower

Total RNAs of each site in the glumose flower of rice (variety: *Nipponbare*) were prepared from stamens, pistils, lemmas•palea, or glumose flower bases (rachilla, glume, rudimentary glume, lodicule) using RNeasy (Qiagen). The preparation was carried out in accordance with the manual attached to RNeasy. The prepared total RNAs were treated with DNase I (Life Technologies), followed by RT-PCR. RT-PCR was carried out using Superscript One-Step RT-PCR system (Life Technologies). 50 ng of the total RNAs were used as a template. cDNA synthesis was carried out at 47° C. for 40 minutes, and then at 94° C. for 2 minutes. Thereafter, 27 to 40 cycles of reactions at 94° C. for 2 minutes, at 52° C. for 2 minutes, and at 72° C. for 2 minutes are repeated. The resultant amplified DNA fragments were observed by agarose electrophoresis.

Figure 7:
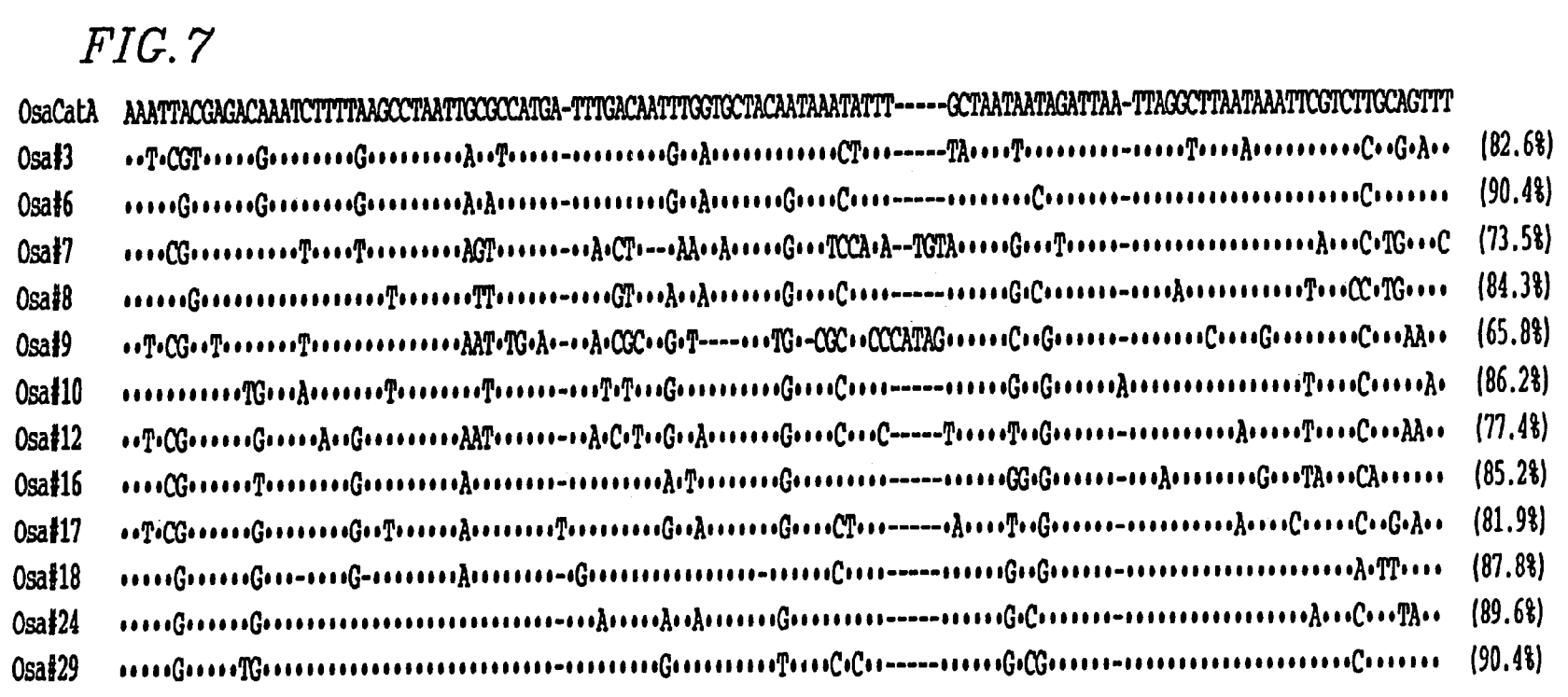

As a result, for 7 genes of the 8 genes shown in FIG. 2 and the 2 ESTs having detected expression in FIG. 3, expression was detected in a stamen or a pistil (FIG. 7A). For the A1 gene, amplification of a plurality of bands having different lengths was observed, and amplification of a DNA fragment having an intended length was suppressed. Further, for 10 CDSs of the 11 CDSs shown in FIG. 4, expression was detected in a stamen or a pistil (FIG. 7B). For CDS3, formation of a primer dimer was often observed, and amplification of a DNA fragment having an intended length was suppressed.

Example 5

Comparison in Homology

Figure 6A:
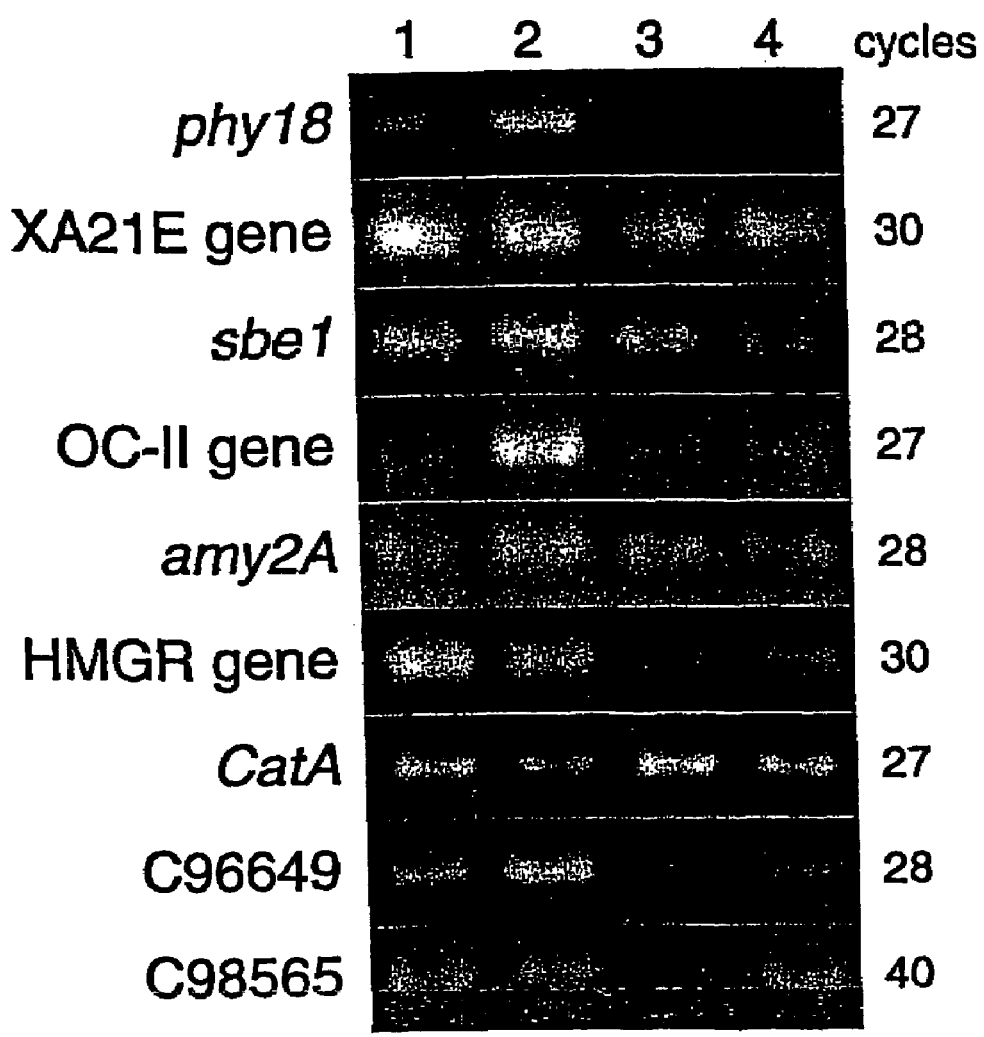
FIG. 6 is a diagram showing results of RT-PCR analysis for gene expression at each site of rice glumose flower of a known gene in the vicinity of Tourist-OsaCatA and a gene corresponding to EST(A), and CDS(B), where lane 1: stamen, lane 2: pistil, lane 3: lemma•palea, lane 4: glumose flower base (rachilla, glume, rudimentary glume, lodicule).
Figure 6B:
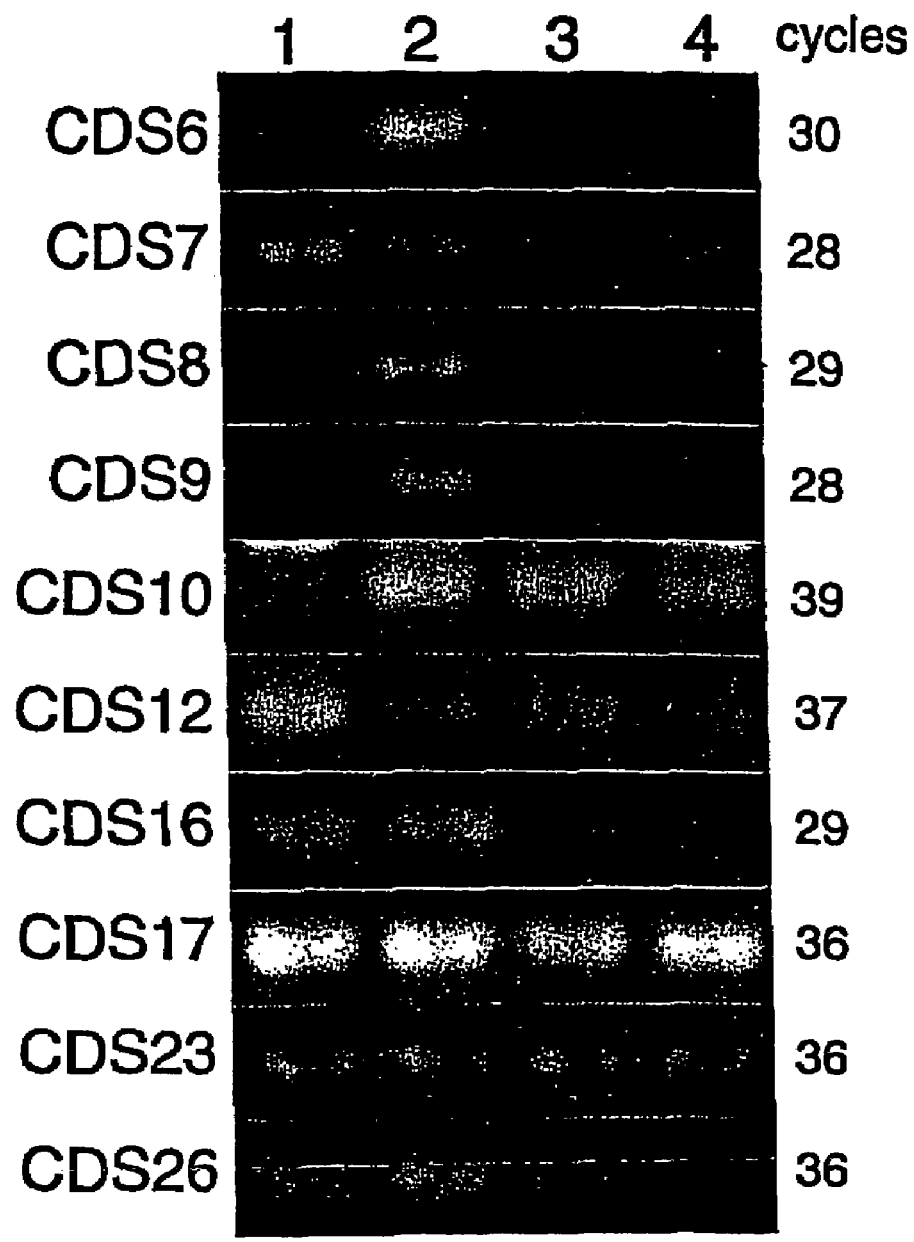

A base sequence (115 bps; SEQ ID NO: 2) at a middle portion of Tourist-OsaCatA was compared with a region corresponding to 12 Tourist-OsaCatA like sequences (SEQ ID NOs: 26 to 37) in the vicinity of CDS having detected expression revealed by RT-PCR, exhibiting 65.8 to 90.4% (average: 82.9%) homology (FIG. 6).

Publications, references or patent applications cited herein are incorporated by reference in entirety.

The above-described invention is described by way of illustration in detail to some extent. The examples are described for the purpose of helping understand the present invention. It will be understood by those skilled in the art from the teaching of the present invention that the examples may be particularly changed and modified without departing from the gist or spirit of the claims attached hereto.

INDUSTRIAL APPLICABILITY

The transposon sequence of the present invention (e.g., a MITE sequence (e.g., a Tourist sequence) (e.g., a base sequence of a Tourist-type transposable element (Tourist-OsaCatA) found in the promoter region of the rice CatA gene)) can be used to efficiently screen for genes which are to be expressed in a site containing a flower. Therefore, these genes are useful to develop a promoter specific to an anther and pollen for breeding rice and the like by genetically modifying a gene relating to an anther or pollen constituting a flower, or modifying components of each tissue of a flower.

The invention claimed is:

1. A method for detecting a gene which is expressed in a flower and other organs in a rice plant, comprising the steps of:
   (1) searching a gene population using a Tourist C transposon sequence consisting of SEQ ID NO: 1 as a key sequence,
   (2) selecting a gene having the transposon sequence in the vicinity of a putative protein coding region, and
   (3) detecting expression of said gene in the flower and other organs.

2. The method according to claim 1, wherein the expression of said gene includes expression of at least one site selected from a stamen and a pistil.

3. The method according to claim 1, wherein the gene population is a library and the key sequence is a probe sequence.

4. The method according to claim 3, wherein the database is a DNA library.

5. The method according to claim 3, wherein the search is carried out by a search method selected from the group consisting of stringent hybridization, microarray assay, POR, and in situ hybridization.

6. The method according to claim 1, wherein the vicinity of the putative protein coding region is within about 2 kbp downstream of a translation termination codon, and within an intron.

7. A method for inferring an organ of a rice plant containing a flower and other organs in which a gene is expressed, comprising the step of:
   (1) obtaining information about whether or not a base sequence of a Tourist C transposable element sequence consisting of SEQ ID NO: 1 is present in the vicinity of the gene and when the sequence is present in the vicinity of the gene, inferring that the gene is expressed in the plant organ containing a flower relating to the Tourist C transposable element sequence.

8. The method according to claim 7, wherein the organ containing a flower contains a site selected from the group consisting of a stamen and a pistil.

9. A method for modifying an expression pattern of a gene of a plant, comprising the step of utilizing the sequence of a gene obtained by a method according to claim 7.

* * * * *

SEQUENCE LISTING

<160> NUMBER OF SEQ ID NOS: 37

<210> SEQ ID NO 1
<211> LENGTH: 352
<212> TYPE: DNA
<213> ORGANISM: Zea mays
<220> FEATURE:
<221> NAME/KEY: misc_feature
<222> LOCATION: (1)..(352)

<400> SEQUENCE: 1

| | | | | | |
|---|---|---|---|---|---|
| gggtctgttt | agttcccaaa | caaaattttt | cacgctgtta | cataggatgt | ttggacacat | 60 |
| gcatagagta | ctaaatgtag | aaaaaaaaca | attaaacatt | tcgccttgaa | attacgagac | 120 |
| aaatctttta | agcctaattg | cgccatgatt | tgacaatttg | gtgctacaat | aaatatttgc | 180 |
| taataataga | ttaattaggc | ttaataaatt | cgtcttgcag | tttccagacg | gaatctgtaa | 240 |
| tttattttat | gagatacagc | tgcttcgatc | ttccatcaca | tattcagacc | gtacctaatc | 300 |
| tgaaaggtta | gtaatttgaa | ctgcgtagta | atgctacaag | gtaaatcaat | ca | 352 |

<210> SEQ ID NO 2
<211> LENGTH: 115
<212> TYPE: DNA
<213> ORGANISM: Zea mays

<400> SEQUENCE: 2

| | | | | | |
|---|---|---|---|---|---|
| aaattacgag | acaaatcttt | taagcctaat | tgcgccatga | tttgacaatt | tggtgctaca | 60 |
| ataaatattt | gctaataata | gattaattag | gcttaataaa | ttcgtcttgc | agttt | 115 |

<210> SEQ ID NO 3
<211> LENGTH: 3960
<212> TYPE: DNA
<213> ORGANISM: Oryza sativa
<300> PUBLICATION INFORMATION:
<308> DATABASE ACCESSION NUMBER: X14172
<309> DATABASE ENTRY DATE: APR-1993
<313> RELEVANT RESIDUES: 4621 TO 8621

<400> SEQUENCE: 3

| | | | | | |
|---|---|---|---|---|---|
| agaagatgtc | ttcttcaaga | cctactcaat | gttccagttc | atccagcagg | acccgccaaa | 60 |
| gctcccgggc | aaggatatta | gcacaaacaa | ctcttgatgc | tgaactcaat | gctgaatatg | 120 |
| aagaatatgg | cgactccttt | gattactcca | aattggttga | agcacagaga | actactggac | 180 |
| ctgagcagca | agctcgttct | gagaaggtca | tagcttactt | gcatcacatt | cagagagcaa | 240 |
| agctaatcca | accatttggt | tgcttgttgg | cccttgatga | aagaccttc | aatgttatag | 300 |
| cgctcagcga | gaatgcacca | gagatgctta | caactgtcag | ccatgcagtg | ccaagtgttg | 360 |
| atgatccccc | aaagctacgc | attggcacca | atgtacggtc | tcttttcact | gacccaggta | 420 |
| ccacagcact | gcagaaggca | ctgggatttg | ctgatgtttc | cttgctgaac | cctatcctag | 480 |
| ttcaatgcaa | gacctcaggc | aagcctttct | atgccattgt | tcatcgggca | actggttgtt | 540 |
| tggtggtaga | ctttgagcct | gtgaaaccta | cagaatttcc | agcaactgcc | gctggggctt | 600 |
| tgcaatctta | caaacttgct | gccaaggcaa | tctctaagat | ccagtcactg | ccaggtggaa | 660 |
| gcatggaggt | gctatgcaat | acggtggtca | aggaactctt | tgacctcaca | ggatatgata | 720 |
| gagttatggc | ttataagttc | catgaagatg | accatggtga | agtctttgct | gagatcacaa | 780 |
| agcctggtct | tgaaccttat | cttggcctgc | attatccagc | tactgatatc | cctcaggcag | 840 |

| | |
|---|---|
| ccaggtttct tttcatgaag aacaaagtcc ggatgatttg tgattgccgt gcaagatcta | 900 |
| tcaagattat cgaagatgag tcgctccact tggatattag cttatgtggt tcaacactga | 960 |
| gggcaccaca cagttgtcat cttcagtata tggagaacat gaactcgatt gcatcccttg | 1020 |
| tcatggctgt tgtggttaat gagaatgagg atgatgatga agttgggct gatcaacctg | 1080 |
| cacaacagca gaagaggaag aaactatggg gactccttgt ttgccaccat gagagcccca | 1140 |
| gatatgttcc tttcccattg cggtatgcct gtgagttctt agcacaagtg tttgctgtcc | 1200 |
| atgttaacaa ggagtttgaa ttagagaggc aagtacgcga gaaagcata ttgaggatgc | 1260 |
| aaacaatgct ctctgacatg cttctcaggg aatcctctcc tctgagtata gtatcaggga | 1320 |
| ctcccaacat catggacctt gtgaaatgtg atggtgctgc tcttttgtat gggggaaaag | 1380 |
| tgtggcggct acagaatgct ccaactgagt ctcagatacg tgatattgcc ttctggctgt | 1440 |
| cagatgtcca cagggattcc actggcctga gtactgatag cctacatgat gctggatatc | 1500 |
| caggagctgc tgctcttggt gatatgattt gtggaatggc agtagctaaa ataaattcca | 1560 |
| aggatatcct gttctggttc aggtcacata cagctgctga atcagatgg ggaggtgcaa | 1620 |
| aacatgatcc atcagacaag gatgacagca gaagaatgca ccctaggctg tccttcaagg | 1680 |
| cattccttga ggttgtcaag atgaagagct tgccttggaa tgactatgag atggatgcta | 1740 |
| ttcactcatt acaacttata cttagaggga cactgaatga tgcatcaag ccaacaaggg | 1800 |
| ccgctagttt agataatcag gttggtgatc tcaagcttga tgggcttgct gaattgcagg | 1860 |
| cagttacaag tgaaatggtt cgtctcatgg aaacagcaac tgtcccaatc ttggctgtag | 1920 |
| atagcaatgg attggtcaat ggatggaatc agaaggttgc tgagttgaca gggttgagag | 1980 |
| tagatgaggc tattggaaga cacatactta ccgttgtaga ggaatcttct gtaccagttg | 2040 |
| tccagaggat gctgtattta gctttgcaag gtgggtaaat tagctatagt ggttttttgtc | 2100 |
| tattccccca gtattttttca gtttctgct tatttggcaa ttcgatttat caaaaaaact | 2160 |
| ttggggttgc tttctaatgt tcaatgccta gcttgttata tgtacatttg attgtcatgc | 2220 |
| tcatacatta atacttgaca ttcagctgcg ttgtgggttg attgatttct aaacatttct | 2280 |
| ttgattgatc aggcaaagaa gagaaggaag tgaaatttga ggtgaaaact catggctcca | 2340 |
| accatgttgt tggtgtgtgc tttgttgcac aagatatgac tgttcataag ttggtcatgg | 2400 |
| acaaatttac tcgggttgag ggagactaca aagcaattat tcacaatcca agcccgctta | 2460 |
| ttcctcccat atttggtgct gacgaatttg gatggtgctc tgagtggaat gctgccatga | 2520 |
| cgaaattgac cgggtggcat agagatgagg tgatcaataa gatgcttctt ggtgaggtgt | 2580 |
| ttgatagcac caacgcctcc tgtcttgtga agaataaaga tgcatttgta agtctctgca | 2640 |
| ttcttatcaa cagtgcatta gctggtgatg aaacagaaaa ggctccattc agcttcttcg | 2700 |
| accggaacgg gaagtatatc gagtgccttc tttctgttaa cagaaaagta aatgcagatg | 2760 |
| gtgtcatcac tggagtattt tgtttcattc aagttcctag tcatgagctg caacatgcac | 2820 |
| tacatgtgca gcaagcctca cagcagaatg cactaacaaa gttgaaagct tactcctaca | 2880 |
| tgagacatgc aatcaacaac cctctctcag gtatgcttta ctctaggaaa gcactgaaga | 2940 |
| acacaggtct gaatgaagag cagatgaagg aggtcaatgt tgcagatagt tgtcaccgcc | 3000 |
| agctgaataa aatactttct gacttggatc aagatagcgt catgaacaag tacttttctt | 3060 |
| accaagtatt ctaagttact ctcttaggct cttgtattta ctttcagcta cctttgttct | 3120 |
| tcatcaattg tcagacctaa caggtcgatg gtgttgctct tatagtctta tgtgtttgta | 3180 |
| ttatcttcaa gtggtcaatt ttgctctctc aaaatgaaag aatttgttgc accaagtccc | 3240 |

-continued

```
agtggttttt tactcattac tcagtacaaa ccttatatat atattattag ttattatctt     3300
caaactaatt tcctgctgct gtgttcacag gtctagttgc ttggatttgg agatggttga     3360
gtttgtattg caagatgtgt tgtggctgc tgtaagtcaa gtactcataa cttgccaggg      3420
aaaagggatt agagtctctt gcaacctacc ggagagatat atgaagcaaa cagtctacgg     3480
ggatggtgtt cgactacagc agattctctc tgacttccta ttcgtctcag tgaagttctc     3540
tcctgttggg ggttctgttg agatctcttg tagcctgacc aagaacagca ttggggaaaa     3600
ccttcatctc atagacctag aacttaggta tgttagtcat gacatttgca cgcttactct     3660
tctttctgtt aagacagtct tgaggtataa aatgatgtgt attaactctt gtggatcaat     3720 gttttttcagg atcaagcacc agggcaaagg agtcccagca gatctgctgt cacaaatgta    3780
cgaggatgac aataaggagc agtcggatga aggcatgagt cttgcggttt ctagaaacct     3840
gctgaggctc atgaatggcg atgtccgaca tatgagggaa gctggcatgt caaccttcat     3900
cctcagcgtc gaacttgctt ctgctccagc aaaataatca tgaaatggta tgtgaaatta     3960
```

<210> SEQ ID NO 4
<211> LENGTH: 1680
<212> TYPE: DNA
<213> ORGANISM: Oryza sativa
<300> PUBLICATION INFORMATION:
<308> DATABASE ACCESSION NUMBER: U70541
<309> DATABASE ENTRY DATE: JAN-1997
<313> RELEVANT RESIDUES: 26881 TO 28561

<400> SEQUENCE: 4

```
acaagcagat cgatcacgca cggtacgcca tgggcgaggc ggtgaagggg ccagtggtgg      60
tgacgggcgc gtcgggcttc gtcggctcat ggctcgtcat gaagctcctc caggccggct     120
acaccgtccg cgccacagtg cgcgacccct gtgagctctc tcatcgtgca ctctagctct     180
ctcctcgtag tttactgact ccaattatat atgccgcttg cttgactctg acaagtgtac     240
gtgttgttgt tgttgttttc agctaacgtt gggaagacga agccgttgct ggagctggcg     300
gggtcgaagg agaggctgac gctgtggaag gccgacctgg gcgaggaagg cagcttcgac     360
gcggcgatca ggggttgcac gggcgtgttc cacgtcgcga cgcccatgga cttcgagtcc     420
gaggacccgg agaacgaggt gatcaagccc accgtggaag ggatgctgag catcatgcgg     480
gcctgcaggg acgccggcac cgtcaagcgc atcgtcttca cctcctccgc cgggaccgtc     540
aacatcgagg agcggcagcg cccctcctac gaccacgacg actggagcga catcgacttc     600
tgtcgccgcg tcaagatgac cggatgggta tgtatcgaaa atgttgtcgt gggttaggaa     660
caacgatcct ccacgtacat aaaacgaaac gataagttaa catgagcatg attaatatta     720
gtatggtata attgatattt gtttaaaatc taaaaaatat taatatgatt tttaaataac      780
tattttatag aattttttttt atgaaaacac aaggaaacag aaattgagaa atagtacgtt     840
caaactcacc cttaagcaac tgaaactagc ttagcacgtg aatttggccg tgcgagtcat     900
atgatatgaa ggtcgggat gtttttttttt ttttgcggg gatgtaatta actaattatg      960
taaaccattt ctattgtcta aaagaagtta gcaagtgata attgtggtgg cagatgtact     1020
tcgtgtccaa gtcattggcg gagaaggccg ccatggaata cgcgagggag cacgggctgg     1080
acctcatcag cgtcatcccc acgctcgtcg tcgggccctt catcagcaac gggatgccgc     1140
cgagccacgt caccgcgctg gcgctgctca cggggaacga ggcccactac tcgatcctga     1200
agcaggtgca gttcgtccac ctcgacgacc tctgcgatgc cgagatcttc ctcttcgaga     1260
```

-continued

```
gccccgaggc gcgcggccgc tacgtctgct cctcccacga cgccaccatc cacggcctcg    1320
cgacgatgct cgcggacatg ttcccggagt acgacgtgcc gcggagcttt cccgggatcg    1380
acgccgacca cctccagccg gtgcacttct cgtcgtggaa gctcctcgcc cacgggttca    1440
ggttcaggta cacgctggag gacatgttcg aggccgccgt ccggacgtgc agggagaagg    1500
ggcttctccc gccgctgccg ccaccgccga cgacggccgt ggccggagga gacggctcgg    1560
cgggtgtggc cggcgagaag gaaccgatac tggggagggg gaccgggacg gcggttggtg    1620
ctgaaacaga agcgttggtc aaatgagtgt tgactagtga gtccagagaa cggtattgaa    1680
```

<210> SEQ ID NO 5
<211> LENGTH: 2520
<212> TYPE: DNA
<213> ORGANISM: Oryza sativa
<300> PUBLICATION INFORMATION:
<308> DATABASE ACCESSION NUMBER: U72724
<309> DATABASE ENTRY DATE: NOV-1997
<313> RELEVANT RESIDUES: 2761 TO 5281

<400> SEQUENCE: 5

```
aaacatctct cgctcttgct gtcttagctt gcaccgatat tctctgcatc tcggcacgat      60
gatatcactc ccattactgc tcttcgtcct cttcttctct gcgctgctgc tcttcccttc     120
gagcagtgac gacgacggtg gtggtgatgc tgccggcgac gaactcgcgc tgctctcttt     180
caagtcatcc ctgctatacc agggggggcca gtcgctggca tcttggaaca cgtccggcca     240
tggccagcac tgcacatggg tgggtgtcgt gtgcggccgc cggcacccac acagggtggt     300
gaagctgcgg ctgcgctcct ccaacctggc cgggatcatc tcgccgtcgc tgggcaacct     360
atccttcctc aggacgctgc aactcagcga caaccacctg tccggcaaga tacccccagga     420 gctcagccgt ctcagcaggc tccagcaact ggtactgaat tcaacagcc tatcgggtga     480 gattccagct gctttgggca atctaaccag tctctcggtt cttgagctga ctaacaatac     540
actgtccgga gcaatcccctt catctctggg caaactcaca ggtctcactg atcttgcact     600
ggctgaaaat acgctgtctg gttccatccc atcatctttc ggccaattgc gcagattatc     660
tttccttagc ttagccttta acaatttaag tggagcgatc ccagatccta tttggaacat     720
ctcctctctc accatattcg aagtcatatc caacaagcta agtggtacac tgcctacaaa     780
tgcattcagt aatcttccta gtctgcagga ggtatacatg tattacaacc agtttcatgg     840
tcgtatcccg gcatcgatag gtaatgcttc caacatctca atatttacca ttggtttaaa     900
ctcttttagc ggtgttgttc caccggagat tggaaggatg agaaatcttc agagactaga     960
gcttccagaa actctttcgg aagctgaaga acaaatgat tggaaattca tgacggcatt    1020
gacaaattgc tccaatcttc aagaagtgga actgggaggt tgtaaatttg gtggagtcct    1080
ccctgattct gtttccaatc ttccctcttc gcttgtatct ctctccatta gagataacaa    1140
aatttcaggg agcttaccta gagatatcgg taatctcgtt aatttacaat atctttctct    1200
cgctaacaac tccttgacag gatcccttcc ctcttccttc agcaagctta aaaatttacg    1260
tcgtctcact gtagataaca acaagttaat tggttctctc ccattgacca tcggtaatct    1320
tacacaacta actaatatgg aggtccaatt taatgccttc ggtggtacaa taccaagcac    1380
acttggaaac ctgaccaagc tgtttcaaat aaatcttggc cacaataact ttatagggca    1440
aattcccatt gaaatattta gcattcccgc actctctgaa attttggatg tgtcccataa    1500
taacttggag ggatcaatac caaagaaat agggaaactt aaaatattg tcgaattcca    1560 tgctgattcg aacaaattat cgggtgagaa ccctagcacc attggtgaat gccaacttct    1620
```

-continued

```
gcagcatctt ttcctgcaaa acaatttctt aaatggtagc atcccaatag ctctgactca    1680
gttgaaaggt ctggacacac ttgatctctc aggtaacaat ttgtcaggtc agatacctat    1740
gtccttaggg gacatgcctc ttctccactc gctgaacctt tcgttcaaca gcttccacgg    1800
tgaagtgcca accaatggtg tttttgcaaa tgcttctgaa atttacatcc aaggcaatgc    1860
ccatatttgc ggtggcatac ctgaactaca tcttccgacg tgttccttaa atcaagaaa     1920 gaaaagaaa catcaaattc tgctgttagt ggttgttatc tgtctcgttt cgacacttgc     1980
cgtcttttcg ttactctaca tgcttctaac ctgtcataag agaagaaaga aagaagtccc    2040
tgcaacgaca tccatgcaag gccacccaat gatcacttac aagcagctgg taaaagcaac    2100
ggatggtttt tcgtccagcc atttgttggg ttctggatct tttggctctg tttacaaagg    2160
agaatttgat agtcaagatg gtgaaatcac aagtcttgtt gccgtgaggg tactaaagct    2220
ggaaactcca aaggcactca agagtttcac ggccgaatgc gaaacactgc gaaatactcg    2280
acaccggaat cttgtcaaga tagttacgat ttgctcgagc atcgataaca gagggaatga    2340
tttcaaagca attgtgtatg acttcatgcc caatggcagt ctggaagatt ggctacaccc    2400
tgaaacaaat gatcaagcag agcaaaggca cttgactctg catcagagag tgtcacgccg    2460
gaatttctat ccaaaattcc aaacgcttac atgtgtgtga accctcgtcc aggaatcagc    2520
```

<210> SEQ ID NO 6
<211> LENGTH: 7320
<212> TYPE: DNA
<213> ORGANISM: Oryza sativa
<300> PUBLICATION INFORMATION:
<308> DATABASE ACCESSION NUMBER: D10838
<309> DATABASE ENTRY DATE: JUN-1993
<313> RELEVANT RESIDUES: 3301 TO 10621

<400> SEQUENCE: 6

```
cgccgatttc gaagctgtgg aaatgggagt cgcctccacg gccaccgaca tccgccgcaa      60
tgctgtgtct cacctcctct tcctcctccg cgcccgctcc gctccttccc tctctcgctg     120
atcgaccgag cccgggaatc gcggtcagtc aatatataga aacttctata tatgatatga    180
ttagttttcc ctctctctct tgttttgtta ggtgtttggg ttattgatgg tgtggtggtc     240
cgcagggcgg gggtggcaat gttcgcctga gcgtggtttc ttcgccgcgc cggtcgtggc     300
ctggaaaggt aagatactgt tgcaggatat ctatcgaatt aggaatttga tgatggtgat     360
aattaattgt ggggaaaaca agtaagtctg aattctttg gccacaggcg acagccccaa     420
aaccccgaca ccccaccgcc gaccacctcg ccgccggcca ccgctcccct ttgccgccgt    480
cggctctacc tccttcccac tctcccgtcc ttctcctagc ctccctcctc tctctctctc    540
tctcaatact tttttctacc tttcatacta ccttccatgt tcttgttccg aatctgggtt    600
cccaagccgc tgatgcgccc cttccctgat tcttctgatg gaactagggg aggctgtgtg    660 gccattttc ccgttggagg gtttcgtcta gatctgtcgg gtgtgggaca tgcggattgc    720
aggtgctgtc ggttgtgttg gcggcggcg gtcctgccgg gatagttggc cgccgacgcg     780
ccgcttggct gttgggttgc acggtgtgtg ctggctggta gcgaggatgg ttttagggtg    840
ttgggcgaaa gctctgtccg actcatagcc ggcctgacgg cgatgaacgt ccttggacat    900
catgcaatgc ccctcctgga ggcgtcgtcg caagagcatc tccagtagag accctaaata    960
caattcctaa acagttttta ggtgctaagg acaaaaaata aactccagca aaacccatac   1020
tacaggtcct aaaataggaa ggacctcaaa taccccctccg cagtccctag gcctggggggc   1080
```

-continued

```
tgtagaccga ggccctatcg ccgttttcct acgcgggagg aaatttcctg acgtgtggtg      1140
tctgtcttcc ctcccgcgga atcgctgcca cggcgccgat cttcgccagc tcgctgttcc      1200
gccgctcgtg gccgacggtg cgaccatcca gtacctccac cggccactgc ttgtcgtccg      1260
cgtgcccact tgcttgtttt ttcgtggtcc ttgatcagtt cgcacactga tgcactatat      1320
ggtagacaag aatgttctga aattcatgac catcagaaac atgttctaaa caatcctgct      1380
ctcgattggt ttatggctaa ctgtggttct aaacgatcat ggcataaaaa ttattgttct      1440
gttcctttaa agtttgtggt gcttggtagg ttgagacaat taggctgctt gcaattatgc      1500
agtagttcct tcaaagatta ttctgcagtg ttgttctttt gtgtcagttg tgagttgaag      1560
tttaacttca aggttttttt tttctaggag gatttaagct cttttctgaag tttctcagat      1620 agattagatt ggaaaaggta tagagttaat tttatctatt gattatagtt cttatttaat      1680
tgaactacgt agtgtcttga atacttgccg gtaggatttc actcccatgt ttgagaattt      1740
tgaatttgaa ttatggtatt taaaattatg gatttgaata caattgaatt ctatacatta      1800
gaaatattcg tatttgaatt attactatgt taaactaggt gtaagcatag agtataatca      1860
gaaatacaag agaaaagaa atgggggcta agaaataggg tctgctggta gagttggagg       1920
taatttttga attcttagaa aatagggaca gccctcattc aacctttgag gactctaaaa      1980
tagggactac tgctggagat gctctaacac cctgttcccc cttgctgctg ggtgaaaacc      2040 cttttccagtc tcctgtttat gcgatggtgg cgtccttttcc gacgtcgtca ccttcttcaa     2100
ggcatcgttt ttggagaaac cctgcaacca gtccccctgc tttcccatcc ttctccccta      2160
ttccatcccc tcctcctccc cttttcttct gtcaagggct cctatgcttg gaaactctca      2220
tgtatctctt ctctgtaata tattcaggtg gggaaatgtt ggattttat tgattggaat       2280 actgtattgg gtcatctcgg tgacaccaaa gctgtacttt ggtggagtag caatctttgc      2340
ccttattgac cggataggat tttggttaaa tttatctacg ttttttgtttg cggttcatct     2400 ttttttcctac cagtcttata caagatggta cagtttagca atgattgtta cattgcaata    2460
tataaatcga agtgatagaa gccacctcaa gtaaatctaa ctattgttca taattcaaag     2520
gtcaagacca atttctcagt tcctgcgact gcgcgaaaaa acaaaaccat ggtgactgtt      2580
gtggaggagg tcgaccacct tcctatatat gatctggacc ctaagttgga ggaattcaag      2640
gatcacttca actataggat aaaaagatac ctcgaccaga aatgcctgat tgaaaaacat      2700 gagggggggcc ttgaagaatt ttctaaaggt taagttcact acttcaattt aatgcacaaa    2760
tactccttca tacaagagtc ggcatatgct attttctttg catcttttaa ctctttatgg     2820
ttctctcatt ccatcttttg taggctattt gaagtttggg attaatacag ttgatggtgc      2880
cacaatatat cgtgaatggg cgcctgctgc acagtaagtt ctaatgtagt catccagcta     2940
ttcgctaatg tttatgtgtt gtaggaaata tggatcactg atcagttgtt taagtaccac     3000
ttcttcattt tattttcaat acctatgctt tgtctggtag cagctagcag aaagttaatt     3060
ttacaacata agatagctcc tcaccgccgg taatagagat gttttgagtt ttcactcata      3120
gcacgtcttg gctgtttaag gtaagtatcg ggggtagaac ataatgccat gaagagagaa      3180
aattatgtta tctgtgtccg attgtagttg gttctgaact tgtgaggctg tgatttctta     3240
attgtcgttt tgttaagac cttaccagta tttgcaatat ttaatgcatt tttttgcggg      3300
gaaatattca atgcatttaa cttggaggtt tttcttcatg catatagaga agcacagctc      3360
attggtgagt tcaataactg gaatggtgca aaacacaaga tggagaagga taaatttggc      3420
atttggtcaa tcaagatttc acatgtcaat gggaagcctg ccatccctca caattccaag     3480
```

-continued

```
gttaaatttc gctttaggca tgggggtgga gcatgggttg atcgtattcc cgcatggatt    3540
cgttatgcaa cttttgatgc ctctaaattt ggagctccat atgatggtgt acactgggat    3600
cctccagcct gtgaaaggtc ctctacttgt gccttgaact acaatgtaaa caagcttcaa    3660
atatttggga agcataaaga cgcaaagctt tgctgacatg atcactgtta ctgtttacct    3720
tacaggtacg tgtttaagca tcctcgacct ccaaaacctg atgctccacg catctatgag    3780
gctcatgtgg ggatgagtgg tgaagagcca gaagtaagca catacagaga atttgcagac    3840
aatgtgttac cacgcatacg ggcaaataac tacaacacag ttcagttaat ggcaatcatg    3900
gaacattcct actatgcttc ttttgggtat cacgtgacaa attttttcgc agtcagcagc    3960
agatcaggaa caccgagga tctgaaatat cttgttgaca aggcacatag tttaggatta    4020
cgagttctga tggatgttgt ccatagccat gcgagtaata atgtgaccga tggtctaaat    4080
ggctatgacg ttggacaaaa cactcatgag tcttattttc atacaggaga taggggctac    4140
cataaactct gggatagtcg tctgttcaac tatgccaatt gggaggtctt aagatttctt    4200 cttttctaatt tgagatattg gatggacgaa ttcatgtttg atggcttccg atttgatggg    4260
gttacatcaa tgctatacca tcaccatggt atcaataagg gatttactgg aaaactacaag   4320 gagtatttca gtttggatac cgatgtggat gcaattgttt acatgatgct cgcaaaccat    4380
ttaatgcata aactcttgcc ggaagcaact attgttgctg aagatgtttc gggcatgcca    4440
gtgctttgtc ggccagttga tgaaggtgga gtagggtttg acttccgcct ggcaatggcc    4500
attcctgata gatggattga ctacctgaag aacaaagagg accgcaaatg gtcaatgagt    4560
gaaatagtgc aaactttgac taacaggaga tatacagaaa aatgcattgc ctatgccgag    4620
agccatgatc aggtatagtt atccattatc taacagatga tcaggtatag ttgggtggta    4680
atacacttgt ttgacttggt agacaaatca acacttagct gatggctctg aatactttga    4740
tatcgcataa tcctgtaggt tatcaaattg ctactctatt ttttgatagc tattgacagt    4800
aagcaggttc cttttttcac tatgaatagt aacaatgtat aagggcctta caaccattat    4860
ccaataatta gctgcagcat gctgttagct tcatgttctt atgtcgagac agttactgaa    4920
ttgctgattt tacacatttt tcagtccatt gttggtgaca agactatagc atttctcttg    4980
atggacaagg aaatgtacac tggcatgtca gacttgcagc ctgcttcacc taccatcaac    5040
cgtggcattg cactccaaaa ggttatttc cccttaattg ttgttgattt catggtgcta    5100
gttctagaca attgttgtaa tgtccataga tttactaaaa tttctggtcg ttatttgaat    5160
acaatgtgtc ctggcctctt ttaatattat ttggctaatt gtgcttcaaa tatttcagat    5220
gattcacttc attacgatgg cccttggagg tgatggctac ttaaatttta tgggcaatga    5280
ggtaatatct tagtaatatg ttgaaactcg cttcctgtta atgcgttcct tgaatgttga    5340 ttccttttgca ttctctttcc tttgtgtggg taaagtgagg cacataaagg gttagcccgc    5400
tgttcttaag atgcccaagt acttggcagc taattttaa catacataaa ctgaagcatt    5460
gttatctttg tgcatgatgt gttctgttat tcctggtcat ccactaatcc aaatcataca    5520
taaactgaaa tcacacacat gatttatatt gatattttct cttgagtagc acaaacatga    5580
tatagtggta ttatcaagtc ttatgctaca tataaaatga gttccttgca caacatgggc    5640
tatatgtacg gcatagctgc tgtgtctggg gttcttgtat gtctttccaa ctcatattga    5700
ttctgcaatt tcttttagtt tggccatcca gaatggattg actttccaag agaaggcaac    5760
aactggagct atgataaatg cagacgtcag tggagccttg tcgacactga tcaccttcga    5820
```

| | |
|---|---:|
| tacaaggttg tgcctaagta tatcaatgta ttttacatgt tttgtcatgg cagcaccttt | 5880 |
| tggttgtttg ccatcatcac ctcccttttg gttcaatgtt cttgctattt acagtgggct | 5940 |
| cctattcact ttggaatcga gttcaaattt cctgtgcagc acattattc aatcctttcc | 6000 |
| tattagcata aaatgtttcc ttaggctacc tacagtttct ttgatgttca cacagaattg | 6060 |
| atgtgggcat gcattttcca tgcataaatc ggaacggcat gttctgaaaa attattctaa | 6120 |
| agataaggac gaatgccaag gaccctgtcc atttgttcaa atgtagttct ttctctgcat | 6180 |
| aaaacaattt atccttatga attattcgta ttttccccag cattctctgc agtcaagctc | 6240 |
| tgcaatttgt ctcacctaac atgtctaatt tttaattgca ccaatattga acagtatatg | 6300 |
| aatgcatttg atcaagcaat gaatgcactc gaggaggaat tttccttcct gtcatcatca | 6360 |
| aagcagattg ttagcgacat gaacgagaaa gataaggtaa tggcaattgt aatttagtat | 6420 |
| gggcccttgt tgcttgtatg tccatatgta ttcaaatgag gtgagttgtt caggaaagca | 6480 |
| cggcacgaaa ttctagctat gtggtgagac aattaatttc ttaaaataca actgtacaat | 6540 |
| taactccaag ttccttttca ggttattgtc tttgaacgtg gagatttggt ttttgttttc | 6600 |
| aattttcatc ccaacaaaac ttacaagggg taactaattc attttaagct ttgccttttg | 6660 |
| aaaatactct gttcagtact aatataatc tccacttgca aaatgtgcag ttacaaagtc | 6720 |
| ggatgtgact tgcccgggaa gtacagagta gctctggact ctgatgcttt ggtctttggt | 6780 |
| ggccatggaa gagtaagcag cgacggcaaa tgctcaaaat attttgcac tctttctcct | 6840 |
| aaactattga ggcaccacca aatttgcatc agataactta tttgcagtat tgatcttgtt | 6900 |
| gtaccacagg ttggccatga tgtggatcac ttcacgtctc ccgagggaat gccaggagta | 6960 |
| ccagaaacaa atttcaacaa ccgccctaac tcattcaaag tcctttcccc gccccgtacc | 7020 |
| tgtgtggtaa agtccattca ctgaaatttt cataactaat gagccataac caactgcaat | 7080 |
| gcaacctcac aaaatgcttc actatcaggc ttactatcgc gttgatgaag atcgtgaaga | 7140 |
| gctcaggagg ggtggagcag ttgcttctgg aaagattgtt acagagtata tcgatgttga | 7200 |
| agcaacaagt ggggagacta tctctggtgg ctggaagggc tccgagaagg acgattgtgg | 7260 |
| caagaaaggg atgaagtttg tgtttcggtc ttctgacgaa gactgcaaat gaagcatcag | 7320 |

<210> SEQ ID NO 7
<211> LENGTH: 780
<212> TYPE: DNA
<213> ORGANISM: Oryza sativa
<300> PUBLICATION INFORMATION:
<308> DATABASE ACCESSION NUMBER: X57658
<309> DATABASE ENTRY DATE: APR-1993
<313> RELEVANT RESIDUES: 421 TO 1201

<400> SEQUENCE: 7

| | |
|---|---:|
| ctccaccggt cgcggctcgc cggcgatggc cgaggaggcg cagagccacg cgcgtgaagg | 60 |
| tgggcggcat ccacgacagc cggccgggcg cgagaacgac ctcaccaccg tcgagctcgc | 120 |
| ccggttcgcc gtcgccgagc acaacagcaa ggccgtaaga tttaagaaca ccgccccct | 180 |
| ttcttttttc cccttgttaa cttgcgtgga tcgccgtgtg gattgtggta aaatataaa | 240 |
| atacaataag ggcatgttta gtttccacgt aaaaatttta ccataaagt attaaatata | 300 |
| ggctaaaaga ataattaatt atatagattg cgattaattt atgagacgaa tcttttaagt | 360 |
| ctaattgctt catgattcgt ccatgtgacc gtaaatatct aatgactgat taattaggct | 420 |
| taataaaattc tggtttactg acgtattta aattagttgt tttttagtgc ccgaacacct | 480 |
| catgcgatac cttacataat acttgatgtg atatgctaaa attttacacc cttaacctaa | 540 |

```
gcaccccta agctaattgc agaacgcgat gttggagttg gagagggtgg tgaaggtgag      600
gcagcaggtg gtgggcgggt tcatgcacta cctcaccgtc gaggtgaagg aacccggcgg     660
cgccaataag ctgtacgagg ccaaggtgtg ggagagggcg tgggagaact tcaagcagct     720
ccaggatttc aagcccctcg acgccaccgc ctaaacgtaa aaccatcttt taacctttcc    780
```

<210> SEQ ID NO 8
<211> LENGTH: 3540
<212> TYPE: DNA
<213> ORGANISM: Oryza sativa
<300> PUBLICATION INFORMATION:
<308> DATABASE ACCESSION NUMBER: M74177
<309> DATABASE ENTRY DATE: APR-1993
<313> RELEVANT RESIDUES: 541 TO 4081

<400> SEQUENCE: 8

```
aggagagaga tcgagctata gagctagcct ggctgctgcc atggcgaccg gacgacgcct      60
ctccatgatc ctcctcctcc tccttctcgg cttggcttcc ggcgacaaga ttctcttcca     120
ggtacgcagc cagccacggc ctgaactgaa gttgtgaccg atttcagttc agtttctgaa     180
caagctgttg cgttctcttc aggggttcaa ctggagtcg tggaggcaga gcggagggtg     240
gtacaacctg ctgatgggga aggtcgacga catcgtcgcc gccggcgtca cgcacgtctg     300
gctgccgccg ccgtcgcact ccgtctccac gcaaggtcgg tttctcctgc tgctcctcct     360
tgtctgaaac taaactctga acattttgga attggcgaaa tttgggatcc tgcaagcgtg     420
gagtggacag cacgctaact aagctaccct gattgcgaag tgtggataat gattgtcact     480
ttggccttta tttcatttgg gttggaatga gatgtttcac tgatttagtt gaggaatttt     540
tggctagata atatcacact gacatgcgta agggtcaatc aatcttgcaa cccccattcta    600 atcttataca gatcgcaata caaggtaag ctgtcagcag ttagaaaaaa agattaatga     660
tatataatta gtgtaataat gagtactagt aattaagctc cttccaggaa aaaaaatgct    720 ttttttcac tttccgaagt aactaatatg ccactttatt atcatgtttt tattttctaa     780
aaacaataaa aaaactact actgtacttc ctgtgggtac gaaaacatat catttctaaa    840
catttaaact ggatgtgcaa aaatcatgtg taaattagt atactttatc cgttccactt     900
cgggtattca aaatacatac taactcaggg tctattggc ataactctag cttcagaagc    960
tccagcttca ggtcaacctt tttcgaagct ggagctcaac caaacaattt tagctccata    1020
gaaattgatg ttgattttac aaagttgaag ttgattagga cgtgacatac acggagcgt    1080 atcctatgca cacagaccct cgcgtgtaca caccgtgtac aacaactaaa aattatcaca    1140 aaaaattttta gaaaaattca tacatgtact tcaatagta ttcatctac gtacaaagtc    1200 gcatcttcaa attcattcta catagagaat aacaaaaaag ataaaattct gacaaatttg    1260
caaccttaaa actgtcagat ttttttttgt tcacggctaa aatataatga atttgacgtt    1320 aagatttaa ccctaggtgt aatacaattg aaagtatgtg tataattttt tctagatttt    1380
ttggtgacat tttttagttg gtgtgcacac gtgtgtacac gtgtgggact gtgtgcatag    1440
gatatgttgc cgacatacac acatgtagtg agtatgcata aggcatgcca tatttatatc    1500
ttggtctcta ctttatctta catcattaaa atgtcaatgg tgaatttcat atctctgtaa    1560
ccatttacca ttattcatat tttcgtatct ttctctacaa tcactatggc tcattctatc    1620
tttttttatt gaataaatgt atgtccaaat aacaacttt ttgttatat attcatgtag    1680 tatcataatc agcgcctaga tctacaaact tagccatgta gtatccttt ggtcttggtt    1740
```

-continued

| | |
|---|---|
| tggttatgca ccaaaacgag cgattttata ggttcgtgta ctagattgca tccacttatc | 1800 |
| caatttactc gttattcaat gtggcgatgt gcgtgaaggg tacatgcctg ggcggctgta | 1860 |
| cgacttggat gcgtctaggt acggcacgtc gatggagttg aagtcgttga tcagcgcgct | 1920 |
| ccacggcaag ggcattcagg cgatcgctga cgtggtgatc aaccaccgct cgccgacta | 1980 |
| caaggacagc cgcggcatct actgcatctt tgagggcggc acacctgacg gccgcctcga | 2040 |
| ctggggcccc cacatgatct gccgcgatga tacccagttc tccgacggca caggcaacct | 2100 |
| cgacaccggc gccgacttcg ccgctgcccc cgacattgac cacctcaatg gtgtcgtcca | 2160 |
| gcgggagctc accgactggc tcctctggct caagtctgac gaggttggct tcgatgcgtg | 2220 |
| gcggctcgac ttcgcaaggg ggtactcgcc ggaggtggcc aaggtgtaca ttgaggggac | 2280 |
| aacgccggtg gggttggcgg tggcggagct gtgggactcg atggcgtacg gcggagacgg | 2340 |
| gaagccggag tacaatcagg acgcacaccg gcaggcgttg gtggactggg tggacagggt | 2400 |
| gggtgggacg gcgtcggcgg ggatggtgtt cgacttcacg acgaagggga tcatgaacac | 2460 |
| ggcggtggag ggggagctgt ggcggctgat cgaccagcag gggaaggcac cggggggtgat | 2520 |
| cgggtggtgg ccggcaaagg ctgtcaccttt cgtcgacaac cacgcactg gctcgacgca | 2580 |
| acagatgtgg ccattcccct ccgacaaggt catgcagggc tacgcctaca tcctcaccca | 2640 |
| tcccggcaac ccatgcatcg taagtactcc tactactacc acctctgttt ttaaatagat | 2700 |
| gacatcgtcg attttttatc acatgtttgg tcattgtctt atttaaaaaa taatgtaatt | 2760 |
| ataatttatt ttgttatgaa ttgttttatc actcaaagta ctttaagtat gatttatatg | 2820 |
| ttatacattt acataaatta attgattatt tggttaattg actctcgaat aacaggcact | 2880 |
| attaattgat tattgtcatt tcagttgact ataaatattt ttttaagaa acacactttg | 2940 |
| gtaatagcta tatttgtgac cctacagact tcagtagtaa aacatattta taattatttg | 3000 |
| taattttttc caagtaagga agtagtcaaa gtttaatatt gaatacttca tcaattttt | 3060 |
| gctatttatt agccgtctaa tactttttg cccttattta tcagttgtct actaaacttg | 3120 |
| cataatgcac gtgtgtacat atatatacac tcatcagtca tctaaaattg cacaataatg | 3180 |
| tgcctgtata tatgtacatg tagttctacg accatttctt cgattggggg ttaaaggagc | 3240 |
| agatcgcggc gctggtggcg gtgaggcagc ggaacggcgt gacggcgacg agctcgctca | 3300 |
| agatcatgct gcacgacgcc gacgcctacg tcgccgagat cgacggcaag gtggtgatga | 3360 |
| agatcggctc ccgctacgac gtctccagcc tcatcccgcc cggcttccac ctcgccgccc | 3420 |
| acggcaacgg ctacgccgtc tgggagaaaa gcgccgccgc cgccgccgat catcgcacct | 3480 |
| cttccagcgc atcgctctga ttgattagcg atatgatgct tttgtgccac ctcttatgtt | 3540 |

<210> SEQ ID NO 9
<211> LENGTH: 4500
<212> TYPE: DNA
<213> ORGANISM: Oryza sativa
<300> PUBLICATION INFORMATION:
<308> DATABASE ACCESSION NUMBER: L28995
<309> DATABASE ENTRY DATE: FEB-1994
<313> RELEVANT RESIDUES: 1981 TO 6481

<400> SEQUENCE: 9

| | |
|---|---|
| cgcgcggagg gcgctcacct gggcgctgcc cctcccgatg cggatcacca acggcctggc | 60 |
| catggtctcc ctcgtgctct cctcctgcga cctcgtccgc ctctgcagcg acagggagcg | 120 |
| gccctcggc ggccgggagt cgccaccgt cgtctgccag ctcgcctccg tcgtctacct | 180 |
| cctcagcctc ttcgcccacc ctgacgcccc cgccaccacc accggcgacg acgacgacgg | 240 |

-continued

```
ccagggggc tcccgccgcg ccgcgccgcc ggagcccgcg ccaatgcatg ggcatggtgg      300
cgggatgatg gagggcgacg acgaggagat cgtcgccgcg gtggcgtccg gcgcgctgcc      360
gtcgcaccgc ctggagtcgc ggctcgggga ctgccgccgc gcggcgaggc tgaggcggga      420
ggcgctgcgg cgggtgacgg ggcggggagt ggagggcctc cccttcgatg ggatggacta      480
ccaggccatc ctggggcaat gctgcgagat gccggtcggg tacgtgcagc tccccgtggg      540
ggtcgccggc ccgctgctcc tggacggccg cgagtaccat gtccccatgg ccaccaccga      600
gggatgcctc gtcgccagcg tcaaccggcg cgtgcagggc catctcgtct ccggcggggc      660
cttcagcgtt ctgctccggg acgccatgtc ccgcgctcct gctgtcaagc tgccttgccc      720
aatgcgggca gcggagctca aggcgtttgc tgaggcgcct gcgaattttg agttgctggc      780
tgctgtcttc aataggtaca ctccacatca tccactaatc tagtttgttg atttgtgtgc      840
ttgctcaaag tgttataaga ctttgcgcga caataggcag gcacagtgtt aattaatggg      900
ggaaaaatgt gatcttcagt gtatctagtg tcgtctatgt tgagtatgac tgagtgatag      960
ctagcactga tgattaagac caggtgattt ctcacaacgg aaagcccttc tatcatgtga     1020
ttgctgacag ggtagagccc acagtgtagc tagcacatgc actggaggta ctggacaatg     1080
cattatcaat actatgttta ctttgtttct aagagctaca gctaaatgca gataatgcag     1140
ctcatagata ataccttct gaagtgttca ccttgaattg cctttttatg ttcgcttaaa     1200
taataccaaa tgtgaatgaa tcattggttt gtgctctcca aacttgagaa tatgtggatt     1260
taagatctca actctagtgt gtatcttgca cttcagatgt tcaggactc agggtacaca     1320
catctactga cagtttacgg tgttagaatt ttcagattaa tgtcatttgt cttttggagt     1380
ttttctgtgt tactgactag taactgtcgc tctgtagtca gtatccttag aggactattg     1440
tctctctctt tttttttaaa tgtacgatat gttgttttgt gttattttgt tgtctggaac     1500
cctttacgta attgtaggct catgttcaaa agctttggtt actgtcatta agtacacttt     1560
agataacagt aggcttgtgt tccaataagt tattgttggt tttcatgttt ctaattaatg     1620
tatcttttct tacattgttt tctgtcattt gagagtactg agaaaatatg gaggctttta     1680
ttgaatctct ttaaaaaatt gtggccgtgt gtttcaaagt tccaataggg tccaacagtt     1740
agttcctagg tatgctgcat ttagtatact ttcctaatat cctcacttgt gctatttac      1800
cacacaagcc acttctgtga tttccacaac tttgttgtgc agatttttca tattcatatt     1860
tttctttgat ttttcatatc cagttattca gacactgtac atattggcat attattctac     1920
cagtcaaagt caaaggtgtc tatacatctt atttgatttc tgatctttta aactgtacag     1980
tgttttatag ttgttcttgg cagctagaac catctaccca ataccgacgt gactctatgg     2040
gttgcatata tgggcaagtg tcatggttcc atggatacct ttttgcatag tgtattctcc     2100
agggactttt ccagagctaa gtgtgagttt gccattgaca ttgttctttc aacctctgca     2160
tttcggattg catatgtttc agtcttagtt tttgatgtgg caaatgtcac acaatatttt     2220
agattgcact gtggttgcta tacagggttg atttggtact attgtttgaa gatccattat     2280
actgtgagaa tcaatctgtt tgtacaactt atctgattgt tatcctcctc tgtgccctat     2340
ataagttcta atttagtaaa tttcatgcat actttattgt tggctgtgta cactcttgtg     2400
gagtgtagag gctggaatga tatccattat ctaaaaaatg tatactttat tgtggaaatt     2460
ttcatttgag acaatcacgc agcttgctta tctaaggccc catttaatct ccacatttgg     2520
agataaattt tggttgcacg taaaacgaga aagctcatta gcacataatt aattaagtat     2580
```

```
taactattat aaatttgaaa aatggattta ttttctttttt taaaacaact tctatataga    2640 aactttttt aaaaaaatgt atcatttaac aatttgaaaa gcgtgctaac ggaaaacaag      2700
gaagttgaag aatagaacag ggcctaagtc gttcttacat catccttttt ttttctttt      2760 tgctctattg tttcgcttcc tttgtagaac caataacttc gtatagaggt catcttctat     2820
tagaattgac ataaaaactg ttttaatcgg tgtaggtcca gcagatttgg taggcttcaa     2880
gacattcgtt gtgcactcgc tgggaggaac ctatatatga gatttagctg tatcactgga    2940
gatgctatgg gaatgaacat ggtgtcaaaa ggtgttgaga atgtcttggg ctatctgcag     3000
aatgtcttcc ctgacatgga tgtcatcagc gtatctggtt ttaactcttc cccttgaact    3060
ttgcatgctt cagttagttt tgctttcctc tctaagtcaa tgcctccttt tagcagaaaa    3120
cgaataaaaa atcacattct ttaacttctg tttggaaatg ttgcgaagga aatgatgaaa    3180
aacatatttc atcagcaccc aaaatatttc ctctcctatt gctttgtaac ttaaagaaac    3240
atgtccctaa ttagattttt ccgatctaga gaggaaacct tggcttcatt tacagaaagc    3300
agatatcggt tcttagaaga ttcagcaggt tataagatgg atttttttca tccctaagaa   3360 gtatttttg gatgccttt tatttatttt ctgctcattg tgcactagcc tagttcaatt      3420
gtaaaatata ttctgattac cgaataacag tgaatgtact acttttcatc agactcgcat    3480
caaacatagt ctaatattct ctgataatat atttgcgtgt atcaattagg catttgtacc    3540
ggggtgcttt ttttttgaaac aatgggtgtt cacactatct gttttcatca attccacatg  3600
tattttcttg tctttgcatg cacattgatg aattaatctg tgtgcatcag gtaactattg    3660
ctcagacaag aagccgacag ctgtaaactg gatagaaggc cggggaaat ctgttgtttg    3720 tgaggctatt attaaaggag atgttgtgca gaaagttctt aagacgactg tagaaaaact    3780
tgttgagctt aacattatca aaaatcttgc tggatcagct gtagctgggg ctcttgggggg  3840 ttttaatgcc catgcgagta atattgttac tgcattattc attgctacag gacaggatcc    3900
tgcacaaaat gttgaaagct cacaatgcat caccatgttg gaagaagtaa atgatggaga    3960
tgatcttcat atctctgtca ccatgccgtc cattgaggtg attatttatt cgttttactt    4020
tccgttccta cctgcattat gtagattata gcataaccgc tagccttaaa tggagctgca   4080
aaatctatag catagagatc ttgtattaac tgaagtaata ttttgtttta gcatgcagtt    4140
tgatcgtgag agcaatatcc gcatcgattt ttatttattt aatttcttca tgttagtaaa    4200
atggttcatt ttttctctca ggtaggtaca atcggaggtg gtacatgtct ggcctcacag    4260
gcggcttgtt tgaacctgct tggtgtcaag ggttcaaatc atggctcacc tggtgcaaat    4320
gctgggcgtt tggctaccat agtagctggc agcgtcgtcg ctggccgagc tctgctcctt    4380
gccgctcttg cctctggtca ccttgtcaag agccacatga tgtacaatcg atcaagtaag    4440
gatgtcgcca aggctgcttc ttgagcccag ttcgcatcat tcaaatgctg gacatattta    4500
```

<210> SEQ ID NO 10
<211> LENGTH: 2280
<212> TYPE: DNA
<213> ORGANISM: Oryza sativa
<300> PUBLICATION INFORMATION:
<308> DATABASE ACCESSION NUMBER: D29966
<309> DATABASE ENTRY DATE: APR-1996
<313> RELEVANT RESIDUES: 1561 TO 3841

<400> SEQUENCE: 10

```
gatacctgct gctgccacta gcccactacc atggatcctt gcaaggtcag tcactcagtg      60
actagtgaga ctaaatctac ttaatcttgt agttaataat tgaggtttca tttagctagt     120
```

```
tgtgtagatt caagagagag cttaacttct tatagaatat ttggtcgatt atcagaaact    180
tcctgaaata acctagatta tcgactagat tctacgaata tttcttttt agtctcaagc    240 tcttcaaaca tgcatggctg gttgattcag ctagtcgatc attaagtata taattaatta    300
attaattaat agtaatacgt gctacccatg cagttccggc cgtcgagctc gttcgacacg    360
aagacgacga cgacgaacgc gggagctccg gtgtggaacg acaacgaggc gctgacagtg    420
gggcccaggg ggccgatcct cctcgaggac taccacctga tcgagaaggt ggcgcacttc    480
gcccgggagc gcatcccgga gcgcgtggtc cacgcccgcg gcgcctccgc caagggcttc    540
ttcgagtgca cccacgacgt caccgacatc acctgcgccg acttcctccg gtccccgggc    600
gcccagaccc ccgtcatcgt ccgcttctcc accgtcatcc acgagcgcgg cagcccggag    660
acgatccgcg acccgcgcgg gttcgccgtc aagttctaca cccgcgaggg caactgggac    720
ctcctcggca caacttccc cgtcttcttc atccgcgacg gcatcaagtt ccccgacgtc    780
atccacgcct tcaagcccaa cccgcgctcc catgtccagg agtactggag ggtcttcgac    840
ttcttgtccc accaccccga gagcctccac accttcttct tcctcttcga cgacgtcggc    900
atccccaccg attaccgcca catggacggc ttcgcgtca acacctacac cttcgtcacc    960
cgcgacgcca aggccaggta cgtcaagttc cactggaagc ccacctgcgg cgtcagctgc    1020
ttgatggacg acgaggccac gctcgtcggc ggcaagaacc acagccacgc cacccaggac    1080
ctctacgact ccatcgccgc cggcaacttc cccgagtgga gctgttcgt ccaggtaggt    1140 gatcatccag aaattaacgc ctatacgatc tgagttcgaa gccgcagtac tccttctaat    1200
taattattta atactgttag gtgatcgacc cggaggagga ggagaggttc gacttcgacc    1260
cgctggatga caccaagaca tggccggagg acgaggtgcc gctccggccc gtggggcgcc    1320
tcgttctcaa ccgcaacgtc gacaacttct tcaacgagaa cgagcagctg gcgttcgggc    1380
cggggctggt ggtgccgggg atctactact ccgacgacaa gatgctgcag tgcagggtgt    1440
tcgcgtacgc cgacacgcag cgctacaggc tggggccaaa ctacctgatg ctgccggtga    1500
acgcgcccaa gtcgcccac cacaacaacc actacgacgg cgccatgaac ttcatgcacc    1560
gggacgagga ggtggactac tacccatcgc gccacgcgcc gctccgccac gcgccgccga    1620
cgcccatcac gccgcgcccc gtggtgggga ggaggcagaa ggcgacgata cacaagcaga    1680
acgacttcaa gcagcccggg gagaggtaca ggtcgtgggc gccggataga caggagaggt    1740 tcatcccct cgccggcga gtcgcgcacc ccaaggtctc ccctgagctc cgcgccatct    1800
gggtcaacta cctctcccag gtaattcata ccagcaattt agtattacct ccatttttgt    1860
ttttatgaca ctactagtta aagtttgaac taatcaacgt catataaaaa aaacggaggg    1920
agtagttatt agtaatgatt aattgttttc tcttagttaa tccacatgat taacaccatg    1980
tttagcacaa cagtttttatg aatccataga taaattattt aatcctatttt tatatgaaat    2040 atataattt aaaccactgt agagaatttg aaattaatat gacttaatcg ctattaattt    2100
gcactaattc cggcaaaaaa agctattaat ttgcactaac tatgtaatta actcatttac    2160
ttcatgcagt gtgatgagtc gttggggtg aagattgcga ataggctcaa cgtgaagcca    2220
agcatgtgaa gaaactaagg cacaagaatg catcatctct tgttaattaa ttggagtact    2280
```

<210> SEQ ID NO 11
<211> LENGTH: 4260
<212> TYPE: DNA
<213> ORGANISM: Oryza sativa
<300> PUBLICATION INFORMATION:

<308> DATABASE ACCESSION NUMBER: X89226
<309> DATABASE ENTRY DATE: APR-1996
<313> RELEVANT RESIDUES: 1081 TO 5341

<400> SEQUENCE: 11

| | | | | | |
|---|---|---|---|---|---|
| ccacccgcc | tcctcccct | ccctctca | ccatcgcatt | tcacaatgcc | tcctactctc | 60 |
| ctcttcctcc | tcctcctcct | cccacctcc | ctcgcctccc | ccgaccgcga | catctacgcg | 120 |
| ctcgccaagc | tcaaggcggc | gctcgtccca | tcccctccg | ccaccgcccc | accgccgctc | 180 |
| gccagactgg | gacccggccg | cgacctcccc | cgcgcactgc | accttctccg | gcgtcacctg | 240 |
| cgacggccgt | cccgcgtcgt | cgccatcaac | ctcaccgccc | tcccgctcca | cttcggctac | 300 |
| ctcccgcccg | agatcgccct | ccttgactcc | ctcgccaacc | tcaccatcgc | cgcctgctcc | 360 |
| gtccccggcc | acgtccccct | cgagctcccc | acccttccct | ctctccgcca | cctcaacctc | 420 |
| tccaacaaca | acctttccgg | ccacttcccc | gtccccgact | cgcgatggcg | cctcccccta | 480 |
| cttcccctcg | ctcgagctca | tcgacgctta | caacaacaac | ctctcagggt | tgcttcctcc | 540 |
| cttctccgct | tcacacgctg | cctccgctac | ctccaccacg | gcggcaacta | cttcaccggc | 600 |
| gcaatcccga | cagctatgca | cctcgccgcg | ctcgagtacc | ttggactcaa | cggcaacacg | 660 |
| ctctccggcc | atgtccccgt | ctccctctcc | cgcctcaccc | cgctccgcga | gatgtacatc | 720 |
| ggatactaca | accagtacga | cgcggtcccg | ccggagttcg | gcgacctcgg | cgcgctcgtc | 780 |
| cgcctcgaca | tgagcagctg | caacctcacc | ggccccgtcc | cgccggagct | cggccgactc | 840 |
| cagcgcctcg | acacgctctt | cctgcagtgg | aagcctctcc | ggcgagatac | gccgcagctc | 900 |
| ggcgatctca | gcagccgtgc | gtcgctcgac | ctctccgtca | acgacctcgc | cggcgagatc | 960 |
| cctcccagcc | tcgccaacct | ctccaacctc | aagctcctca | acctcttccg | gaaccacctc | 1020 |
| cgcggcagca | taccggactt | cgtcgccggc | ttcgcgcagc | tcgaggtgct | gcagctgtgg | 1080 |
| gacaacaacc | tcaccggcaa | catccccgcc | gggctcggga | gaacggccg | cctcaagacg | 1140 |
| ctcgacctgg | ccaccaacca | cctcaccggc | cccatcccgg | cgggacctct | ggccggccgg | 1200 |
| cggctggaga | tgctcgtgct | catggagaag | gcctggttcg | gccccatccc | ggactcgctc | 1260 |
| ggcgactggc | aagacgtcac | gccggtccgc | ctcgccaaga | acttcttgac | cggcccggtt | 1320 |
| cccgccgggc | tcttcaacct | cccgcaggcc | aacatggtgg | agctcaccga | caacctgctc | 1380 |
| accggcgagc | tcccggacgt | gatcggcggc | gacaagatcg | gcatgctgct | gctggggaac | 1440 |
| aatgggatcg | gtggccgcat | ccctccggcc | atcggcaacc | tcccggcgct | gcagacgctg | 1500 |
| tcgctggagt | ccaacaactt | ctccggagcg | ctgccgccgg | agatcggcaa | tctcaagaac | 1560 |
| ctgtccaggc | tcaacgtcag | cggcaaccgg | ctcaccggcg | ccattccaga | cgagctcatc | 1620 |
| ccgtgcgcct | ccctcgccgc | cgtcgacctc | agccgtaacg | gcttctccgg | cgagataccg | 1680 |
| gagagcatca | cgtcgctcaa | gatactgtgc | acgctgaacg | tgtccaggaa | caggctcacc | 1740 |
| ggcgagctcc | cgccggagat | gtccaacatg | acgagcctca | cgacgctcga | cgtgtcgtac | 1800 |
| aacagcctct | cgggccccgt | gccgatgcag | gggcagttct | tggtgttcaa | cgagagctcg | 1860 |
| ttcgtcggca | accggggct | gtgcggcggc | ccgtggctg | acgcgtgccc | tccgtccatg | 1920 |
| cgcggcggcg | gcggcggcgc | gggtcccag | ctgcggctgc | ggtgggactc | gaagaagatg | 1980 |
| ctggtggcgc | tggtggcggc | cttcgcgcg | gtggcggtgg | cgttcctggg | cgcgaggaag | 2040 |
| gggtgctcgg | cgtggcggtc | ggcggcgcgg | cggcggtcgg | gggcgtggaa | gatgacggcg | 2100 |
| ttccagaagc | tggagttctc | ggcggaggac | gtggtggagt | gcgtgaagga | ggacaacatc | 2160 |
| atcgggaagg | gcggcgcggg | gatcgtgtac | cacggcgtga | cgcgcggggc | ggacgtggcg | 2220 |

```
atcaagcggc tggtggggcg cggcggcggc gagcgcgacc gggggttctc ggcggaggtg    2280
acgacgctgg ggaggatcag gcaccggaac atcgtgaggc tgctggggtt cgtgacgaac    2340
agggagacga acctgctgct gtacgagtac atgccgaatg ggtcgctggg ggagatgctc    2400
catggcggga agggggggca cctcgggtgg gaggcgaggg cgcgggtggc ggcggaggcg    2460
gcgtgcggcc tctgctacct ccaccatgac tgcgccccga ggatcatcca ccgcgacgtc    2520
aagtccaaca acatcctcct cgactccgcc ttcgagggcc acgtcgccga cttcggcctc    2580
gccaagttcc tcggcggcgc cacctccgag tgcatgtccg ccattgctgg ctcctacggc    2640
tacatcgcgc aggtaaccac cccaaaataa tttctccaca ttattttag cctatttctt     2700 attactatct ttttcaatgc gaaccactac agtactgtag tactaaattt accgaaatga    2760
atctgtttga aaatattga attccaagac ccaacaagtt tatcctgatc catgtgttga    2820
aagaacaaac ttttttttc tgatccatgt gttgaatgaa caaacctttt tctgtttaac    2880
catgacaagg aacaaacttt atatctggac catgacaaag aacaaacttt taatgtgctt    2940
aaaataaaga atggttctaa ctataactaa tataattgaa atgatctgat acgattatac    3000
gaagtgtcat tgaaaaattg taaactttac gtagaggcaa taatagaggg ggcccctgca    3060
tggagatgca gccacgttcc atccactgga actgcactag tactgtactg cagcttgtgc    3120
tttcctctga gcacaatcct tgttgccttg tgcacggtca actggggaga ggacaaatgt    3180 taccctttggg ccaaagtgtg aacattttt tttctgcag acagcaaaca aaagttacag    3240
ctacagttct tgccgttgca tggctgtagc agtgattgtg attaatggtc agttcagttt    3300
tctgctctgt ttcttttgat tctacagaag cagatcttgc agccatatgt atggtcaatg    3360
gcaggcaagg caatttggct accttttggat taatggatag tctcctgcct ttggagtact    3420
agcattcata ttgtgtcgtc ttgttgcctc gtgtgtggca ctctggcact ctcttggata    3480
attggaggag atactgtttt actgtagctg tatcacgttc gtatcttggc tgtatctcca    3540
tggtagatct gctccttatt gacttgtcag tccactctta aatggtgtag ttggtgaagt    3600
acgtagcttc aggataacct gtctttcaaa cgattcgagt gtgatgcact accctgaaaa    3660
atgaaaattc tgtctagtgg ctgtggttac attcagttat gcaaatgtgc agctctaatg    3720
gctgtagtta cattcagtta tgcgcgttgg gaaaggatcg gtacactata tctttttgat    3780
tgataatcta aaaatggtat gttaggtatc atctaactga ttcatcaatc ctatgtacta    3840
tttttgtttg cagagtacgc atacacgctg cgagtggacg agaagagcga cgtgtatagc    3900
ttcggtgtgg tgttactgga gctcatcacc ggacgccgcc ccgtgggcgg gttcggtgac    3960
ggcgtggaca tcgtgcactg gtccgcaag gtgaccgccg agctgccgga caactccgac    4020
acggcggccg tcctcgccgt ggccgaccgc cgcctgacgc cggagccggt ggcgctgatg    4080
gtgaacctgt acaaggtggc catggcgtgc gtggaggagg cgagcacggc ccggcccacc    4140
atgcgcgagg tcgtccacat gctctccaac ccaaactcgg cccagcccaa tagtggtgac    4200
ctcctcgtca ccttctgaac cccaaactta acggtattgt ttgctgttaa tgtgtgcgct    4260
```

<210> SEQ ID NO 12
<211> LENGTH: 660
<212> TYPE: DNA
<213> ORGANISM: Oryza sativa
<300> PUBLICATION INFORMATION:
<308> DATABASE ACCESSION NUMBER: X52422
<309> DATABASE ENTRY DATE: APR-1993
<313> RELEVANT RESIDUES: 1381 TO 2041

```
<400> SEQUENCE: 12
aatttgcttg agaggatgga gaactaccag gggcagcacg gctacggcgc cgaccgcgtc    60
gacgtgtacg gcaacccggt gggcgccggc cagtacggcg gcggcgccac cgcgcccggc   120
ggaggccacg gagcgatggg gatgggaggt catgccggcg ccggcgccgg cggccagttc   180
cagccggcga gggaggaccg caagaccggc ggcatcctcc accgctccgg cagctcaagc   240
tccagctcgg tacgttcact gtcgtccatt cataaatcta attaatcgcc tcgcttctga   300
attcctttat ttaatttgag ttgtactcgt gtgcgtttgt gcagtcgtct gaggacgacg   360
ggatgggagg gaggaggaag aagggatca aggagaagat caaggagaag ctgcccggcg   420
gcaacaaggg caacaaccag cagcagcagc agatgatggg gaacactggc ggcgcgtacg   480
ggcagcaggg ccacgccggg atgaccggcg ccggcaccgg cgtgcacggt gcggagtacg   540
gcaacgccgg cgagaagaag ggattcatgg acaagatcaa ggagaagctg cccggccagc   600
actaaattaa taagcttata taattgacag ccggggcaac acgtcgtcat gtgtgtagta   660

<210> SEQ ID NO 13
<211> LENGTH: 3660
<212> TYPE: DNA
<213> ORGANISM: Oryza sativa
<300> PUBLICATION INFORMATION:
<308> DATABASE ACCESSION NUMBER: Z15085
<309> DATABASE ENTRY DATE: APR-1993
<313> RELEVANT RESIDUES: 1081 TO 4741

<400> SEQUENCE: 13
gtacacatct gtaatggagt gcgaaaccgg gcttgttcgt tccctgaacg gcgacgggct    60
gtgcatgtcg tcggtgtcgg cgccgccgcg ggccgaccca ctgaactggg ggaaggcggc   120
ggacgagctg gcggggagcc acctcgacga ggtgaagcgc atggtggagg acttccgcca   180
gcgcctggtg aagatcgagg gcgccagcct gacgatcgcg caggtggccg ccgtggccgc   240
cggcgccggc gacgccaggg tggagctcga cgagtccgcc cgcggccgcg tcaaggccag   300
cagcgactgg gtcatgaaca gcatgagtga aggcaccgac agctacgcg tcaccaaccg   360 gcttcggcgc cacctcccac cgccgcacca aggagggcgg gctccagagg gagctcatca   420
ggtgacaaat cgatcgcaag ctcgatcctt tattttgttt cactccatgt tcatcagtct   480
ttacatcagc agttcgattc tatgattacg acgagattga ggatcaccat attagtttat   540
ttaatctctc agaacttgtg gggcgaacta gatgcgcttg catgtgctct cgctgcatag   600
ttgtgtgtgt gcccacgaga taccgtcatt ctcggagcca aaaaggattc tttcggggtg   660
tcagccagcc aatactagta ctggagtata tccttcgcca ttattacact attatgatcc   720
atccagctgt agtatttggg taaaatcatc accatattta ttacttctcg ccaccatcca   780
aacacgcaga tgtactgtac ctcttgctca gttcatgcca catctgaacc ggctactagt   840
agtaaccgtc ctgcactgtt acacctttaa tttgcaccac acgaacacga ctcgtgttaa   900 ctaaaagaa agtgaaaaca caagacgacg attatgtgtc cgttggcgcg tcgctagaac   960 tccttttgc gtctttcgtc tgaggagagg agaaggagaa aggaagcaac cttttttctct  1020 cttttcttt tcgggacatt tgataatatg tttatccatg agataattct gtcgccgagc  1080
gagaattcgg gatctcagag gtatccggcc atccggccaa gtagcagct gctgggctat  1140 catatcaacg cgagtagtaa taacaccaac tgcgtgcgtt tgctcggttc ggccgacggg  1200
ttggcgcgat ggcgctcgcg tcgcgactca gccatgcac gcggggcgcc ggacaaagcg  1260
ttcggcagcg cagaaaactt cacatggaga cgacgtgggc agtgggctgg cctgcttcgg  1320
```

-continued

```
gggatttttcc cacggccacg ttacggcgaa agcgagctga ggtttggtga cacatcccct    1380
gtcctcgcag ggagacagac aaattcacgg ctctggtttt cctttcctgt tttatcatcg    1440
actggtttgg gagctccaat tattaaacga cagtatgcaa ataaaattga agggggaaat    1500
agtcaaaata ccctgaacat gtggagttgt ggacgagtag ttgtagtatt cgtatccgag    1560
ataaggtcca aaacactttg ttttcgtta tttaaacgtg atgtagaaca atattggtac     1620
ttatttgact tttaccacat ggcggtgacc gacagttctg cacagctgca caactacgcg    1680
catctgactt gtttgctctc cttatcatgg ggagcataat taattaagca attatgaaac    1740
tctaaattaa tcatcagtcg gcacggcggc agtgtgtatg tacaccgaag gaaaatacgg    1800
aaagagaata cgcaatcata tatctgatta agtttttttct gaacgtgtta tatgtttttt    1860
tttagtgagc tctgaaactg aaattgacat gtctatcgct ctgttttaac agattcctca    1920
atgccggcgc cttcggcacc ggcaccgacg gccacgttct gccggcggag gcgacgcgcg    1980
cggcgatgct cgtccgcatc aacaccctcc tccagggtta ctccggcatc cgcttcgaga    2040
tcctcgaggc catcaccaag ctgctcaatg ccaacgtcac gccgtgcctg ccgctccggg    2100
gcaccatcac cgcttccggt gacttggtcc cactgtcctc attgccggcc tcatcaccgg    2160
ccgccagaac tccgtggccg tcgccccgga tggtcgtaag gtgaccgccg ccgaggcatt    2220
caagattgcc ggcattgagc acggcttctt cgagttgcag cctaaggaag gtcttgccat    2280
ggtgaacggc actgccgtcg gctctggcct tgcatcgacc gtgctctttg aggccaacgt    2340
ccttgccatc tcgcccgagg tcctgtccgc cgtgttctgc gaggtcatga cgaagccgga    2400
gtacaccgac cacctgacac acaagctgaa gcaccaccct ggacagatcg aggctgccgc    2460
catcatggag cacatcttgg aaggcagctc gtacatgaag ctggcgaaga agctcggcga    2520
gctcgacccg ttgatgaagc cgaagcagga caggtacgcg ctccgacgtg cgccgcagtg    2580
gctcggcccg cagatcgagg tcatcccgtt cgccaccaag tcgatcgagc gcgagatcaa    2640
ctccgtcaac gacaacccgc tgatcgatgt ctcccgtggc aaggcgcttc acggtggcaa    2700
cttccagggc acgccatcg gcgtgtccat ggacaacacc cgcctcgccc tgctgccat     2760 cggcaagctc atgttcgcgc agttctctga gctcgtgaac gacttctaca caacgggct     2820 tccttccaac ctgtccggtg gacgcaaccc cagcttggac tatgggttca agggcgcgga    2880
gatcgccatg gcgtcgtact gctccgagct ccagttcttg ggcaacccgg tgaccaacca    2940
tgtccagagc gcggagcagc acaaccagga cgtgaactcg cttggtctca tctcctccag    3000
gaagaccgcc gaggccatcg acatcctgaa gctcatgtcc tccacgttct tgatcgccct    3060
gtgccaagcc atcgacctgc gccacctcga ggagaacatg aagaccgcgg tgaagaactg    3120
cgtgatgcag gtggccaaga aatccctgag catgaaccac atgggcggcc tccacatcgc    3180
tcgcttctgc gagaaggacc tgctcaccgc gatcgaccgc gaggccgtgt cgcctacgc     3240 cgacgacccc tgcagcgcca actacccgtt gatgcagaag ctccgcgcgg tgctgatcga    3300
gcacgcgctc gccaacggcg accgccgagc gcgtcctgga gacctccatc ttcgccaagg    3360
tggccgagtt cgagcagcac gtccgcgccg cgctgcccaa ggaggtggag gccgcccgcg    3420
ccgccgtcga gaacggcacc ccgctcgtcc aaccggatcc aaggagtgcc gctcgtaccc    3480
gctctaccgg ttcgtgcgcg aggaggtcgg caccgagtac ctcaccggcg agaagacgcg    3540
gtcgcccggc gaggagctga acaaggtgct cgtcgccatc aacgagcgca agcacatcga    3600
cccgctgctc gaatgcctca aggaatggaa tggcgcgcca ctgccactct gctgaacaga    3660
```

<210> SEQ ID NO 14
<211> LENGTH: 1287
<212> TYPE: DNA
<213> ORGANISM: Oryza sativa
<300> PUBLICATION INFORMATION:
<308> DATABASE ACCESSION NUMBER: U72255
<309> DATABASE ENTRY DATE: JAN-1999
<313> RELEVANT RESIDUES: 901 TO 2188

<400> SEQUENCE: 14

| | | | | | |
|---|---|---|---|---|---|
| ttgctctgct | gcctctcgcg | cccgcgcagc | agtgagcagc | agcaagagca | gcaaaatggc | 60 |
| tctacccggg | ggcctccgcg | ccctcatcct | cgccgttgca | ttgccgctgc | tcttcctgtc | 120 |
| cgcttcaggt | aacgagagat | ttggcaatgc | aggtggttta | gtggagagta | gtgtggttga | 180 |
| ttggtggaga | gtagtgtggt | tgattgttgg | gttggtttgg | ttacagaggc | gggcacggtg | 240 |
| gggatcaact | atgggagggt | ggcgaacgac | ctgcccaacc | cggcggcggt | ggtgcagctg | 300 |
| atgaagcagc | agggcatcgc | gcaggtgaag | ctgtacgaca | ccgagccgac | cgtgctgcgg | 360 |
| gcgctggcca | acaccggcat | caaggtggtg | gtcgcgctgc | ccaacgagca | gctgctcgcc | 420 |
| gcggcgtcgc | gcccgtcgta | cgcgctcgcc | tgggtgcgcc | gcaacgtcgc | agcgtactac | 480 |
| ccggccacgc | agatccaggg | catcgccgtc | gggaacgagg | tgttcgcctc | ggccaagaac | 540 |
| ctcacggcgc | agctcgtccc | ggcgatgacc | aacgtgcacg | ccgcgctggc | gaggctcagc | 600 |
| cttgacaagc | ccgtcaaggt | gtcgtccccc | atcgcgctca | ccgcgctcgc | cggctcgtac | 660 |
| ccgccgtcgg | ccggcgtgtt | ccgggaggac | ctcgcccagg | cggtcatgaa | gcccatgctc | 720 |
| gacttcctcg | cgcagaccgg | ctcgtacctc | atggtgaacg | cgtacccgtt | cttcgcgtac | 780 |
| tctggcaata | ctgacgtcat | ctccctcgac | tacgcgctgt | tccgcccgaa | cgccggcgtg | 840 |
| ctcgactccg | ggagcggcct | caagtactac | agcctcctcg | acgcccagct | cgacgccgtg | 900 |
| ttcaccgcgg | tgagcaagct | tgggaactac | aatgccgtgc | gcgtcgtggt | gtcggagacc | 960 |
| gggtggccgt | ccaagggtga | cgccaaggag | accggcgccg | cggcggccaa | cgccgcggcc | 1020 |
| tacaacggca | acctggtgcg | ccgcgtcctc | tccggcaacg | ccagaacgcc | gcgccgcccc | 1080 |
| gacgccgaca | tggacgtgta | cctcttcgct | ctcttcaacg | agaaccagaa | acccggaccg | 1140 |
| acctccgagc | gcaactacgg | cgtgttctac | ccgaaccagc | agaaggtcta | cgacgtcgag | 1200 |
| ttcgtcctcg | gcggcaactc | gctggcggcg | gcggcagcag | cggcaaggac | aacggcgggc | 1260 |
| tcggctggca | ggacaacggc | ggggtaa | | | | 1287 |

<210> SEQ ID NO 15
<211> LENGTH: 1140
<212> TYPE: DNA
<213> ORGANISM: Oryza sativa
<300> PUBLICATION INFORMATION:
<308> DATABASE ACCESSION NUMBER: AB023482
<309> DATABASE ENTRY DATE: MAR-1999
<313> RELEVANT RESIDUES: 96961 TO 98101

<400> SEQUENCE: 15

| | | | | | |
|---|---|---|---|---|---|
| ttggttcctc | cccatcaaaa | tgcttggctc | acttatgtct | tactcacctt | cagtggtatg | 60 |
| ttttagattc | atatgcagtg | atatatagtt | aaatctctta | tgtagaacaa | gtatccaggt | 120 |
| ggaggtatta | ttagtcatgt | aaagataatc | aaagagctgc | gacttttcct | ttgtgcttag | 180 |
| ctgtgtcatt | cgctgatatt | cttatacttg | agttttactt | ttttggttta | ggattcaaag | 240 |
| acggagaaca | ctgatgagtt | aattgcgact | ggtgttcttg | ctagtctgca | gaatttcatc | 300 |
| cgcaaatgca | ttgtagctgt | cctctcgtat | ggcccaatgc | ctaagcatat | tgcatttatt | 360 |

```
atggatggta accgtagata tgctaaattc aggagtatcc aggaaggctc tggtcacagg      420
gtgggcttct ctgctctcat tgccagcctg ctctactgct atgaaatggg cgtgaagtat      480
atcacggtgt atgcatttag catcgataat tttaagcgag atccgactga ggtgaaatcc      540
ttgatggagt taatggagga aaagatcaat gaactgctag aaaacagaaa tgtcatcaac      600
aaggttaact gtaagatcaa cttctggggg aacttggaca tgttgagcaa atcagtgagg      660
gtagcagctg agaaactgat ggctaccact gctgaaaaca cgggactggt cttctctgtt      720
tgcatgccat acaactccac ttctgagatt gtcaatgcgg tcaataaggt ctgtgcagaa      780
aggagggata tactgcagag ggaggatgct gacagtgttg cgaataatgg tgtgtattca      840
gacatttcag tggcagatct ggaccgccat atgtacagcg ctggttgccc cgatcctgac      900
attgtgatcc ggacctcagg tgagactcgc ctgagcaatt ccttctgtg cagacgacg      960 ttcagtcatt tgcagaatcc agaccctctt tggccggagt tctctttcaa gcaccttgtc     1020
tgggccatac tccagtacca aagagttcac ccttctattg agcaaagcag aaatctggct     1080
aagaagcagc tgtaatcaca tcctccctgg gaggagatag aaaccatcat acaagatatc     1140
```

<210> SEQ ID NO 16
<211> LENGTH: 4980
<212> TYPE: DNA
<213> ORGANISM: Oryza sativa
<300> PUBLICATION INFORMATION:
<308> DATABASE ACCESSION NUMBER: AB026295
<309> DATABASE ENTRY DATE: APR-1999
<313> RELEVANT RESIDUES: 55621 TO 60601

<400> SEQUENCE: 16

```
gttcgggaaa tctatggctg tcgtcaccgg cgccaaagag gagggagagt tcgccggcgg       60
tggaataata agtcgacgtc cctccggtga gctaccctct ctcccttccc cctcatcccg      120
aggttgaaga tgcttccccct aatcctgagg ttgaagatga tgccctggca attggatcat      180
aacaggggcg ggcccactat tgattcaagg gtattcagac gtatacccaa gattttttaga      240 caaaaaaaat aagtatatgt actctatacc tcgtatatgt attcaagaaa ttaaagaaaa      300
aggctaaaac tactcatttt gggccctgtt tcatcgtttc ttctctattg ggcctaaatt      360
tcccacttcc ctccccttc atctcagccc acaatcagtt tgggccacaa ctagttcatt      420
tcccctcctc gcctaggcac agcaaaccaa agccctaatt cccaaatcgg ccaaacccta      480
accagaggac cgaggacgtg cgcggtgtgg cggcgaggac gtgcggcagt gcggcggcgg      540
cgacttccgg ctgcgtcggc ggaaggcggc gccaaggcgg gtaggagcct aggcagcgcg      600
tcgggcggcg gcgactgcag tctagtctgc agcgtgctcg tcgcggctg cggcagaggc      660 ttccggctgc ggcgtgcgcg gctgcgtcgg cggcaggagg cgccgaggcg tgcaggcggc      720
gcgtcgacgg ctgcggccgt gcggcgttgg ggctcggcca ggcgtgcagg ccgccagtcc      780
accaggccac cacacaggta cgcgatgcgg cagccgaacg accacggctt gccggcctgg      840
catggattgc gtgagggct tgattcattg attcattgca ttgatttgtt ctaggtagtt      900
caatagtagt tatgttttcc ggtggcgacg gcttgtttca ttgatttgtt ctatagtagt      960
tcaatagttc actagcaccg aaggattcaa cttcctcagt tcctgtcttc tttattttc     1020 agagtgttaa ctgttaagtg tatatttatt gacagattga tagtataaag ctgtaaatat     1080 taggaatttta gataacttag aaccataata tttaattttc agtgtgttaa atttatatat     1140
atgatgatag tatgaggcta tatatgagct gttgttagga atttagagaa tttagagagg     1200
```

```
gtgttttctt cgatgaacta tataaaaaca agaagcaaga tgagcaacaa tctacattta    1260
ttggaagaga atttttgta caagttaaag gatgaggaca tcatcactca tttttaaaat    1320
atcaagcatt gaaaagttct cctctaaatt gtaagttttt tttatcattt taccattttc    1380
tatcctttac atgttatata tgttgccact ttcatatgtc gaacaattag tacttatata    1440
tgttaaagaa tttggactta tgatcaattc tatcaattta taaagttatg gccatatgct    1500
ataatattat acaattagta atgtgtaata ttataccaat taattattgg acttctagaa    1560 gtaaaagaa ttttgtttta cccctaccta tttcgaatac ccaacctcta atcctgggc     1620 ccgccactgg atcataatcc aacggccagg tccaggtgac tgaaatgtgc ctagcgaatc    1680
ctaacatatt cgttctttgg ccccggcgat gagtagcaag tttattactc tctccgtttc    1740
aggttataaa acatttttgac tttggtcaaa gacaaactgt ttcaagttta actaagttag   1800
tttcatcaaa tcaataattg aatatatttt tataataaat ttatcttggg ttgaaaatgt    1860 tactacctt ttctacaaac ttgatcgaac ttaaaacaat ttgactttaa ccaaagtcac     1920
caaagtcaaa acgtcttata acctaaaacg gagggaggga gtacatgcca agttgttgtg    1980
aattccttgc ggataataaa agtcatcatc agtaaattct atatattttt catatatatc    2040
caaacattat ttcttttatc agttctacac atacttattg tggtatcagt gctttgatga    2100
gacggatacc atcctatggt cgtgtatcag aataattagg aaagcctagt gctaaaagct    2160
cgaataccta tcctaaaatt tctgggaccc tgcttgaaaa ccaagatttt gtctcaattc    2220
agactgaaaa tattttacac agtgaagaaa aattgtgcag aaaccaaacg taaactagat    2280
ggatcatgca ttgtttcagc accttctaat tagctagttg tcttgaacag tacactcctt    2340
gattcttctg tatttccact tattgttcca attccatgga taacagagga aagtaacctt    2400
gttgcattcg gcatagaaat gggtaacaat ttaatacacc aaagaaaact acaagatcgt    2460
ggccatggta aacaaatcga tgagaatgca agaccaggtg taaggcttga agaccttcca    2520
tgggtatgtt catcttaact tcttttctgt ttgagtgttg ggtagaaatg ggatttattt    2580
ataatctcca aatgtatgtg atgcatttgc tgcaggacct tgtagtatac aaaattttat    2640
ctaaattacc actgaaagag gctgcaaaaa ctagtgtttt gtctaccaag tggaggtgca    2700
tctggttgac gtgccccaga ttgtgttttg atggtcttgc gatgttcaaa tgcgaaaggg    2760
gtgaactgtt cttacacgct cggcaattca ttgctcaggt taatgctgtt ttgcaaaaat    2820
accagggaga agtggttgag gaatttcata tcagatttga ttttcacagc ataccagctc    2880
attatcttga taattgggtt atcttttcct tgtcatctaa gatgaagaat ctagctttag    2940
atctgcaaac caatgatatt gaacgatatc ctgcacgcta caaattcccc tttgaacttt    3000
tggacagtgg aagcttgtcc ggtctacaac atgtgcagtt cagttttgta tctatcaaac    3060
caccttccaa gttcagaggt ttccctaacc tgagaaagct tgatctgcaa cttctagatg    3120
cctcttcaaa ggattttgaa actatgctgt caaattgcaa acttcttgaa tggctaagca    3180
tggacagatg ccgcctgaat ggtgaactta gggtaggtag tccattgccc cgtctggtat    3240
acctacaagt tgtgtactgc caagtaacca agatacaatt ccatgctgtg gagctagcta    3300
attttgtata taaggagac tttgtgccca tagccctcaa gcattcgttg aagctggaaa    3360
atgcaaacat caggttatat agtttgaatg atcggcatgc tatcagtgac ctggtaaaat    3420
gttttccgaa cttgcaaaat ctgaattttc acctttcttg gaacgatgca gaggtttgtt    3480
ctcagaaact aaccctccat gctacagttt tagcttgttt aacataatct agtgaatgat    3540 cttttgtcctt ttgttttcca gactaagttg ttatcagata caccttggaa gttttctcat    3600
```

-continued

```
ctcaggtact tgcggttgaa aaactttgca gattctggga tcgtggagac gaattttttt    3660
gtctcttttc tcagggctgc tccttttatt gagaagttag agatccatgt aagtgctctt    3720
atcagtaact actactattc tccaaactat ttcttcactt gtatgttgac atgtcatgta    3780
atactgatct cctttagta tcctgggtat accatgcagt aaaattaggt cagtctgctc    3840
acactggtcg ttcatgtctt ggttttagca tgttataatt gactgcatat ctgtgtattg    3900
tttctgagaa tctgtctctg cacaatatat ttttgtactt ctattcagaa aacaatttcg    3960
ccgttgttta cccaggagcg tttgcttagg ccgtgtttag ttcgtgtgcc aaatctttt    4020 tgaagtatac ggacacacat ttgaagtatt aaacgtagac taataacaaa acaaattata    4080
gattccgcct gtaaactgcg agacgaattt attaagccta attaatctgt tattagcaaa    4140
tgtttactgt agcatcacat tgtcaaatca tggtgtaatt aggctcaaaa gattcgtctc    4200
gcaatttaca tgcaaactgt gcaattggtt ttttaatgct ccatacatgt gtccaaacat    4260
ttgatgtgac agaattttg gaagtttgaa gggaactaaa cactgcctta gcaaggtttt    4320
ctttcaatag agtcaagtga gagtatacaa ttattacttt gcagagtggg tatattatcg    4380 tattttgca aaatttccca aacagcttca ctgcttatgt tacatctgga tacacacaaa    4440
catacagtta cattttcttt tttttaaaaa ataatgatga tgataacaat cactagatgc    4500
agtatgtatc atatcctagg tacacatata ttaaaggatg tggatctaaa cccagctgat    4560
cacatattgt tatgttttaa ccatgcagtt ttccatgaat ttattaatac tggatgaatc    4620
gcatgaggac catcctatca ggcaacaact tggacgctgt gaatacaata acctgaagaa    4680
catgcgtatc ataggatata aaggttcaag agatcaggtc gaatttcttc tacatgttgt    4740
ggagaatgcc cctgcacttg aggttttaac tctagaggca gctggaatag agtaccagga    4800
ggtttcattt gtgttgaatg aagcgtggat cgacagaatt actcagagtg ccgatagatc    4860
tgctctgatt gctcaacagt atctgaggga gaaacttagc tcaaagacac agctttgtat    4920
taagactact agttccagat agagctagcg ctctatgcaa gccatgtgaa aatagccatt    4980
```

<210> SEQ ID NO 17
<211> LENGTH: 3180
<212> TYPE: DNA
<213> ORGANISM: Oryza sativa
<300> PUBLICATION INFORMATION:
<308> DATABASE ACCESSION NUMBER: AJ243961
<309> DATABASE ENTRY DATE: AUG-1999
<313> RELEVANT RESIDUES: 19141 TO 22321

<400> SEQUENCE: 17

```
gtgatcctcg tctcctcctg gcggccgcag cgcgtgggtt cccaaatcgc gaaattttat      60
tttcccccaa aaaaccgaat aaagagaaat ctctccgagc gaattcgacg agatcggagg     120
ctcggatcga ggtaaatttt ctcctcgtat ttttctttcc ctgatcgatt gtgttgatta     180
ctggatctgg taatgctctc tgttgaagca tgcttgggta ggggacgtag atttgcgcga     240
cgaatcgagt atgttatgcg cgttttttcg cgggattttt cggggttttc catgcgcgtt     300
gcgggcgacg cccagcgctg cgttggattt gacttcgaat taagggcggc acggtggtag     360
attccacgct cgtttagttt ttgaagagtt agatctcgtt ccctacgttt cgaatttggt     420
cgcaggttgc taagatttcc cggtttgatc tgcttattag gtttactttt tgtatgtata     480
tgatcatgca atctcagatt tggtgatttg attattgtgc ggtgcgaagg ttctaggttg     540
acgtgttgtg gaggttgctt tgatcttatt ggagccaccc ttagcttatt cggcttgttt     600
```

-continued

```
tgatccgaat ttactattaa ttttggtgcg aattcagagt tcaataatcc tcttccgtag      660
catcgacttt ctcatctcta tgaaaaagtt tgtgggagt taatttagaa tcactggttt       720
gtttattata aatcgtcccc ttttctgata ggcaagtttg ctactgattt atatgaccat     780
gttagtaaca agtaccaacc cacctctttg tttgagttgg ctgtcagatt ctagatggaa     840
ttagatctgt gattgggagt tagtcttata agccttgtgc catttggctg ttccaattat     900
gtttaacatg aaaatttgga cttgttcagt ttcagctgaa gattttgatt ttttttttc       960
aggtattctc cttctgattt gattggattc gggatctgct ggcgggatc catctttagg      1020
taggatttca taattttatg gactttgatt gcaaaacggc aagaggagac tcttcatctg     1080
tgaatcgttc atgcattgtc actgaaggca ctgtcgtcca ggcaaagccc gtttctcaca    1140
acgggaaagc taaacactgg aatagcctca gtacattgaa taaccagaag tgcagttatg   1200
aattactttc cgacccaaag aaaaatgttg aaacaagtga tggtgagacc gcctcaaagt   1260
gtgactcatg gtgcttcact gatttgccat ccgcattggt ctgtgaagtg cttgaacacc    1320
tcgatccaaa ggaacttggc attgtatctt gcgtctccac cctactgcat accctagcca    1380
cagatcatca ggggtggaag aagttctact gtgaaaggtg ggggattcct actcctccag    1440
tcaccctcaa tgggcccttg gttccaggag gaacttcaga ttggaagtct tggaaaacat   1500
tatttgtgga gcgggagttt cgaagtaaat cattcatggg aagattcagt gtggatgttc   1560
tccgtgacca cagtgaggat gtacgcactg tgttccttct agcatcagta aatctgatat    1620
ttactggtgg taatgactct gtgatccgaa tgtgggactt ggaggaaggg cttttgattg   1680
ataagtcccg cccactttgt tgcaccatcc gggccattgc agctgacact aggcttttgg   1740
tcactgcagg aaccaatgcc tttattcatt gttggagggc tgttgaaggt aattcttacc    1800
cttttccacat ctctgggaat ggcactgacc agagtcctga gtttcgcctt tgggggcatg   1860
aaggacctgt gacttgtctt gccttggatt cattgaggat tttcagtggt agctgggata   1920
tgactgtccg tgtttgggac agatccgaaa tgaaatgtgt tcagaagttc atgcatgcag   1980
attgggtttg gagcgtggca cctcatggaa atactgttgc cagtacagct ggtagggatg   2040
cctatgtatg ggatatcagg agtggtgagt tggaaaatgt tatttccaat gcccattatg    2100
gtaatgcatt ttcttagct cgaacacacc tagctgatgt gctgtttacc ggaggagagg      2160
atggggcaat tcgcctgttc aatgtttctg aggtctctga tgatgaagat attaagccag    2220
ctgctacttg ggttccacat accggccctg ttcattccct cgcttttgag tatccatggc    2280
ttgtctcagc ctctagtgat ggcagggttg cactgattga tttgaggaag cttctgaccc   2340
caagaaagtc atcaaaacaa ccattcaggg ttaagaactt tgatccaagt tccattgaac   2400
ctccacagag aatgcttcat ggctttgggt gcgatctttt ttctgtcgcc attggtgcag   2460
acaggattgt ctgtggaggc gaggatggcg ctgtcaaagt ctggaacttc tcagaagcac    2520
tggagattga aagagggca caagctctaa gaagtatgag gcaggagaac cgcatgaggc    2580
gaaaaaggc acaagtagag atgaatgcaa atggtagaag gtctgaccaa tgtggctcaa      2640
tagccatgaa aagaaaccaa ctgaagggtg ataagagtgt cacttggcac agcaagcgtg    2700
ccatcaatga taaggtcaag tcttagatta ggattcgtac ccttcacaac tttacactct    2760
acagtagcca tgagttgata gttctttttct tggaagtacc tttgctgatc ccaattaggc  2820
ttgctgtgta ggttaacatt ggcatttttca ctattgaatt ttataaggtt accaatgcag    2880
tgtagccatg catgaaatcc gcatatgcaa ttcttattcg atatggcata tattgatcta    2940
acagaagctc tcattgtctt actgttttga gctctagttg catttgggtt ttgttcgtat      3000
```

-continued

| | |
|---|---|
| ctttctgctg gtagctgtta tgaatgggaa tctacattga actattccag gaataataag | 3060 |
| cttctgtaat tatgtcactg ctggattctt agaacattac ttttgctgtt acgtggtctg | 3120 |
| caataagaaa atcctgcatt ccaactcata ttttgaagat ggattttccc catctgctct | 3180 |

<210> SEQ ID NO 18
<211> LENGTH: 1800
<212> TYPE: DNA
<213> ORGANISM: Oryza sativa
<300> PUBLICATION INFORMATION:
<308> DATABASE ACCESSION NUMBER: AJ243961
<309> DATABASE ENTRY DATE: AUG-1999
<313> RELEVANT RESIDUES: 31201 TO 33001

<400> SEQUENCE: 18

| | |
|---|---|
| ggatttctct ttcctgttta atacaaagag aaagaggacc tcaactttta gaaacaatac | 60 |
| catataattg aaaaggatcc aacccacaat ttgtgaagtc atgaaatcaa caggaaacga | 120 |
| aaattagaga atatatgtgc ttctcattgc tttaactgaa caaattaact aatggttcac | 180 |
| attctacttc taagaaaaaa aatgctctgc tgctcttcat atggttaact aaacaaccca | 240 |
| aattcttgca agtacttcac tgcaactatt ttttcctcc tttgaataag catatgtaag | 300 |
| ttttaaagag gtgttgcaaa tacctatgaa ctggttgtag ctcaaaagta gaatgtgcgt | 360 |
| ggaacttaca aattaactaa tgtatttcaa tataaggaag gttctgctat ccaagaattg | 420 |
| tgtatagtag agataaacaa gcaacatgac gttacaccta aaaatgggaa ctttcctgaa | 480 |
| tataataaga tccttagatc ctcaccatat gagaaaaaag atagtaacta ctacgggcaa | 540 |
| atgacatcga taatcagcat tgaaaacact cataacatca gtttcagtgg aagtcgctct | 600 |
| ggtggagcaa ccctggcact acagtgtatg tggtaaaacg aaaatattat cacaaatgat | 660 |
| gaaaatacta gtctctgttc ctcatctttg gtgagcatat ccaccatcac agaattttag | 720 |
| agtaatttta ctcatggtaa tagaatttct gttcagcaat ctggtagcaa tttcaatttc | 780 |
| aactcatcta agcagtttcc ccgaataacg ccgctttaat ggagaactca atctgacact | 840 |
| agttgtataa ttagagggaa aaaatgaat atgcgtaatg cagaaacact attgcgaatt | 900 |
| tagtcactga caaacctagg gcacttttag tcgaaatgca tattttttctt actactaaga | 960 |
| ttccaaggac aaaccactaa gacaaatcta agtagccaat caaaatcatg aacaaaaacc | 1020 |
| cgacgaacaa tggaaaattc caaccttttt tacagcccag cacaaaactt tatccaagtc | 1080 |
| gcaattggga ccaataaggc agcacttaat aataaacagc aagataaaaa ttttatcccc | 1140 |
| taatttgcca atgggactaa tagcgcaaca cttaataatc atcatcatca tcaacaaaaa | 1200 |
| caacaatggg accaataact cagctcttaa taatcaacaa caacaagagt aatcctaaat | 1260 |
| cctgccgtgc cgcagcctcc gcccaccagc cacgccacct cgcactgcat cgccgcctcc | 1320 |
| gcctgttgct ctgctctgcg gctctgctag ggttcaacaa ctcgggggaa ccccacagtc | 1380 |
| agcaagtaaa aggaagcccg atatagccca ctggtacgac ccagcatcac aaagtccctc | 1440 |
| tccgcctctc ctcatcaatc gctcgcagct ctcccttca tggcgatacg gaggacggca | 1500 |
| tcgaggttcc ggttcggggg caggcggcga gatcgaggta cggcgaggtc tccggcacat | 1560 |
| gagcacacac ggcagcagaa aagaaaaaa aattgaaggg tacaaagcca agagtaaac | 1620 |
| taacctatgc ctcgagagca cctcctcgag cgtctcttgc tgcgattcct gcgctggctc | 1680 |
| cgccgcggct gcctcgccgc cgccgccgcc gccgccgccg gcggattcgt cggctagggt | 1740 |
| ttcgtccatt ggcaaacgat gcaaaactca gttcaggcga aggaaaaaga aaagagaaaa | 1800 |

<210> SEQ ID NO 19
<211> LENGTH: 5040
<212> TYPE: DNA
<213> ORGANISM: Oryza sativa
<300> PUBLICATION INFORMATION:
<308> DATABASE ACCESSION NUMBER: AJ245900
<309> DATABASE ENTRY DATE: AUG-1999
<313> RELEVANT RESIDUES: 13561 TO 18601

<400> SEQUENCE: 19

| | | | | | |
|---|---|---|---|---|---|
| gttcctcagg | tctagcctgg | tcctgcacaa | aagacataca | gcatataatg | attgatattt | 60 |
| aactcgttca | attgatcgac | caaaacatgg | caatggctct | cgaatcaaac | aaataaaaca | 120 |
| gaggaaataa | aagggtact | gtggatatgt | cttatacttt | cctaacaatc | tcttactata | 180 |
| ttggaatcac | agctaatttc | tttgaaaca | cttaccgttg | gtaataaaag | agggaagcat | 240 |
| actttgtcaa | ggaaaaccgg | gaaaatacac | ccccatgtac | tacaaacttt | taccattttc | 300 |
| acacctattt | tggacatttt | aaagagaaac | aaccattgtt | tctcaaatga | ttttcagaat | 360 |
| gagacaaaca | ctgcataata | ataataacct | ttcatttcaa | ataaaagaga | caaaaaatga | 420 |
| tgagattgtc | ctttgttatg | ttatactctt | aagtcaaaat | gagaagttca | ctatagagaa | 480 |
| acagcttata | acttataagt | aaagtgattt | atcaacaaac | ctctagcaga | cccaggtgca | 540 |
| ccttcacgtt | ggctcatatg | gggcgcgagc | atctccatca | cagctctcat | agcgtctgca | 600 |
| gcctgctctg | gtcctgccaa | gtttatttgg | atgccagcat | ccctgtgcat | gcctggttgg | 660 |
| ccatgctccc | cttcatgtcc | acttgaagtt | tgttgtgggc | gatttccttc | agtagagccc | 720 |
| gtgaacgaaa | aaggaggagg | gactgcagta | ttggttggaa | agaaggagg | tggggtatgg | 780 |
| ttacttgaag | tctctgtctg | aggtgttcct | tgactgttcc | cattgacatt | tgcatgatta | 840 |
| aaaatgtcat | tcaaatttat | atttatggaa | tgctcagatg | attgttgact | gatatcagac | 900 |
| acacggttga | tgatattggc | gaagaactca | ggagttggag | aatttccagg | aggaaaaaac | 960 |
| gtgaatggaa | caccactgct | tgattgacca | ggaaactgtc | catgtgatgc | ttgactttgg | 1020 |
| ggtgcgtatg | tattctatac | acaacaaaac | tgatcagttg | gtaattttga | aaggacaaag | 1080 |
| aaatcccca | aaagaatgaa | tttcatgtaa | tcaaacaata | tcagcattct | atacctataa | 1140 |
| ccgaagttcc | aattaggagt | tttaaatgca | caaattagtt | tctaaaaaga | aaacaatgga | 1200 |
| ctgtatgttt | gccagaggta | ggacatatct | caaagtccag | taaaaagcac | acgtggtttc | 1260 |
| cagttacagt | acctgttctt | ctggtggacc | tcgctgttca | gccagcttct | ttttggtaac | 1320 |
| ctaaagttca | ggcatagagc | agggataaaa | attccatcag | ccattagcga | gagtagcatg | 1380 |
| aaacaagctt | tatccagtta | atgaaaataa | gagcataaaa | acaataccct | gatattctgc | 1440 |
| cggacatttt | cattactagg | atcaagctcg | gaggctgcaa | gaagaaaaac | aagttcatta | 1500 |
| tgcacccacg | cgttacttta | ctggatatac | taaatgcaaa | atgtagattc | atgccagaat | 1560 |
| ggcaaccaga | acaagttggc | atccagaaca | agttaatttg | atctagaaaa | atgaggaata | 1620 |
| taataatcag | tagacattag | aagcaatgaa | ggttgaaagt | atgtgtttga | tgtgaatcag | 1680 |
| agtctacaca | gtgctgaaag | catgtggcat | ggattgcgct | gcactagcga | ccttgaccac | 1740 |
| aaaggcaatt | aattacataa | agatctctta | aaaggataca | ccagaagaaa | ctgaagggta | 1800 |
| gatatgtaag | gttgtatgta | aaaaaatcag | cttttcagac | cacaattcaa | ataagcagca | 1860 |
| gctttcccag | aaaaaaaaat | gtaacagatg | taaaaacagt | gtatagcaga | atgtatcaca | 1920 |
| ggttcagcaa | aactaactga | gacttatgga | ttgcctacct | ttcaaatatc | ccttgtacaa | 1980 |
| agcatcgtgg | tattttccca | aagcaaaata | agcagatcca | agtcggctgt | atgctttact | 2040 |

```
gtagttaggg tcaatttcaa ttgacttcag gcaatcctca acagcttcat tgaacatatt      2100
aagaagggta tatgcagcag ccctggaagt aacatgtact tttcaatttt tcatgttaca      2160
ttggatcaaa gcaatgtatg aagcagataa atgctcttgt gagaaacaag tgcatagttg      2220
taaggcagta aggattgtta acaccgctac cataacaaga gtaaaagacg ttaggttaac      2280
gttaggttaa caagagtaag aacttgacaa ttatatatca actttccccc aaaaaaaagg      2340
gcccatgggc catggcacgt acgatttgta accagctgca gctggcttcc actgttttaa      2400
gatgtttgta ccggtgggaa gaataataac agatcctgag attactaacc acatcatagc      2460
ttatagcagc actagaaata gcaatgtgag gatttttgggg taacatagta ttttatatct      2520
gtacttactg gttctggcat tctagactgg attcactatt agccactaag ccatctcaag      2580
atcccatgtt acatagaact actcaggaaa acggttgaaa taacccaagt tttgtttagt      2640
tccattaatt cttacccctta tccctaagag ttactcagtt atgctgaaag agacaacaac      2700
tgcacagtgc atcctacata ttaccaaaa aggtcatcat aaatgtcatt aatttgtgca      2760
tacctgttac aatagtaaat agcattattt cggctcaacg caatagcaca ggtgtacagt      2820
tctacagctt taagatgttg ttttgacctc atgaattcat tacctgataa acagacatgc      2880
agttagctac agaaggcttg aactgcaaaa taattagctc tttttacatt gataaatgaa      2940
aaaaaatgaa gattttcaa gtaagaattt ttagttaaag ttaaaaaaag caggaaggtg      3000
taaagtggtt cactacccaa tgaacaaatt atgctatgct aaagaaaatg cacaagtgaa      3060
aagacaaagg gttgtggata aatacctttt gacttgaaga attctgcaag gtctcctaag      3120
cttgcccttt tccttcctga cttccgcatc ccctaaacag aggtgcattg tacctcatat      3180
cataattaaa aaaacactag actataagcg aaacaagaaa aaagtagcat gcagtccaac      3240
agtcgccgat ctcttcgtcc aagtagtgcc actacccaag ttgcctagtc atttaagaga      3300
atctccatga aacaggggac agtcctagat aacaagggga gcatctggga taacttttcc      3360
ttggtaacag ggtgtaggga caatacaatc atgatccatt attgtgcttt aaaagagcgc      3420
gagttagaca agtaaatatc acatattata ccagcaatgc atcatcgaag aattgtgttg      3480
cttttgaaag ctggccagga tcttcagctc cagcagatga tgttttaaag aaattgattt      3540
catcaagcga agtatagaat tttgcaaaca gttcatctcc tgaatgatct gatcaaatag      3600
caaaatcaag ttgcatgagt aaacactgat ttcaagtgaa tgattttcc tacatttgtt      3660 attactcagt aggaaataac accatttaca aaaacaagct taatatttcc agcattatct      3720
ggacatctga tcatagagac aaccaacagt ttatgctata gtcataccta agtcgaaggt      3780
atcttcattt tggccttcac tctggtaagg agaggcagaa gtcagtatga gaagctaata      3840
tttcttatta aggttgttaa aggatataac aaaccatggt gaacaagact tgatgtatga      3900
cattactagg atgtaaaatt atagccataa tgtaattcca aacgtatgca tgatgttatg      3960
tcaatatgtt tgtctttata tatatatata tatatatata tatatatata tatatatata      4020
tatatatata gcttggcatg gaataagacg gatggcggtg attaagcgtg tgacaatgtg      4080
tgtgtgtggt gattgagaga gagagagaga ggagaccata catttgatgt tgtacattta      4140
gtcaggtctt cttggatagt tgaagtgctc gcactgcaag aaggtttgtt ggataccggg      4200
ccgggtgcag agctatcttg ttgagcagct tccatagagc taaagagttc aagtagaagt      4260
cctggatgta ccctttcaac aacagatgaa gagttgatac tgaaaatgga ttccatacat      4320
tccctggcaa cctcaagagc ttcaggatca gccccaggag ctaactcaac tgcatagcaa      4380
```

-continued

```
acagaattcc aatgtcagga gaaccaatgg cttttgcaaca ctgcacatct ttgattccaa    4440
aaaaggggag ctaagctggt aattaatttt gtctctactg tgctttttt ttttgtgtgg      4500 gagggaaatc ttgcatattg tgctgcttta gatttggatg gtgattatcg aaaatattat    4560
agcctactac tgtagctaac tagttagtaa ttagcaaatt caatggtgct tcgcatcgat    4620
gtgcgaaatg gctccatcta gagatagaag aaaaagggca agtagtaatc cgcaacctat    4680
acacgcgact ccaataaagc ggaaatggga tttagggcag gcgtatggga tgggatggaa    4740
ccctggtagt agtagagtct tgtcgaagca taatgatccg aagcgaagca tgttggtggg    4800
cggttgcaag ggaagtagtc cgattgggtt gatcgatccg cagcagcaag caacccatac    4860
tatactagta ctagttcgct cgcaggaaaa cagtaaaatc gagcgtgatt tagtgagaag    4920
agaaaagggg atgggagacg ggagacggga gtagtgaccg gagttgagga aatcgaggaa    4980
ggagaggacg atgaggcggg agatggggga gtcggagcgg gtcatgttcc ccatcgccgc    5040
```

<210> SEQ ID NO 20
<211> LENGTH: 7800
<212> TYPE: DNA
<213> ORGANISM: Oryza sativa
<300> PUBLICATION INFORMATION:
<308> DATABASE ACCESSION NUMBER: AJ245900
<309> DATABASE ENTRY DATE: AUG-1999
<313> RELEVANT RESIDUES: 47761 TO 55561

<400> SEQUENCE: 20

```
tggaggtgat ccgaggagca ggtgataata atgaatgaat atgatggatt cagaggtaaa      60
tgcaggactt gtcgagggag atgggcttgt tgagcttggc ggggttcatg aggaccttgc     120
actcgatggc gcgtgtgaac ttgggcttca ccagcgcccc cagcacgtac gccctcgagt     180
gcaccgtcgt cctcaggatc atcggcaccg gagccatgct gccgctgccc ttccccgccg     240
tcagcgtcgg ccctccgccg tacagcggca ccttgttccc catcaccccc acgctcaccg     300
tcctccggct gctccgggcc tggtagaact tgttgagatc gccggacgcc agcgtcagct     360
ggctgtacga cagcgtgaac gggtccgccg tcacgtggat cccgaagaac gtgcccgtgt     420
tccggtacgt cagcttcacc gtcgagttgg tcgtcgccat gtccgtcggc accagcgacg     480
cgtccgtccc cgcctggatt atgaagttct cgaacgtgat gctctgcaat ataatcaaca     540
gtaccattat ttatttgtca tttcattcta cgaagcacta atcaaatgaa gaagaaagaa     600
gaatagttac cttgatgact atctgtggct tctgggagcg gctggcgccc cagaggacga     660
gggcgaagaa ggagaagagg acgacgaagc cgaggacgaa gatgaggaag tacttgcagc     720
gcttggggat gccctgcgc tcgtcctcgt cgtcgaggag gccctcctcc tcgatcacgc      780
cgatctcctg ccacccttc cccgccgggg cgccttgcg gccggagctg gacttgtcgc       840
ccttgcgctt ggggtggccg gagaagcggc tggacgagga gtccctgccc accgagtgcc     900
gcggcgaccc catgggcgctc agcgccgcg tcgagtgcac cgacgtcgcc gtcttctccc     960
cgtcatgcga gtccctcgac gggctctgca cgtagtacac cggccgcccg ccgcgcgacg    1020 tcgggaccg cggcggcgac gatggcgcca ggctcgtcac ctccgagtcc gtcttggcgt     1080
gcatcttcct cgtcttcttc ttcttgatct ggcagtggag ctcgctaaca ctagctaagc    1140
taatgaccac tccgtggtag gagtaatact aataactata gagaagagat tcctaaatct    1200
aatacagtga tgactagcac tagtagtacg tgacaaaggc aggaaggccg cggctaatta    1260
aagaatagga aagcaaagga agcagcgtgt gttagttgga tcaaagcgtc ggtgctcttt    1320
ggactctgga ggccaactaa ttttagtttt ctttttcaga tactagctag cagcactact    1380
```

```
agtggagtac aaacattgca ctaccatgca taattagtat ttagttttac acttggtttg    1440
tagcacatta taccttcaaa aaagaatcat ttttagtcta taaaaatgaa gttatatcct    1500
actactatct attggaggaa agtactacta gtatttattc tctaggatta ttaacaggct    1560
aatgtggggg gtgaaaatga aaatgaaaat gcaaattttc cgtataaagt gggtggttgc    1620
atgttacacg gaagtgagca gagcactggt atggccatgt gacggtgatg tgccgggatt    1680
cgtcggttgc ggcatgagag agagagagag ccggacggac cgacagttca tgcgaggctg    1740
gctttcccat tcctagccag ctcaccatct cgcactcgct cgcagctgga tcttgctttc    1800
ctctcacctc ttctgccctg ccctacccta ccattccctc ccagtcccac acatacacct    1860
accatctact gcttgtaatt acagagtata catgtcacag tcaaaagccc tcattgcaag    1920
caaccacatg ttgcatactc ctatgtgttt aattagagtc tcttcttcca accaccatta    1980
atcacttgac acaaataatt aaagacaat tgtgcggcac caaccgctga ccataaaaag    2040
gtagtttatg catctccatc tccatctcat caacaactaa cagcaatcag agaaacaaaa    2100
gaaaaggagc atatatcatc agcatgcatc cagcaaggat gggatctcga ggttttgtct    2160
ggatttgttt ctctgcccac tggcccaaaa cctcgtgccg cttgcaacca tttgccaaca    2220
agctcacagt gacatgtctc acagcaaaag aaaaaaaaaa tacaaacaag aaaacacacc    2280
gtcgcagtaa cagttctata agaattgca aagtacggac ttgagaaacc agaacagcag    2340
atctggtaaa attaatctgc aacaccatat aatagtatgt gcatgcatgg ttttgcctcc    2400
agtatcaacc aataataaca gtagtcttcg cttctggctt ctgactttgc cacaccaacc    2460
aaccacacta cacagacagc agcaaattgc acatcatacc atctgccaat tcactctcac    2520
caaaacttaa ttttcaccag aagctgctct cggtataagt cggatgctat gacttgcttc    2580
accgtgaaag cacgtacgca acagagaggc ctcaagaata tgatagagca aaaatttcat    2640
ggctacaagt gaaccgcaat gacgtggagt catagggttt ccggcggaga gtgagcctgg    2700
ccaccttcaa gtaacatgct gcggctgcag tatgatcttg ttgtgctcga ggaggaatgg    2760
agagacctca tgtcgccact gtgcggaatc agctcgttcc ggtggacgcc acatttgctg    2820
ttccgaggat aaaatccccc ttctgcatct tccatgcctt cgccaaagct gccattccct    2880
ggatccagcc tctccgagag catcctgagt acttgtctaa tggatggcct ctcccgccct    2940
tctctctggg tacaccattg acaatgcta actaccaaat gcagctgatc catgtcaacc    3000
aagcccctga tcgttggtcc acaaattcag gtgtgatctt tccggatgat aagtgtccct    3060
gtgcccactc aaccaaattc ctgctgtctt ggattgctct ccgaccagta acaagctcca    3120
gtaggagcac accatagctg tatatatcac tcttctctgt caattcttga gttatcacat    3180
attcaggatc catgtaccct gcagttgatt cagtaagaga gatgagcaaa ttgtcctcaa    3240
tgttcgtgta tggagagtgc catttctcaa atctatttta cattaatgca atctcgtaac    3300
agttgtcaac tgttctccta ttactcaatg cagatccgtg gtaaaatatc actaaaaatg    3360
attttttagg caataaatat gaattcaatc tgctaaatag ctattttaat ttaatcatgt    3420
tataaaattt acctggggtc cctcttatat ctgtgttgac agcttcaaag ctgatggcgc    3480
cagttcttga tgcatgtgca aggccaaaat cagcaaccta atacaagat tcagcagggt    3540 ttttcagcga cggcaaatca ttacagccag aagttatcat catatcacat gaccaaacct    3600
tggcaacaaa attctcatct aaagaatgt tgctcgactt gatgtctcta tggcagagtg    3660
gagggttaca aagaaaatgg agatattcct gcatgacgaa caaacatgat tatccaccat    3720
```

```
aatgcaggta atatgtacag aaaagggagt tatatgcgat gcacaaatac gtgaaatatc    3780
aatgaacttt attgaacata gctcaattgc tccaagtgta attctggaca acaaaatcca    3840
ggaattttca ccctggttct tctcaaagtg cattacataa tggcaggtaa acaagcaatg    3900
ccagctcaag ccagaagaaa gcagatggaa aaaacatagt actccgtccg tttcatatta    3960
taagtcactt tgactttttt cttagtcaaa cttatttaag tttgaccaaa ttcatagaaa    4020
aatttagcaa catctataac accaaactag ttttattgaa actaaaattt aatatatttt    4080
gatggtttgt tttatgttga aaatgttgct atatatttct ataaacttgg ttaaacttaa    4140
agaagtttga ctaagaaaaa agtcatatcg acttataata tgaaacggac ggaataacac    4200
attgggagtt accagtccga agcaacgttc tacagtccaa aacaagttca gaacttcaaa    4260
tgcctcagct tgagtaaagt aggctatgtg taattagtca atgataccct ctctcgacac    4320
gatgggctta gggcagaagt gcaaaagcta atttgtgaaa tgcaaagaaa gcaccataat    4380
tccagaccac tgaagatttc tttagtagca aatggtccac aaaaaaaaag gtcaaccatg    4440
tcaaattgac aagttatata cagcaggacc acatacaaaa gtcagaacaa tatttattgg    4500
tcagtagttt tatactcgtc acaatatttc ccatgcaaac aagaatggct gctcgtcaca    4560
atatttccca tgcaaacaag aatggctgat cctcctacat gctactgtag cagtggctca    4620
cctagaaatt gagcccagga gggggcaaaa tgctatcacg ttcttctaca cgaaataatg    4680
tactccctcc attccaaaat ataagaactt ctagcatttg aatcttgtta aaaaaatcta    4740
aggatttcta gcactatgca cagtactact tgttccatta atcacatccc attcaatttt    4800
tttcccatat taccccctcc tatccatatt tattgagggg cgctaaagtc ttttcttctc    4860
aatcttaatc tccactaaac aacctagaaa tccttataag agggagtaca ttattagatc    4920
aaattgcaaa ataggacttt cagacagggg caatctctaa aaaatggatt tgatgtcttc    4980
tcaaacttta gtaccagtat ttgagaaact aaaacttcag tagacttcta tcttgttgag    5040
accagaagag gaggcaagag atgtgtgttt ctcgcgctga ttcaataata acttttttttt   5100 ctcatgagaa attccgttgt gatttctcac ctagtatctc atgaagtgca cttttcatct    5160
agatgctgta gcagctttaa tatgtgcact tcactggaat caaataatgt cattaaccta    5220
ggcccaaaag gtaaagcaac aaaatttgag cacagatcta gtgttaagta aacaacagt     5280 taaaaactgc aggtgctaga gcagtgttga actgtagaga cccaacttga tgtatgcttg    5340
ctcaatggtg catttctcat gttttgacta aactacacaa aaggacattc ataaggccaa    5400
ggaagcagat tcattaacta aagcaaacat accagagcat tggccacatc cattgcaatc    5460
tgtagtctag actgccagct taatgccttt cttccagatg ctgtagcaat tcaaattgga    5520
caacttaaca gcaattaaaa aatataaatt atatgtacag aagattcaag atatacaaag    5580
caatcataca gtgtaggtga tcctttaggc ttccgtttgc catgtactca tagacaagaa    5640
acctgacaag tacatatata atatgaccac agtgtaaaat ctgtacttct gtagtacaat    5700
aggacaaaaa gataccagcg tacctttctt tcctttcgat acagaagccc ttgagggtta    5760
caagatggcg atgatgcaac ctagctaaaa gctccatttc tcggcagaat tcttcctcag    5820
cttgtcttga taccttgtcc atccttttta cggcagctat agatccatca ctaaattgag    5880 cttttgtagac tgttccaaaa cctccctttc caataactgt gctgaaattg ttcgttgctt    5940
tcattgtctc tttgtaactg tacctttgga acattggtga ttgacctgaa agaaggtaa    6000 cactttggtt tcgataagag acaacagaat gatgaggtga tcggtttagt ttttattact    6060
gccatgctaa agcccaaagc tatacttgtt gatgcacaac attataactc ataaatagca    6120
```

-continued

```
gactttcttt tagattttt ttcacataac aggtttgacg caggaatgca taaagcagtt      6180
gataaacagt gatattagaa catcttatgc gcgcatcaac attgggcata acaacgtagc      6240
gtaagaacct aagcaagttt caggcagaca tcacactatc tgattaccat gatttactga      6300
ccataaacaa gctaagacca aattccacct ttttactagc ttaaagcatt tttagtaatg      6360
tgaaatatgg tgttagatat agattagttg aatagaatca agtgcacaaa ccttctggac      6420
atctccagga ttgactctga cagaatgcat tttctgggtt ctgagcatga aggtctgcat      6480
ttttcaattc cctgttcttt ctacgaatca atatgactaa gacaagttgg agcagaacag      6540
caagcaatat aaccgctatc cctatcccag gtatcactgt aatccggtaa ggctggtgat      6600
gtttctgcag aacagttttg gtctttggag ctggagcatc aacagggttg tcacatttg       6660 gagaagaagc tggagtcgat gtaacagatg atggccctgg taaattcccc aagttagaga      6720
gtggtcatct ttaaacttaa tcagaatgca tcagtagtaa gttagtaata cctggaaaaa      6780
ttgtgatccc ttgtacaccg aagaagcact tgacaatgtc gtcgtaagag aaaatgccct      6840
gttgagttgc aagcgtgaca aaaccgcgt tccgacagac gctaagacca acgttatcat      6900
ccgagccaat gaggcgatgc aagtaaacaa tgccgtaatt caagcaggtc ttgcaagtga      6960
tatccaagga tagaggaccc ctgcagcttc caacaacgtc attgaaattt ggggattgca      7020
acatttcaag gacggtgtca cgtccggcac actgatatga gacccttatc ttgggtccca      7080
gcccgcagaa gacatcggca tcggtgggga ttccccgtag cttgaatgtc tcggatacag      7140
agctaagaca tatctcagag aaggccgag ggacacccag cctgccggtg gcattggcgt       7200
agcgagccat ggaaatggcg acgaatgcat tgatgtatcg gcagcatgcc gcccgctgcg      7260
tgggatcaga gcacgcggct gaagctaatg tgaagttggc ccaactaaaa tccaaagggc      7320
aatctgcaga gaaacgcggt ggatttagta gagagaaaag tagtgctagt aattgggaag      7380
caacagaaaa tgggtaagcg tctgatgatg tgcattgaat caagtgagta ggaactcagg      7440
tagaagaaga aaacgtgcag ttatcaagtg agtagcaatt aagcggcatg aaacactggg      7500
cattatattc gtactacaga agatggggat ggtatatagg gttgggaaga tcaaatcggg      7560
catgagcagt atcgaaagca ggaaggcagg tagtgattag tacagtaatc agtcgcatgg      7620
ggagcggatc acaaatactg ctactctgct agagtaaata aggcaatcga tggatggaga      7680
aggtaactga cctccgacgg cggttgctgc ggggttggcg gagaagaaga agggggaggc      7740
gagcaggagc aggacgacgg agacgaggcc gccgcggagg aggggcattt ggctggatgg      7800
```

<210> SEQ ID NO 21
<211> LENGTH: 5640
<212> TYPE: DNA
<213> ORGANISM: Oryza sativa
<300> PUBLICATION INFORMATION:
<308> DATABASE ACCESSION NUMBER: AP000367
<309> DATABASE ENTRY DATE: JUL-1999
<313> RELEVANT RESIDUES: 92341 TO 97981

<400> SEQUENCE: 21

```
aaaaaaaaaa aaaaaacgca gccgtgtagg cgtgtgtagc ttcaagcagc aaccttcttg        60
cagtggttct ccagccactc catggtgaca ctcttcggtc tttcgagcgg caggccaaga       120
gcacggtccc aaatgagctg cgacacagat aatgtgaaaa aattggttga tagaatgaag       180
aaggatcctc tgcattgtag tacaaaatgc agagaagatc caaagaaatg aggtagaaag       240
tggaaagtga gagatacctg agatcctatt ccaatgctcc ttgaaactcc gaaaagaaca       300
```

```
gtgtaatacc tgcgcagtta gagaagtttt cttaagtact cgttctaaag ttagatttgc    360
tactctatca taagttcaag attaaattag acatggcatt agattgttta accaatacag    420
ataaacatac cgagcttcag ataatccaaa gtggttcagt agaactccgc tgtgagcatc    480
aacattaggc catgggtttt tgacctgaaa atgtgaagga tgttcttatt tcttagccaa    540
tgagatggaa gtaaactgaa ggagccgtaa ttaaaggagc ataattatt gatcaatcta     600 gtagcattac cttgccaagc tcagtgagga taggaggcac aacttcatac aacttggaga    660
cctgaaagag gataggtcga tataaatcct attgagacag tgggactgaa gagagccatg    720
cagctagaat ttagactaac cagttggaaa agtggatcct caggcaagta cttcaaagca    780
aactccctct gacatgtata ccgtggatcg gtcttacgta gaactccatg accaaagcca    840
ggaacaacct acgaatgaat gtgtcatggc atactatctg tgaattttc agttagagtt     900 caacaaaaag agaatgttta ttccagatca ttagaaatca tttgtttgta taatataagt    960
agctaaagaa aacagatcca atataacata acaaacttag aaccactgct tagcaatgaa    1020
ctctcagaaa gttgagtttt catttcagtt aaaacatgat gatatgcact tcctcatcaa    1080
atagaaatat aacacggaga taagctacct ttccactttt tagtgtcttc cacacatact    1140
ctttgagttg atcagttgta acgtcactac cagtctcacc tattacagat ttgatccaca    1200 acaaacttc ctgcattgga tgtgaactat ggttagttca cacacacaca ctaaaatatc     1260
aatttaaaaa tggaaggaac attatgttcc ttcttccaaa gataatctgc gacatatttt    1320
gagtatgcaa tgcagtgaat ccttgtttag caggatgtgg cagagaagat ccagtacaac    1380
aaactgagca tacctgatta gccaggccgt gcaacggtcc agctaaacca ttcagtgcag    1440
ctgcaaaaga aagataaggg tctgacagag cacttccaac ctgtaattga atatcatgag    1500
cacggaatga agaggtcagt gcccatagat gagtcatgag agagagagag agagaggcaa    1560
ttgccagcaa aagaaaataa gtcatagatc ataagtgata aatcctaaag ataacggatt    1620
gcaaggtttt ctgcggcaaa ttaagaggct accttgtact atcattacca cttctacctt    1680
gaagatagag attcagctaa ctggatcaag gatcacagcg caaccaatta tattaccttt    1740
cctaatgcat taaaaggcca tactgataca ccaggatttt cctagacata caatagctat    1800
ctagcagaaa tagatacata ttttcagtca tagctttgat gctattagac aataaaaatgt   1860 aagactaatg actccatgag tactaagcag atgatccttc aagataacag ttaaagtaat    1920
gaagaactca gctaaaagca gtttaagttt tagttttgtt cctagttcat attccttaaa    1980
atggctagtt tggtttatca gtgcttatta atatatctcc gatacatagt aataacagca    2040
aagcaaatca aaggcttaaa gtggcatcca gtgcaatagt gcatgccaaa agtgtaacat    2100
atgtaaaaag gcacaaggat gatgtagcag ccagaaatga tccattggca ggtttacaac    2160
aatagtggca atgctaacaa gaaaaaaact gcattgaaac cagaaataca aaaattacca    2220
gatgtccagt atgagcactg acgtttccac cttcatgatc actggaagaa cacaggtgaa    2280
aggaaaaaga aatcaaacca agtctttag aaataaatag aaactaaaac aaggatggaa     2340
tgaattacgt gtgatgttt atatatagtc gcatcaactc aagcattttg ggatcatcaa     2400
acccaagcat gtgtgaaaaa tttgctgcat aatccagtgc attatcagct gctatagttt    2460
tccctccctt gaatatcctt cagagaacca gaaaacggca ttattgctat tgcagttgaa    2520 aattttaca gattgcctgg taagtaaaga tggtgaatga attgataaaa agctacctcc     2580
ggtaaacata tgaagccact gctggaaggc gagctatcaa atttaagcaa tcttcatagg    2640
taggctccca gaacctatta aaatagcacc aggtcagtac atggaaaatc cattcaacaa    2700
```

```
ctaatgcaat tttggaggca gtataaatcc caagcatact ttgattttga cattcctttg   2760
tcataggctt tttgaaactc actctccacc tgcaaataag aattaaaata gaaaaggcaa   2820
attaattaag tgtggagacc tagaaagaat tacaaacagc aaaataagag ggttttatca   2880 atggatttttt tttaaatgat tgtcttttttt acatgcacca tctccaaaat aaatataccct   2940 tcaaataagt ggcaacagaa tatgtattta tttcagatga gtgatatatg ctacaaggtt   3000
tacctgaagt gccatcactc ctgtggtaaa ctgggtcatc ggatgagcag ttacaggaag   3060
agcatcgatt gcctcataca catgacctgc atccgtatca taagtcaatc gaataagtgc   3120
caagtaggta agtgggtaac atgccgtatg tttacagaag cacaaatttg taatgcagcc   3180
ctgagacata ttttttccaat gattgagtat acaaaaactc aaatcaactt atcacagatg   3240
aatacttaaa tgagctatat cattatcaaa ggcaggatta agaaaactga agtcaataga   3300
gaacatcatg gaacagtccc aaaaaaaaaa ctttctacag ttgcctttca aatttcaact   3360
acacttgccc agcaaaaaaa aataataata aatcaaatac acttaagaat ataggcttaa   3420
gttaacaaca tttcatattt tcaggcaatt gaagagttta accttaaaag ctcagattac   3480
tatcagaaat tcataatgca gtagcttcaa tttatttttca aattgactaa ctaaagaacc   3540
atctggggga acattataca agaaacttgg tgtgtttatg gtacttgcag aataaagctt   3600
cgtaggaaca aaaactccat aatctctgta tgtatccgtg actatatttt ttatcttcta   3660
agaaaaggga aataagataa tgacataaaa ctcatctagg tttttttact aattgagcaa   3720
acaataatgc aataaaccag aagagacaat tgcagacctg gaacactcga acgactagcc   3780
aattcctttg atagagcatc aacttgctct ttggttggca cctgaaacaa acaaataccct   3840 atcagtccac actagcagct aaatgccgac aaaaataaga acaggaaaac caagtttaca   3900
agaaaaacag ttaaacaaaa gaagccaaac cttttccggtc aaaagaagcc aaagtagacc   3960
ctcaggcaaa ggctcccccat cttttaactgc tgtcggcagc actttctggc actctggaat   4020
cgagagaccc ctaaaacgaa taccctggat aggaaagagg tacagactta catccaacag   4080
caagatatag agtgatgcac gtttaaattt cacaaagtca aactaagcta aaaatctaac   4140
ttaaaatctg cagaaaagcc gccatcctaa aaaataaatc ataaaagcat caaactcttg   4200
taatgaagca cattcctaca taatgactat agaaatctag actatttagt ccctgtacct   4260
cttttaaatc aatgtgctaa agttgattac agaacttgat tcagattgac aaatatgagc   4320
aatcattgtg tcattcctac tgtgcactga acggatcatg ctcaactgtt agtcacttg   4380 cttggagatc atgaaaatat ggtgattcat cattcatcta ttttattttc caacttttgc   4440
acattccaat ttcaagatat acatagacaa aatatccaaa tttgcttcta tattatgcca   4500
ttatggtatc gtagcattat agtttacaag catacctcat ccgggtcaag caatgatgtt   4560
tcccaaagca ttccagtcat ccctctcatc ccaccaagga ccttggataa acaccattta   4620
agattttaga ccaatcaata aaggacaccc ttgagaaaca atccataaat aatcaatacc   4680
aaaagcatac catatcgact gttatatttc caagttggac ctttccatgc tccgatttaa   4740
gtttctttaa gcggtcctgt aacagaatgg taaagtgagt tgagcttttc tttcctggta   4800
tttgacagga atttggcact cttggatggt tgagacaaag cacagggcat gcaactcata   4860
tatggatttt aggtaaacag tgaaatggtg aagttatttt atatcaacca tgatgacttc   4920
ctcataatga taggagcatg caactagctg caattatggt cttctctgat acagattctg   4980
aatattgtga ttactgcttg gtgcaaaact aaacttgtga agaaaacaat aacctgatat   5040
```

-continued

| | |
|---|---|
| gccaatcttg taatgcattt tcaatagtgc agaaaacaca aagctagtgg ctgctcaaaa | 5100 |
| tatacacatt ttgtgatgag cggtttctga aggtgctgaa acaatggtgt aatgcaatgt | 5160 |
| tcatgcagca tttgcttcca tgcgccagca cagcttttac aaaaaagaga taatccacaa | 5220 |
| catttggaag ttgcaagcat gccctcacac aatatcgcat gaagcaagaa gatgatatca | 5280 |
| ctacaggcta aagcagtaaa gcaaaaaggg tagataaaga actggatgcc atatactttc | 5340 |
| caactttgtg tgaattatta gacgtgctag aaagtaacaa acctgttgtt caggaatcaa | 5400 |
| ttcctgcagc tgggacttga gatcctgcat ataatattta gaaacacaat caaacatctt | 5460 |
| ttttcagagc acattcccca ctttcgagcc tagccacaga tggcacatag taactggtag | 5520 |
| tttcaaccac acatttagca cgaacgaaca aaaactaatt gacttacaag atcagatgcg | 5580 |
| ctctgcatct gcagccatcg cacaccacca agcgtggtgg cctcctgtgc ctgacaacac | 5640 |

<210> SEQ ID NO 22
<211> LENGTH: 6240
<212> TYPE: DNA
<213> ORGANISM: Oryza sativa
<300> PUBLICATION INFORMATION:
<308> DATABASE ACCESSION NUMBER: AP000559
<309> DATABASE ENTRY DATE: OCT-1999
<313> RELEVANT RESIDUES: 7921 TO 14161

<400> SEQUENCE: 22

| | |
|---|---|
| ttgagaggga ataagctagg tggtggtggt tcttggatca atggcggcgg cgagggcgcc | 60 |
| gtggctgtgg tggtgggtgg tggtggttgt tggtgtggcg gtggcggagg cggcctccgg | 120 |
| aggaggagga gggggagatg ggagggggaa ggcgctgatg ggcgtgaagg ccggtttcgg | 180 |
| gaacgcggcc aacgcgctcg tcgactggga cggcggcgcc gaccactgcg cgtggcgcgg | 240 |
| cgtcacctgc gacaacgcct ccttcgccgt cctcgccctg tacgtcctcc tccctgcgaa | 300 |
| gctcggtgtt ctttcctggg cagacatggc gcgcggcggc gcgggtggtt gcgttcttgt | 360 |
| tcttgcaatc ttctcttgtg gtggctgttg gttttttctt ttcttttctt tttccagcgt | 420 |
| gcactctgtg cttcatgtga ttttttctctc ttgccgtgct cgctctggca ttctgatcag | 480 |
| gaggagcaaa tagttcaact gttctgttct attcttgcct ccctttttt tctgaataaa | 540 |
| aaccttttct tggttggtct atttgtgcct agattgctgt gaatgtttct tcttgataat | 600 |
| cttgttgtta tcgtatatat ctaatggaaa agaaacgggt ttttcttgtt atcttgcgta | 660 |
| ggtctttgga tattagtgag gctatcttgt tgttatgct aaaaaggatt tttgtgatga | 720 |
| gagtgtttcc ctgtgtgaaa acaggaact tgtcaaatct aaacctagga ggtgagatct | 780 |
| cgccggccat cggagagctc aagaatctac agttcgtgtg agtacggata tgagtagaga | 840 |
| gtactatttc cccttgcttt gcatctacct gagttttgt gcatttgact agcctgtatt | 900 |
| ttctttttat aatcctgcac acttcacctg atttgacccc tcatgccatg atgtgacaca | 960 |
| gttctttact atttttacttt aagcctgtgg atttgctcgc tgattagttt atttgtgctc | 1020 |
| taatgatttg cctctctgca gtgatctcaa ggggaacaag ctcactggcc aaatcccaga | 1080 |
| tgagattggg gactgcatct ccttaaaata tttgtacttc acctaatcta agtcttcttt | 1140 |
| tattctgtta cttttttgtaa cagggtgttc tagctaattt tttaattggg ctcttttgat | 1200 |
| tcttgccatg cagggatttg tctggcaact tgctgtatgg agacatcccc ttctccatct | 1260 |
| ccaagctcaa gcagcttgag gagctgtaag ctctactttt tttaaatctt ttcctacctt | 1320 |
| ttctttagca agagctatgg cctatagctg ttgagatatg ggcacttcct ctcccttctt | 1380 |
| tggaaagttc aggctaatac tgagacatca gagactaatt gatttacatt aagttttgga | 1440 |

```
acatcttgtt ctagaatcca gattatgata ctgaacatct tgttggagta gtagtagttt    1500
ttttcatggt tttgcgatgc ttgggttgta gtggtaacat ttttttctctc tcatttattg    1560 atgcaggatt ttgaagaaca accagctcac gggacccatc ccttccacat tgtcccaaat    1620
tccaaatctc aagacattgt gagcctctta gtaccttact ctatccgtga ctatttactt    1680 cttttggggtt cttggacaaa ctgggtgatc tgacttctac ttgtttaact gttttttgtgt    1740 tataatgtgc gtgccacggg aaacatggct tgctgtgtca ttttttgcat cttaagtact    1800
actagttctt acttactgat aaaatccttc cttaattatc ttggaatagg gacctggcac    1860
agaaccagct tacaggcgat atcccaaggc tcatatactg gaatgaagtt ctgcaatacc    1920
tgtaagaatc ctataaaaga aaattgtcta actgttttag ctggtagtat aagaaggtat    1980
ttttcaggca ttaacacttt gcttctctta atcttcagag gtttgagggg taactcactg    2040
actgaaactt tgtcacctga catgtgccaa ctgactggcc tgtggtactt gtaagtcatc    2100
tcctctccct ttggagatgt tgctgcatat tgtgcaactt ggccttgttg acagtggtta    2160
ctgttcttaa tctacagtga tgtaagggga acaatctca cagggaccat tccagagagc    2220
atagggaact gcaccagctt tgagattctg tatgttcttg ctaagatttc agtaatattt    2280
cagtgttcat gagtttcaga caccataatg cgagtttctt atttgtattg cagggacatt    2340
tcgtataacc aaatctctgg agaaatacct tacaacatag gctttcttca agtagccaca    2400
ctgtaagtgt tcctgagtta ttgcaaatcc tctaacatgt aatctgctgt ttcactctta    2460
tgcatataga tgctttactt acagccttta tgttgaacca tttctattca tgttcatagg    2520
tcacttcaag gaaatagact gactgggaaa attccagatg tgattggcct gatgcaagct    2580
cttgctgttc tgtgagtaga gcacgacatt tcaatccata ggttttagta gtttctgtaa    2640
tatttttttg actgaaattc agtagtttct gtaatattgg ataatgaatt cttatattca    2700
ttttttttat tctcagagac ctgagtgaga acgagctggt agggcccatt ccttctatac    2760
tgggcaatct atcctatact ggaaaactgt tagtatcatc agtcagactt tcttttttcac    2820 tgagattgct ttcttctctt ctctaacacc tactgtcacc ttttccttca gatatttaca    2880
tgggaacaaa cttactggag tcataccgcc ggagcttggg aacatgagta aacttagcta    2940
cctgtaagtg attatatggt atgcagatat tgttgtgctc cagttggtgt ggaacactat    3000
aagatgttca gaaattttttc catgcagaca actgaatgat aatgaattgg tgggcacaat    3060
tccagcagag cttggcaaac ttgaagagct ttttgaactg taagaaattt tatcatgtct    3120
atgagttacg tagtatgctt tatttttattc tgtgcaattg ttgaccaaat tttgcatgca    3180
gaaatcttgc caacaacaat cttcaaggtc ctattcctgc aaacatcagt tcttgcactg    3240
ctctaaacaa attgtaagtt agccggtact aagtcaactt ataagttaac agggcatttt    3300
ttactccaca tgattaaaca tgttttttttt ttgcctctca gcaatgttta tggcaataag    3360
ctaaatggtt ctattcctgc tggtttccag aagttggaga gtctgactta cttgtgagta    3420
attgtatctg ttgcattatg cttacagtaa tcatttaatt cactcggcga aattattgta    3480
tttcacctaa tgtttttctt gcttaaaaat acatttaaaa aatacaggaa cctatcttca    3540
aacaatttca aaggcaatat tccttctgag cttggtcaca tcatcaactt ggacacattg    3600
taagtagaaa cttttagctat aattatttac ctggtgttac aagacctgtg ggcgctaaat    3660
gatgttcctt tattattatt tttttgaacag ggatctttcc tacaatgaat tctctggacc    3720
agttcctgct accattggtg atctagagca ccttcttgaa ctgtatgttg cggaccaacc    3780
```

```
tcctagaaac catactgttt ttaatgaaaa aaccataact tatttcatat ggccattatt   3840
acttgatgcc taaatggtta tgctttgact gcaggaattt gagtaagaac catcttgatg   3900
ggccagttcc tgctgagttt ggaaacttga aagcgtcca agtaatgtaa gtgtgttccc   3960
ttgaaacaca tgtaactaac tattatctgt ttgaagccat cctatcatca tgattcagct   4020
gaaccaaaat ttaaattctc agtgatatgt ccaacaacaa cttatctggt agtctgcccg   4080
aggaacttgg acaacttcaa aaccttgata gcctgtgagt tgtatatcat cataaattca   4140
tattatgcgt gtgagatcga aaatcaccta aatattttac tgagctatgg tgttatcatg   4200
caggattctt aacaacaaca atttggttgg ggagatccct gctcaattgg ccaactgctt   4260
cagcttaaat aacctgtaag ttttgtgtgc aagctctgct ctgtagcatt gtatactggt   4320
gataacttgg gcaggattat ttatccttaa gtgcatttca ggaatttgtc atacaacaat   4380
ttatctggac atgtcccgat ggcaaagaac ttctcgaaat tcccaatgga aaggtataag   4440
atggcaccat gcacaatctc tgttatcctt ctattagcat cttctaattt ctgattgcaa   4500
ccagtacata aatcataaat gcagcttctt gggtaatcca ttactgcatg tttactgcca   4560
agattccagc tgtggacact ctcatggaca aagaggtatc agacaagaag ctaacccctt   4620
gtagcttttc actccatttg cttttctgct aaacacatgt tcacttaatt tctattgcag   4680
ttaatatttc aaagacagca attgcttgca ttatcttagg ctttatcata ttgctctgcg   4740
ttctgctgtt ggctatatat aaaacaaatc aaccacagcc acttgtcaaa ggatccgata   4800
agccagtgca aggtatgtgt gcgctatatc tcacccctcc agttgtcgtc gatgaaatta   4860
acagcaagta tgctggcata atggaattca tcttaacctt ttcttaatca tattcaggac   4920
ctccaaagct agttgttctc cagatggaca tggctatcca tacttacgag gacatcatga   4980
ggctgacaga gaatttgagc gagaaataca tcattggcta tggcgcctca agcactgtct   5040
acaaatgtga actcaagagc ggcaaggcca ttgctgtcaa gcggctttac agtcagtata   5100
accatagcct ccgagagttt gaaacagaac tagagacaat tggcagcata cggcacagga   5160
atcttgttag cctccatggc ttctcgctat ctccacatgg aaacttgctc ttctatgatt   5220
acatggaaaa tggttccttg tgggatcttc tccacggtta gggcttgaaa cctttggctc   5280
atggataatt tgttatcatt atgcatctcc cttatgatct atatatgatc cttttcaggt   5340
ccatcaaaga aagtgaagct caactgggac acaagactga ggatcgcggt cggagctgca   5400
caagggctgg cctatctcca ccatgactgc aaccctcgca taatccacag agatgtcaag   5460
tcctccaaca tcctgctcga cgagaacttc gaagcgcacc tctcagattt cggcatagcc   5520
aaatgtgtcc cctctgccaa gtcccatgcc tccacttatg tgctaggaac catcggctac   5580
attgatccgg agtatgccag gacttccagg ctcaatgaga aatctgatgt gtacagcttc   5640
ggcatcgtcc ttctggaatt gctcacaggg aagaaggccg tcgacaacga atcgaacttg   5700
catcaattgg taagccaccc cacttccaca gttccactcc atcctctcat cacattgtgc   5760
aaaattatca ccaattctag aacttttcta gcatgatcca atggatgatt tgtatgacaa   5820
gatcttgtgt caatgttcag atactctcca aagctgatga caacacagtc atggaggcag   5880
tggactcgga ggtgtcagtg acgtgcacgg acatgggact ggtcaggaag gccttccagc   5940
tcgcccttct gtgcaccaag aggcaccctt cagaccggcc gaccatgcac gaggttgcaa   6000
gggtgctgct ctccctgctg ccggcctccg ccatgacaac gcccaagacg gtggactact   6060
cccggttgct ggcgtcgacg acgacggcgg ccgacatgcg agggcacgac gtgaccgaca   6120
tcggcgacaa cagctcctcc gacgagcagt ggttcgtcag gttcggcgag gtcatatcca   6180
```

```
agcacacaat gtgatcttct ccaaacctcc aaaattttct cctccccaag atgctaaaag    6240

<210> SEQ ID NO 23
<211> LENGTH: 2160
<212> TYPE: DNA
<213> ORGANISM: Oryza sativa
<300> PUBLICATION INFORMATION:
<308> DATABASE ACCESSION NUMBER: AP000559
<309> DATABASE ENTRY DATE: OCT-1999
<313> RELEVANT RESIDUES: 76801 TO 78961

<400> SEQUENCE: 23
ccaagaagcc ggcgatggct gcctcggtca cacggtgagc ccccgcatga actcccactc      60
gtcgtcatcc tcctccgccg cgccggcggc cgaccccctcc gagtcgctgc tcatgccgct    120
gctctccccg ctggccatcg ccgcggcctc cgggtcgaac gacaggtacg gcattgcgcc    180
gaacgccctg gcgagcgcgg cggcggtggc cgcgtcggtc ctctgcttga gcacctcgaa    240
catcacctcg ggctcgtgct gcatcgagcg gagcacgtcg gcgcacgacg gccccgccgc    300
cgcgcgcgtg acggcgaagc agtgcggccc gtcgctctgc gacacgcgca ccacgctcgg    360
cccgccgaac aggttgtgga ggccgccgag ggcctcctgg taggcgccgc cgaggaacat    420
gccgaggtag tagccgcggg tgccgtggac ggggagctcg tgcagcggca ggctgtgcct    480
cccgccgatg aagtggtcga ccttgccgtc gctgtcgcag gtgaggtcgg agaggacgcc    540
gtcgaccgca gggcgctcac cgaggcgctg gattgggatg atcgggaaca tctgcccgat    600
cgcccacatg tccggcaggg aggtgaacac ggacaggttg atgtggtacg tgcgcggcgg    660
ctcggcggcg cccatgccgc gggcgacgat ctcgcagagg ctgtccaccg gcgaggtg     720
ctccaggcca agaacgccgt ccttgaactg atcggcgcag cgccgcttca gctggtcggc    780
gtacagagcg caggtgtcga agtcgccgcg caccgcggcg gccatgaggt tgcggtagtc    840
ggcgtggcag tcgtcggtga gctcgtcgag caggtagccc gtggccgggt caatgcggcc    900
gggcgccgaa gccgagaagg cctcgaacac caggacagag tggtgcgaca ccagcgcgcg    960
gccgctctcg ctgcagatga tgggatgcgc gacgcccttg cggtcacaga cgcggccgac   1020
ggcggccacc acggccgccg cgtactcctc caagctgtat gccacggaca tgtcggtctg   1080
cgccgagtga ctcccgtcgt agtcaatgcc gaggcctcca ccaacgtcga tgacgcgcat   1140
ggccgcgccc aggcgggcga gctcgcagta gatctgcgcg gcctccccga cgccatcgcc   1200
gagcagagca gtggtcggga tctgggagcc aatgtggaag tgcaggagct ggaggcagtc   1260
gagcatacca agggtcttga gcttggcgac gacggagaga atctgcgcgg cgttgaggcc   1320
gaacttgccc ttctccccgg acgtggagcc gaagtggccg gcgtgcttgg tgcgcagctt   1380
ggcgcgcatg ccgaccaccg ggcgcacgcc gaggcggcgg ctagcgtcga ccacaatgtc   1440
gagctcctcc tcctgctcga gcacgatgac cgtgttgagc cccatggtgc gcgcgatgag   1500
cgcgagcgag acgtactcgt cgtccttgta gccgttgcag atgagcaggg cgtccgggtt   1560
gccgcgcgcg gcgaggcagc tcatggcgag cagcagctcg ggcttggagc cggcctccag   1620
gccgaagcgg aacggctcgc cgaactccac aatgtcctcc acgacgtggc ggtcctggtt   1680
gcacttgacg gggtacacgc cctggtacct cccgccatag ccggtggagc gcacggcgta   1740
gtcgaacgcc gcgttcaggg cctccacgcg gtggcggagc acgtcgggga accgcaccag   1800
caggggagc ggcaggccga gcccgccgcc ggagcgcggg ccggcggcct tggccaccac   1860
cttggcgagg tcgatctcct gcccgggcag ggttgcggcg ccgtgcgggc gcacggcgac   1920
```

-continued

| | |
|---|---|
| gtcgccgtcg tcgttgacga agaagtacgg cgcgccccag ccgtccacgt tgtacagcgc | 1980 |
| ggacgagagg tcggccgacc acgcggccgc gtccggcttc ccgccaccg ccgcagccgc | 2040 |
| ggcggcgggg cccagcagcg gcgcggggaa gcgcgccgcg tcgcacgcga aggcgtgcgc | 2100 |
| gacaggtgca gcggcgtcca cggcgagcgc aggcatctcg tcacaaaccg gagaacgcta | 2160 |

<210> SEQ ID NO 24
<211> LENGTH: 3480
<212> TYPE: DNA
<213> ORGANISM: Oryza sativa
<300> PUBLICATION INFORMATION:
<308> DATABASE ACCESSION NUMBER: AP000570
<309> DATABASE ENTRY DATE: OCT-1999
<313> RELEVANT RESIDUES: 49981 TO 53461

<400> SEQUENCE: 24

| | |
|---|---|
| tcaaccagat ctaggagtcc catgttcttc caggctgctg cctaggctgc gaggacgatt | 60 |
| atcactatga gcaggaccac cccgaatata accagcaaca agcatatctg caacataaaa | 120 |
| tgagaatcga acaatgtttc acatgttgaa gtgagtgcca gtgaaatata ttaatgagtg | 180 |
| ctaaaggagt ctaaaagtac cagcgaagag ttcgacttct gagttttagc agccttagag | 240 |
| agttggcctt ttgcttgtgt agtcgctata acagcattct cgatatgggt gtcaatgtca | 300 |
| tctgcagtat aggaggagat acacaatcag atataacata ccagatatat gagcagcctc | 360 |
| gtgcttcaac gtatcaaata gcacataatc ccatctatca tccccaacgg taccacatac | 420 |
| caatcatttg tccttgatcg tggactagaa cagcaagatc tttgaagatt tcatttactt | 480 |
| cagtaatttg gtgctgaatt tcttgtattc cctgatccct ctcctcaatg acggcctcat | 540 |
| tgaacacgat ctcattatcc aagaagacta attcttgcct acagtaaaga aaaaaattga | 600 |
| ggttatcatg ttcacacatt tgcaaaggag tgaatttgtt cattcatttc aaaacaagtg | 660 |
| aatactttat agaaatgttc gaaaacaaat agtccaaagc ataaccaaat agtactatca | 720 |
| attcaccttc ttgattctag aagcgccgtg cgttgctcag ccaacttatc agcaccattg | 780 |
| ttcacctcgc tcgagttata gctgcaaaga acaagccatc ctagattact catatgttga | 840 |
| caacatactg gaaaaacttt gacaatatat tatcatagac cagcctcaaa aatatgttgt | 900 |
| tattattatt acagaaaatt aacatataat gaatgtgagg tacaaaattt tgcaatgatc | 960 |
| taaagtacca ttgaatggag ataattttaa gaaaataatg ttttgctgtt ttacttggaa | 1020 |
| gacccaagaa gacaggctac acttgaaagt ggtttttatta ttctgagttc tatgaataag | 1080 |
| acaaacttca tcgcaagttt agtcagaaaa tgaatttatg atattgaaag ctagggcctg | 1140 |
| ggggctgaga aagtggacca tgaacaaaac gctagatatt taagggtaaa acaggcagag | 1200 |
| aaacttatac gctacagtag atcaaaacag caatacgaac tatttggata ggatcaaata | 1260 |
| tgaatgctca tcctgtaaat gcgcaccaga aggtattgta ttaggttgga ataaaccagg | 1320 |
| gcattaacta ttagggtcat caagcacttg gcagattaaa agcactaatc cagtgttatt | 1380 |
| attattccat ttacctcaga aaacataatc cagtgttaag tccagtcaaa ctgaaaatat | 1440 |
| tttttttcatg aaatttttt aaaacttgac gtagaataat ttatttgttc aagagagagt | 1500 |
| atgcaacaaa attattctgc agagtaagta aaatgtaaca ggatgctgta gcattagtac | 1560 |
| actaccaaga aaatgataaa caatatgcca tgaattatat tattgtagta agtgcacttt | 1620 |
| tgttcaaaaa cataagatgc aggaagaaa aataagcaag tatttacaga aagaagtaca | 1680 |
| ccagctgact agcaaactac ctttgtggca agcccgcttg agaaatgaag ggtgcataag | 1740 |
| cagcttctct ttctaccgct aaccgttgag ctttctgaaa ttctttcaga actgcttgga | 1800 |

```
aatcctttgc tagcttcgca tcagcaatct ttttgctggc ctgtagttcc aaacgaggtc   1860
atcaacacac attgtgtaat acatcagcaa aaatggaaca tagaaatgtt ccttaaaata   1920
gtaatgatca tagattcata ggcaatcaat actacataaa gcagctcata taagaaatgc   1980
aaatgctaca tttgatctct acatgattct aaaatctgct tgtagattat ttctccagtg   2040
gcatggcaac acacttgaaa atatcatgac tggagcatat tgagtattta agaaaacaat   2100
ttgttttatg tgctgaggca aatcactgtt cacagtagtc aggcaaaact aagactgata   2160
cagataaaaa atgcccaaat tagaagtgat gtttccagtc agaatataag gactgggtag   2220
gttcagtttc caaaccaata tgcattatta cactcttctg tactttgaag gaaaatgtca   2280
aaattgaagg ttttctggtt caaaagtag catcacatgt tgcaattcca tttcattttg   2340
atgcaaaagg tgaagagtac tgaaataatt ctggtttcaa acatacaaga tagaaacagt   2400
tccaattctg ttttgagaaa aaagcaactt ggacaaagat gcaagagaat acttacgctg   2460
acttcgacac gatgatcagc ctcgctagct tgtttaagct tctccgatgt gtccttcacc   2520
agttgtgtta tgtgttgacg tgtcttgtgt ctgcaagcaa caccaacaga agtaaatcg   2580 acccatcaaa ccaaaaaaat aactagtcta aagtacagaa aaagggttaa ggcataatac   2640
aagttactac actataagac agcatgccag gccatacatg gcataaattg aatcaatttc   2700
agtagaaagg aatggagaaa acatcttatt cgaggccatc ggatctattc atataccagg   2760
aatggcatga ttcatcaatt ctacctaagt tcagcggcta tcacccaaac atgagttgct   2820
agtagataaa ctacaggcag ggctccccaa attgaatccc taattatcac taatacataa   2880
ttatcacgaa gagaagggag aagcaatcct aagcaacacg taataagaga gatatcacga   2940
agagaagggg agaagcgatc cctaagcaac acataatatg agagacatag gttcatcacg   3000
cgaatcgacc gcataaacat ataacctaat cgagatcgca aatcatgcag cggagccgca   3060
caattccccc ccaaaattca tcacgcgcat ccaaaatcgg agccccggat cgcaaaatcc   3120
cccaatcccc cgctccaaat cgaaccaaaa tcgatccccc gaccccgct ccaaatcaaa   3180 ccaaaaccaa acagacgtgg ggtaggtaga gagtatggcg cggggggagc ctcacatcct   3240
ctcgcggagg tcggggtgt ccttgggcgt gccgagcgtg ttgaccagcc gctggaacgt   3300
cgacaccgcc gtgttgatct ggaacacccc gacgccacg gcctgcgacg ccccgcccc   3360 ggcggccgcg gcgcccgccc tgccgccacc gccctccgc ggcagccgc gggcgttccc   3420 cgcctccagg tcctggaagc tcatcctcct cctccctccc cgccgcctcc tcctccgatc   3480
```

<210> SEQ ID NO 25
<211> LENGTH: 2880
<212> TYPE: DNA
<213> ORGANISM: Oryza sativa
<300> PUBLICATION INFORMATION:
<308> DATABASE ACCESSION NUMBER: AP000836
<309> DATABASE ENTRY DATE: DEC-1999
<313> RELEVANT RESIDUES: 95341 TO 98221

<400> SEQUENCE: 25

```
gccagcggaa ccgctcatcc ttactgctca cccgtggtct tgatgatatc cgagtcacct     60
ggaaatcaag cgcattgtac agtattacta tcaaataacg gttttgttta gtttcttca    120 aatactaggt agacgtatgg aagttaccag gatcaataat gctgaggcag caaacacgga    180
agtatttacc acaggctgtc cccagatcga cattatctga aaacaaacag atagctgtta    240
tttttcaaac aaagacacag ctaatgtaat aagactggct aatcaagcaa tatgggcata    300
```

```
tggcagaaac cgatgtctgc acagtttatt catttgtcct atctatgaat ttgtaagtct    360
tctttggtcc actttgcagt tgctacaaac aaatgcagca ttgccatggc aacagaagat    420
agaactgtgc accttatttc agtttcattt aaaaaaacgc ataaaaataa ttagcatggc    480
gtttctacga tataatttga ttacatattt actcccaagc atgcctcact gtttaaatct    540
ttgcaaaggt caagagatgt cgaaaagcat gggtgtcaac ttacttccgt ggaaatggtg    600
gacggtgacc ttggccaaca tagcgtagta ctcaatttct gacttccgaa gaggtgggca    660
gttgttagaa atgatcacta gcttcgctgt aatgaagaca tgcggggaca ttagatatca    720
gtctgccagc aaagatgaca aaacaaagta gggtagtatg cagccatgct ctgaaaagtt    780
tacacaatga aaagagctg atgaaagtaa aacattacat gcaaatggtc agagagaaaa    840
aaggacactc tacaagctta attccctaca gttacgaaaa attttccttg caatcatact    900
gaagactcat agtaaaaaaa cgttttcat aaagcatgtt tccacttctg caaataagca    960
gttgacatca cagttactgt atgcagaaaa tggagaatta ttatggcgtt gactcataca   1020
cattggccat attggtacta atccaccgg taatcagttt tcaacgctaa aggtttcaac    1080
ctggagcaac aaatttgcaa agatcataat agacaattat ctatgttatc atacccaagc   1140
taaacaattg aacatatcaa taaatccatc acagtctagg aaacaaccac tgcttgctca   1200
aaataaaagg aaatgcctgc ataagatttg gagaatcaga atactggctt ggttctcaaa   1260
agagaaataa tagcgctcag tatgttcatt gtcgatcatc tggggaaagg atcatcatat   1320
tctccatatt aagcagcacc aaataaaatt tcaccacaac atgctaaaag aatcaggaaa   1380
aataggcagc acaatgaaat taaccacaaa tcagtacatt ttcagataaa acaaatcttt   1440
cagcaaaaga gactgcatta aatttggaga atcatagttc tggcttgatt atctcttaag   1500
agaacaatag cgcacattat gctcatcgtc gatcatctgg ggaaaggatc gtcatatcct   1560
ccactaccaa ttcaaccaaa actaaataaa gaaagtgcac tacaacatac aggctactca   1620
gctaggacaa acagctgata acacataaa ctagaaatag cttgacaacg tattcacatt    1680
tgagtacaac acagccaaac aaaaagcata caggaatatg tcaagtcttg gctaagtcta   1740
tgttaatact aaaccataaa gcgtatatac accactgcca aatactgaac cacaacatcg   1800
agcacattca gaagaacaat gacagtgggg catggctatg gcatcgactc atacacagca   1860
gcaatgagat ccaccggtaa tcagtttata cgatgcgcat actcacacta acatccatcc   1920
aaaggatgat ggtaaataag cacaatgaaa ctaatcaaga accaactcat ttgaagataa   1980
aggaaatctt tcagaaaaaa aaactctaca ttaaaattcg aggatcagat ttctggcttg   2040
attatctcct aagagaaaac aatcgcacgg tatgttcatt gtcgatcatc tggggaaagg   2100
atcatcatat cctccgtatg gacatatcca aagctaaaat gtagacaaca gcacacagca   2160
atacaacata caggcaataa aaaaacagag agcgggtaca agtcaacata caggcaataa   2220
aaaaacagag agcgggtata agtttcattg ggtacaaaga ttgaatgtaa gagggaatg    2280 ttttaagtct tggggtaagt ccatgtaaat cctacctaag tatatacacc accatcagct   2340
actgaacagc aatatcaagc acattcagaa gaacagagac agtggggcta atcactgtgg   2400
catcgactca tacgcggcgg cgatgagatc caccggtaat cagttattac gatgcccaaa   2460
ctcactataa aaccgcaata ctaacaacac ggatgcgaac cttaaactag aatttggcgt   2520
aatctaacag ggaaaggaga gcattgatcc atcttaccct tggagttcct gagggtcctg   2580
aggacggtct tgtagccgag cgtgtacttg ccgctcttca tcacgagctg cagcttgttg   2640
ttgatgttgt ccgtggactt cttctgcaaa cacaaccacc atcacaccat caccacgacg   2700
```

```
aacagagagg cgttagcgcc atgagaaatg caggatctcg ctcgctcgct cgcttgcgcg    2760
gcggaccgag gtgatggagg gagagaccgg gaggaggaca acgttaccgt cttctttgcg    2820
gccaccatgg ctgcgccccg aggagaagcg acggcggcga gggtttcggg cggcggcggc    2880

<210> SEQ ID NO 26
<211> LENGTH: 115
<212> TYPE: DNA
<213> ORGANISM: Osa#3

<400> SEQUENCE: 26
aattcgtgag acgaatcttt tgagcctaat tacgtcatga tttgacaatg tgatgctaca     60
ataaactttt tataattata gattaattag gtttaaaaaa ttcgtctcgc ggatt         115

<210> SEQ ID NO 27
<211> LENGTH: 115
<212> TYPE: DNA
<213> ORGANISM: Osa#6

<400> SEQUENCE: 27
aaattgcgag acgaatcttt tgagcctaat tacaccatga tttgacaatg tgatgctaca     60
gtaaacattt gctaataaca gattaattag gcttaataaa ttcgtctcgc agttt         115

<210> SEQ ID NO 28
<211> LENGTH: 116
<212> TYPE: DNA
<213> ORGANISM: Osa#7

<400> SEQUENCE: 28
aaatcgcgag acaaattttt ttagcctaat tagtccatga ttagctataa gtactacagt     60
aatccatatg tataatagta gtttaattag gcttaataaa ttcgacttcc tgtttc        116

<210> SEQ ID NO 29
<211> LENGTH: 115
<212> TYPE: DNA
<213> ORGANISM: Osa#8

<400> SEQUENCE: 29
aaattaggag acaaatcttt taagtctaat tgttccatga tttggtaata tgatgctaca     60
gtaaacattt gctaatgaca gattaattag acttaataaa tttgtcccgt ggttt         115

<210> SEQ ID NO 30
<211> LENGTH: 115
<212> TYPE: DNA
<213> ORGANISM: Osa#9

<400> SEQUENCE: 30
aattcgcgtg acaaattttt taagcctaat taatctgtaa ttagcgcatg tttactgtcg     60
catcccatag gctaatcatg gattaattag gctcaataga ttcgtctcgc aaatt         115

<210> SEQ ID NO 31
<211> LENGTH: 116
<212> TYPE: DNA
<213> ORGANISM: Osa#10

<400> SEQUENCE: 31
aaattacgag atgaatattt taagtctaat tgctccatga ttttataatg tggtgctaca     60
gtaaacattt gctaatgatg gattaaatta ggcttaataa atttgtctcg cagtat        116
```

<210> SEQ ID NO 32
<211> LENGTH: 115
<212> TYPE: DNA
<213> ORGANISM: Osa#12

<400> SEQUENCE: 32

```
aattcgcgag acgaatctat tgagcctaat taatccatga ttagcctatg tgatgctaca    60
gtaaacattc tctaattatg gattaattag gcttaaaaaa tttgtctcgc aaatt         115
```

<210> SEQ ID NO 33
<211> LENGTH: 115
<212> TYPE: DNA
<213> ORGANISM: Osa#16

<400> SEQUENCE: 33

```
aaatcgcgag actaatcttt tgagcctaat tacgccatga tttgacaata ttgtgctaca    60
gtaaatattt gctaatgctg gattaattaa gcttaataga tttatctcac agttt         115
```

<210> SEQ ID NO 34
<211> LENGTH: 115
<212> TYPE: DNA
<213> ORGANISM: Osa#17

<400> SEQUENCE: 34

```
aattcgcgag acgaatcttt tgagtctaat tacgccatga tttgacaatg tgatgctaca    60
gtaaactttt gataattatg gattaattag gcttaaaaaa tccgtctcgc ggatt         115
```

<210> SEQ ID NO 35
<211> LENGTH: 112
<212> TYPE: DNA
<213> ORGANISM: Osa#18

<400> SEQUENCE: 35

```
aaattgcgag acgaattttt ggcctaatta cgccatgatg tgacaatttg gtgctaaata    60
aacatttgct aatgatggat taattaggct taataaattc gtctagttgt tt            112
```

<210> SEQ ID NO 36
<211> LENGTH: 115
<212> TYPE: DNA
<213> ORGANISM: Osa#24

<400> SEQUENCE: 36

```
aaattgcgag acgaatcttt taagcctaat tgcgccatga tttaacaata tgatgctaca    60
gtaaatattt gctaatgaca gattaattag gcttaataaa ttcatctcgc atatt         115
```

<210> SEQ ID NO 37
<211> LENGTH: 115
<212> TYPE: DNA
<213> ORGANISM: Osa#29

<400> SEQUENCE: 37

```
aaattgcgag atgaatcttt taagcctaat tgcgccatga tttgacaatg tggtgctaca    60
ttaaacactt gctaatgacg gattaattag gcttaataaa ttcgtctcgc agttt         115
```